US010731205B2

(12) United States Patent
Wu et al.

(10) Patent No.: US 10,731,205 B2
(45) Date of Patent: Aug. 4, 2020

(54) MICROFLUIDIC PLATFORM FOR MULTIPLEXED DETECTION IN SINGLE CELLS AND METHODS THEREOF

(71) Applicant: National Technology & Engineering Solutions of Sandia, LLC, Albuquerque, NM (US)

(72) Inventors: Meiye Wu, Tracy, CA (US); Anup K. Singh, Danville, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 268 days.

(21) Appl. No.: 15/925,389

(22) Filed: Mar. 19, 2018

(65) Prior Publication Data
US 2018/0208978 A1    Jul. 26, 2018

Related U.S. Application Data

(62) Division of application No. 14/575,886, filed on Dec. 18, 2014, now Pat. No. 9,957,554.
(Continued)

(51) Int. Cl.
| | | |
|---|---|---|
| *C12Q 1/6837* | (2018.01) | |
| *C12Q 1/6844* | (2018.01) | |
| *C12Q 1/6841* | (2018.01) | |
| *C12Q 1/6804* | (2018.01) | |
| *G01N 33/536* | (2006.01) | |
| *C12Q 1/6816* | (2018.01) | |
| *G01N 15/14* | (2006.01) | |
| *C40B 30/04* | (2006.01) | |
| *G01N 15/10* | (2006.01) | |
| *B01L 3/00* | (2006.01) | |

(52) U.S. Cl.
CPC ........ *C12Q 1/6837* (2013.01); *C12Q 1/6804* (2013.01); *C12Q 1/6816* (2013.01); *C12Q 1/6841* (2013.01); *C12Q 1/6844* (2013.01); *G01N 15/1459* (2013.01); *G01N 33/536* (2013.01); *B01L 3/502776* (2013.01); *C40B 30/04* (2013.01); *G01N 15/1484* (2013.01); *G01N 2015/1006* (2013.01)

(58) Field of Classification Search
None
See application file for complete search history.

(56) References Cited

U.S. PATENT DOCUMENTS 5,641,457 A    6/1997  Vardanega et al.
5,665,539 A    9/1997  Sano et al.
(Continued)

OTHER PUBLICATIONS

Wu et al., "Single Cell MicroRNA Analysis Using Microfluidic Flow Cytometry," PLoS ONE 2013, 8(1):e55044, published Jan. 30, 2013) (Year: 2013).*
(Continued)

*Primary Examiner* — Kaijiang Zhang
(74) *Attorney, Agent, or Firm* — Helen S. Baca

(57) ABSTRACT

The present invention relates to a microfluidic device and platform configured to conduct multiplexed analysis within the device. In particular, the device allows multiple targets to be detected on a single-cell level. Also provided are methods of performing multiplexed analyses to detect one or more target nucleic acids, proteins, and post-translational modifications.

11 Claims, 16 Drawing Sheets

Specification includes a Sequence Listing.

Related U.S. Application Data

(60) Provisional application No. 61/918,402, filed on Dec. 19, 2013.

(56) References Cited

U.S. PATENT DOCUMENTS

| | | |
|---|---|---|
| 6,296,810 B1 | 10/2001 | Ulmer |
| 6,428,666 B1 | 8/2002 | Singh et al. |
| 6,495,352 B1 | 12/2002 | Brinker et al. |
| 6,511,809 B2 | 1/2003 | Baez et al. |
| 6,558,928 B1 | 5/2003 | Landegren |
| 6,878,515 B1 | 4/2005 | Landegren |
| 7,014,747 B2 | 3/2006 | Cummings et al. |
| 7,074,564 B2 | 7/2006 | Landegren et al. |
| 7,116,407 B2 | 10/2006 | Hansen et al. |
| 7,264,723 B2 | 9/2007 | Singh et al. |
| 7,344,681 B1 | 3/2008 | Fiechtner et al. |
| 7,502,123 B2 | 3/2009 | Schmidt et al. |
| 7,534,315 B1 | 5/2009 | Singh et al. |
| 7,534,334 B1 | 5/2009 | Fiechtner et al. |
| 7,602,307 B1 | 10/2009 | Brennan et al. |
| 7,754,077 B1 | 7/2010 | Singh et al. |
| 7,828,948 B1 | 11/2010 | Hatch et al. |
| 7,931,792 B2 | 4/2011 | Fiechtner et al. |
| 7,999,937 B1 | 8/2011 | Srivastava et al. |
| 8,047,829 B1 | 11/2011 | Sommer et al. |
| 8,163,154 B1 | 4/2012 | Hatch et al. |
| 8,257,964 B2 | 9/2012 | Hung et al. |
| 8,268,554 B2 | 9/2012 | Schallmeiner |
| 8,329,016 B1 | 12/2012 | Sommer et al. |
| 8,394,312 B1 | 3/2013 | Sommer et al. |
| 8,524,060 B1 | 9/2013 | Herr et al. |
| 8,675,196 B2 | 3/2014 | Ozasa |
| 8,702,946 B1 | 4/2014 | Chirica et al. |
| 8,703,058 B1 | 4/2014 | Hatch et al. |
| 8,728,290 B1 | 5/2014 | Sommer et al. |
| 8,871,496 B1 | 10/2014 | Sommer et al. |
| 8,911,606 B1 | 12/2014 | Chirica et al. |
| 8,945,914 B1 | 2/2015 | Schaff et al. |
| 8,961,766 B2 | 2/2015 | Herr et al. |
| 9,002,654 B2 | 4/2015 | Braun et al. |
| 9,005,417 B1 | 4/2015 | Sommer et al. |
| 9,186,668 B1 | 11/2015 | Schaff et al. |
| 9,201,069 B2 | 12/2015 | Hatch et al. |
| 9,244,065 B1 | 1/2016 | Schaff et al. |
| 9,409,357 B1 | 8/2016 | Sommer et al. |
| 2004/0112751 A1 | 6/2004 | Han et al. |
| 2005/0105077 A1 | 5/2005 | Padmanabhan et al. |
| 2005/0162648 A1 | 7/2005 | Auer et al. |
| 2009/0036324 A1 | 2/2009 | Fan et al. |
| 2009/0251155 A1 | 10/2009 | Wang et al. |
| 2011/0129850 A1 | 6/2011 | Tseng et al. |
| 2012/0085644 A1 | 4/2012 | Renzi et al. |
| 2012/0214189 A1 | 8/2012 | Shuler et al. |
| 2012/0231976 A1 | 9/2012 | Wu et al. |
| 2014/0194311 A1 | 7/2014 | Gullberg et al. |

OTHER PUBLICATIONS

U.S. Appl. No. 12/182,755, filed Jul. 30, 2008, Hatch et al.
U.S. Appl. No. 14/090,040, filed Nov. 26, 2013, Koh et al.
U.S. Appl. No. 14/546,876, filed Nov. 18, 2014, Koh et al.
Boyce M et al., "Bringing chemistry to life," *Nat. Methods* Aug. 2011;8(8):638-42.
Castoldi M et al., "A sensitive array for microRNA expression profiling (miChip) based on locked nucleic acids (LNA)," *RNA* 2006;12:913-20.
De Planell-Saguer M et al., "Rapid in situ codetection of noncoding RNAs and proteins in cells and formalin-fixed paraffin-embedded tissue sections without protease treatment," *Nat. Protoc.* 2010;5:1061-73 (abstract, 2 pp.).
Duncan DD et al., "Absolute quantitation of microRNAs with a PCR-based assay," *Anal. Biochem.* 2006;359:268-70.
Flatz L et al., "Single-cell gene-expression profiling reveals qualitatively distinct CD8 T cells elicited by different gene-based vaccines," *Proc. Nat'l Acad. Sci. USA* Apr. 5, 2011;108(14):5724-9.
Gullberg M et al., "Cytokine detection by antibody-based proximity ligation," *Proc. Nat'l Acad. Sci. USA* 2004;101(22):8420-4.
Gustafsdottir SM et al., "Proximity ligation assays for sensitive and specific protein analyses," *Anal. Biochem.* 2005;345:2-9.
James CD et al., "Nuclear translocation kinetics of NF-kappaB in macrophages challenged with pathogens in a microfluidic platform," *Biomed. Microdevices.* Jun. 2009;11(3):693-700.
Kumar R et al., "The first analogues of LNA (locked nucleic acids): phosphorothioate-LNA and 2'-thio-LNA," *Bioorg. Med. Chem. Lett.* 1998;8(16):2219-22.
Leuchowius KJ et al., "In situ proximity ligation assay for microscopy and flow cytometry," *Curr. Protoc. Cytom.* 2011;Chapter 9:Unit 9.36 (abstract, 1 p.).
Liu P et al., "Microfluidic fluorescence in situ hybridization and flow cytometry (μFlowFISH)," *Lab Chip* Aug. 21, 2011;11(16):2673-9.
Liu Y et al., "Microfluidic platforms for single-cell protein analysis," *J. Lab. Autom.* Dec. 2013;18(6):446-54.
Liu Y et al., "Single-cell measurements of IgE-mediated FcεRI signaling using an integrated microfluidic platform," *PLoS One* 2013;8(3):e60159 (12 pp.).
Lu LF et al., "Foxp3-dependent microRNA155 confers competitive fitness to regulatory T cells by targeting SOCS1 protein," *Immunity* 2009;30:80-91.
Martin P et al., "CD69 association with Jak3/Stat5 proteins regulates Th17 cell differentiation," *Mol. Cell. Biol.* 2010;30:4877-89.
Marzio R et al., "CD69 and regulation of the immune function," *Immunopharmacol. Immunotoxicol.*1999;21:565-82 (abstract, 1 p.).
Nielsen BS, "MicroRNA in situ hybridization," *Methods Mol. Biol.* 2012;822:67-84 (abstract, 1 p.).
Pena JT et al., "miRNA in situ hybridization in formaldehyde and EDC-fixed tissues," *Nat. Methods* 2009;6:139-41.
Perroud TD et al., "Isotropically etched radial micropore for cell concentration, immobilization, and picodroplet generation," *Lab Chip* Feb. 21, 2009;9(4):507-15.
Perroud TD et al., "Microfluidic-based cell sorting of Francisella tularensis infected macrophages using optical forces," *Anal. Chem.* Aug. 15, 2008;80(16):6365-72.
Powell AA et al., "Single cell profiling of circulating tumor cells: transcriptional heterogeneity and diversity from breast cancer cell lines," *PLoS One* 2012;7:e33788 (11 p.).
Raymond CK et al., "Simple, quantitative primer-extension PCR assay for direct monitoring of microRNAs and short-interfering RNAs," *RNA* 2005;11:1737-44.
Robertson KL et al., "LNA flow-FISH: a flow cytometry-fluorescence in situ hybridization method to detect messenger RNA using locked nucleic acid probes," *Anal. Biochem.* 2009; 390(2):109-14.
Robertson KL et al., "Locked nucleic acid and flow cytometry-fluorescence in situ hybridization for the detection of bacterial small noncoding RNAs," *Appl. Environ. Microbiol.* 2012;78(1):14-20.
Robertson KL et al., "Monitoring viral RNA in infected cells with LNA flow-FISH," *RNA* 2010;16(8): 1679-85.
Silahtaroglu AN et al., "FISHing with locked nucleic acids (LNA): evaluation of different LNA/DNA mixmers," *Mol. Cell. Probes* 2003;17(4):165-9.
Söderberg O et al., "Direct observation of individual endogenous protein complexes in situ by proximity ligation," *Nat. Methods* Dec. 2006;3(12):995-1000.
Srivastava N et al., "Fully integrated microfluidic platform enabling automated phosphoprofiling of macrophage response," *Anal. Chem.* May 1, 2009;81(9):3261-9.
Steinberg TH et al., "Global quantitative phosphoprotein analysis using Multiplexed Proteomics technology," *Proteomics* Jul. 2003;3(7):1128-44.
Steinberg TH et al., "Rapid and simple single nanogram detection of glycoproteins in polyacrylamide gels and on electroblots," *Proteomics* Jul. 2001;1(7):841-55.
Tang F et al., "220-plex microRNA expression profile of a single cell," *Nat. Protoc.* 2006;1:1154-9 (abstract, 1 p.).

(56) References Cited

OTHER PUBLICATIONS

Tang F et al., "MicroRNA expression profiling of single whole embryonic stem cells," *Nucleic Acids Res.* 2006;34:e9 (7 pages).
Thai TH et al., "Regulation of the germinal center response by microRNA-155," *Science* 2007;316:604-8.
Thomson JM et al., "A custom microarray platform for analysis of microRNA gene expression," *Nat. Methods* 2004;1:47-53.
Valoczi A et al., "Sensitive and specific detection of microRNAs by northern blot analysis using LNA-modified oligonucleotide probes," *Nucleic Acids Res.* 2004;32:e175.
Wu M et al., "Microfluidic molecular assay platform for the detection of miRNAs, mRNAs, proteins, and posttranslational modifications at single-cell resolution," *J. Lab. Autom.* Dec. 2014;19(6):587-92.
Wu M et al., "Microfluidically-unified cell culture, sample preparation, imaging and flow cytometry for measurement of cell signaling pathways with single cell resolution," *Lab Chip* Aug. 21, 2012;12(16):2823-31.
Wu M et al., "miRNA detection at single-cell resolution using microfluidic LNA flow-FISH," *Methods Mol. Biol.* 2014;1211:245-60.
Wu M et al., "Single cell microRNA analysis using microfluidic flow cytometry," *PLoS One* 2013;8(1):e55044 (6 pages).
Wu M et al., "Single-cell protein analysis," *Curr. Opin. Biotechnol.* Feb. 2012;23(1):83-8.
Xu G et al., "Transcriptome and targetome analysis in MIR155 expressing cells using RNA-seq," *RNA* 2010;16:1610-22.
Yilmaz S et al., "Single cell genome sequencing," *Curr. Opin. Biotechnol.* 2012;23:437-43.

\* cited by examiner

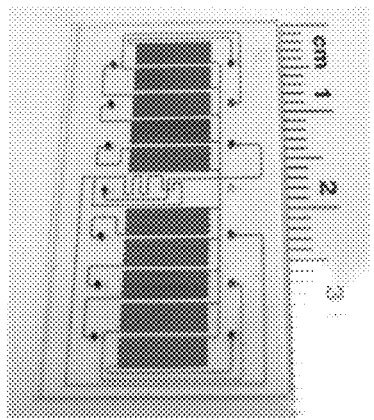
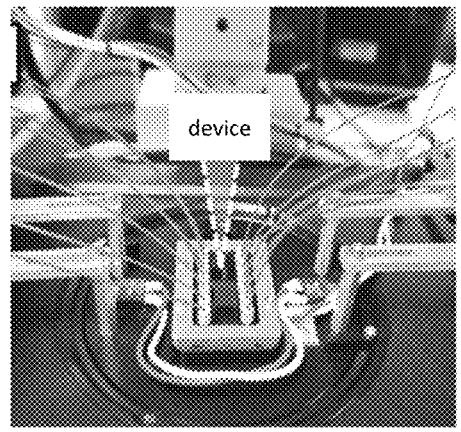
FIG. 2A	FIG. 2B
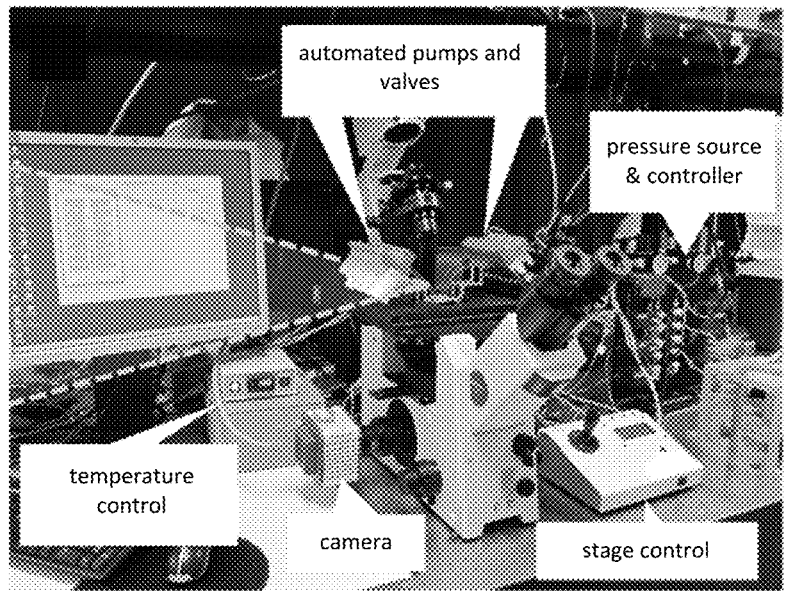
FIG. 2C
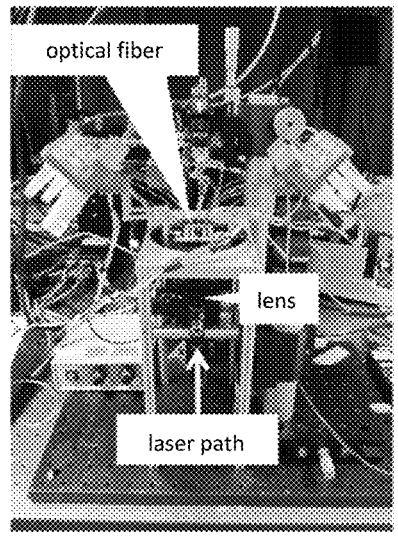
FIG. 2D

SEQUENCE LISTING

<160> NUMBER OF SEQ ID NOS: 4

<210> SEQ ID NO 1
<211> LENGTH: 23
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Modification with digoxigenin
<220> FEATURE:

```
<221> NAME/KEY: misc_feature
<222> LOCATION: (23)..(23)
<223> OTHER INFORMATION: Modification with digoxigenin

<400> SEQUENCE: 1
acccctatca cgattagcat taa                                          23

<210> SEQ ID NO 2
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Modification with digoxigenin
<220> FEATURE:
<221> NAME/KEY: misc_feature
<222> LOCATION: (22)..(22)
<223> OTHER INFORMATION: Modification with digoxigenin

<400> SEQUENCE: 2
gtgtaacacg tctatacgcc ca                                           22

<210> SEQ ID NO 3
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<223> OTHER INFORMATION: Modification with biotin

<400> SEQUENCE: 3
ctcattgtag aaggtgtggt gcca                                         24

<210> SEQ ID NO 4
<211> LENGTH: 22
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Modification with biotin

<400> SEQUENCE: 4
gtgtaacacg tctatacgcc ca                                           22
```

MICROFLUIDIC PLATFORM FOR MULTIPLEXED DETECTION IN SINGLE CELLS AND METHODS THEREOF

CROSS-REFERENCE TO RELATED APPLICATION

This application is a divisional of prior application Ser. No. 14/575,886, filed Dec. 18, 2014, which in turn claims the benefit of U.S. Provisional Application No. 61/918,402, filed Dec. 19, 2013. Each application is hereby incorporated by reference in its entirety.

STATEMENT OF GOVERNMENT INTEREST

This invention was made with Government support under Contract No. DE-NA0003525 awarded by the United States Department of Energy/National Nuclear Security Administration. The Government has certain rights in the invention.

FIELD OF THE INVENTION

The present invention relates to a microfluidic device and platform configured to conduct multiplexed analysis within the device (i.e., on-chip). Also provided are methods of performing multiplexed analyses to detect one or more target nucleic acids, proteins, and post-translational modifications.

BACKGROUND OF THE INVENTION

Cellular signaling networks include complex reactions between numerous biomolecules, such as RNA, DNA, and proteins. In addition, individual cells behave differently, further necessitating tools that can detect different types of biomolecules on a single-cell level. Studies of signaling networks can elucidate and decipher the molecular mechanisms of cellular and disease processes. Such a study requires an integrated, multiplexed platform that enables a systems-level investigation of the complex interactions between these signaling biomolecules. To date, no technology exists that can integrate the detection and analysis of all the signaling molecules, particularly at the single-cell level. Thus, additional tools and systems are desired to perform such single-cell studies.

SUMMARY OF THE INVENTION

The present invention relates to an automated microfluidic platform for performing multiplexed molecular assays for simultaneous detection of microRNA, mRNA, DNA, and/or proteins (e.g., including post-translation modified proteins) in single cells. In one example, an exemplary microfluidic platform herein is configured to conduct a portfolio of customized molecular assays that can detect nucleic acids, proteins, and post-translational modifications in single intact cells with >95% reduction in reagent requirement in under 8 hours (h.).

Accordingly, in a first aspect, the invention features a method for performing multiplexed analysis in a microfluidic device, the method including: (i) loading a test sample portion into a main port of the device, where the device includes a plurality of assay chambers and the main port is configured to deliver the test sample portion to each assay chamber; (ii) capturing the test sample portion within each assay chamber, thereby providing a captured sample portion; (iii) incubating the captured sample portion with a first protein label in each assay chamber, where the first protein label is configured to detect a first target protein (e.g., a cell surface target), thereby providing a labeled sample portion; (iv) treating the labeled sample portion with a fixative reagent in each assay chamber, thereby providing a fixed sample portion; (v) incubating the fixed sample portion with a first nucleic acid label, where the first nucleic acid label is configured to detect a first target nucleic acid, thereby providing a multiplexed-labeled sample portion; (vi) detaching the multiplexed-labeled sample portion, thereby providing a detached sample portion; and (vii) performing an on-chip flow cytometry assay of the detached sample portion, thereby performing multiplexed analysis for the target protein and/or the target nucleic acid.

In some embodiments, the method further includes (e.g., after step (v)) amplifying a signal of the first and/or second nucleic acid label. In further embodiments, the amplifying step includes performing a rolling circle amplification, an isothermal amplification, or any other nucleic acid amplification methodology by providing one or more affinity agents configured to bind to the first and/or second nucleic acid label, one or more proximity ligation probes configured to bind at least one affinity agent, one or more connector probes configured to bind at least one proximity ligation probe and to form a circular template, and/or one or more enzymes configured to generate a concatemer based on the circular template.

In a second aspect, the invention features a method for performing multiplexed analysis in a microfluidic device, the method including: (i) loading a test sample portion into a main port of the device, where the device includes a plurality of assay chambers and the main port is configured to deliver the test sample portion to each assay chamber; (ii) capturing the test sample portion within each assay chamber, thereby providing a captured sample portion; (iii) treating the captured sample portion with a first fixative reagent in each assay chamber, thereby providing a fixed sample portion; (iv) incubating the fixed sample portion with a first protein label in each assay chamber, where the first protein label is configured to detect a first target protein, thereby providing a labeled sample portion; (v) incubating the labeled sample portion with a second protein label in each assay chamber, where the second protein label is configured to detect a second target protein and the second target protein is different than the first target protein, thereby providing a multi-labeled sample portion; (vi) incubating the multi-labeled sample portion with a first nucleic acid label, where the first nucleic acid label is configured to detect a first target nucleic acid, thereby providing a multiplexed-labeled sample portion; (vii) amplifying a signal of the first nucleic acid label, thereby providing an amplified sample portion; (viii) detaching the amplified sample portion, thereby providing a detached sample portion; and (ix) performing an on-chip flow cytometry assay of the detached sample portion, thereby performing multiplexed analysis for the target proteins and the target nucleic acid.

In a third aspect, the invention feature method for performing multiplexed analysis in a microfluidic device, the method including: (i) loading a test sample portion into a main port of the device, where the device includes a plurality of assay chambers and the main port is configured to deliver the test sample portion to each assay chamber; (ii) capturing the test sample portion within each assay chamber, thereby providing a captured sample portion; (iii) incubating the captured sample portion with a first protein label for a cell surface target in each assay chamber, where the first protein label is configured to detect a first target protein, thereby providing a labeled sample portion; (iv) treating the labeled sample portion with a fixative reagent in each assay chamber, thereby providing a fixed sample portion; (v) treating the fixed sample with a permeabilization reagent to provide access to an intracellular target, thereby providing a fixed, permeabilized sample; (vi) treating the fixed, permeabilized sample with one or more target protein labels for detecting one or more intracellular target proteins; (vii) treating the fixed, permeabilized sample (e.g., after step (v) and/or (vi)) with one or more fixative reagents to prepare the sample for nucleic acid hybridization (e.g., where the fixative reagent for step (vii) can be the same or different as the fixative reagent in step (iv)); (viii) incubating the fixed, permeabilized sample (e.g., after step (v), (vi), and/or (vii)) with one or more nucleic acid labels, where the nucleic acid labels are configured to detect a multiple target nucleic acids (e.g., including small RNAs, long RNAs, and DNAs), thereby providing a multiplexed-labeled sample portion; (ix) performing signal amplification using rolling circle polymerase (e.g., to detect rare nucleic acids hybridized to one or more nucleic acid labels or probes); (x) detaching the multiplexed-labeled sample portion (e.g., after step (ix)), thereby providing a detached sample portion; and (xi) performing an on-chip flow cytometry assay of the detached sample portion, thereby performing multiplexed analysis for the target protein and/or the target nucleic acids.

In any method herein, the method further includes (e.g., after step (i) or (ii)) culturing the test sample portion and/or stimulating the test sample portion with a stimulant.

In any method herein, the method further includes (e.g., after step (iii)) incubating the labeled sample portion with a secondary label including a second affinity agent and a detectable marker, where the first and second affinity agents are configured to bind together.

In any method herein, the method further includes (e.g., after step (v)) incubating the multiplexed-labeled sample portion with a secondary label including a second affinity agent, where the first and second affinity agents are configured to bind together.

In any method herein, the method further includes incubating the multiplexed-labeled sample portion with one or more tertiary labels, where each tertiary label is, independently, configured to bind to the second label and independently includes a proximity ligation probe; and/or incubating with one or more quaternary labels, where each quaternary label is, independently, configured to bind to a portion of the proximity ligation probe.

In any method herein, the method further includes (e.g., during or after an incubating step) incubating the fixed sample portion with a second nucleic acid label to detect a second target nucleic acid.

In any method herein, the method further includes treating the captured sample portion, the labeled sample portion, fixed sample portion, and/or multiplexed-labeled sample portion with a fixative reagent, where each fixative reagent can be the same or different.

In any method herein, the method further includes incubating the labeled sample portion with one or more other protein labels (e.g., a second protein label) in each assay chamber, where each protein label is configured, independently, to detect a target protein, thereby providing the labeled sample portion.

In any method herein, the method further includes incubating the captured sample portion, the labeled sample portion, the fixed sample portion, and/or the multiplexed-labeled sample portion with a post-translation modification label (e.g., any herein).

In any method herein, the method further includes treating the multi-labeled sample portion with a second fixative reagent (e.g., where the first and second fixative reagents can be the same or different), thereby providing the multi-labeled sample portion.

In any method herein, the method further includes permeabilizing the labeled sample portion with a permeabilization reagent.

In any method herein, the performing an on-chip flow cytometry assay step includes transporting the detached sample portion to a flow cytometry channel of the device, hydrodynamically focusing the detached sample portion by employing one or more sheath fluids, and detecting one or more protein labels and/or nucleic acid labels by applying an excitation source to the hydrodynamically focused sample portion.

In a fourth aspect, the invention features a microfluidic platform for multiplexed analysis, where the platform includes a microfluidic device, a manifold coupled to the device, a pumping system coupled to the manifold, a controller coupled to the pumping system and configured to control the pumping system, a stage coupled to the device, an excitation source configured to provide an excitation energy to the flow cytometry channel, and a detector configured to receive an emission spectrum from an excited label within the device.

In some embodiments, the microfluidic device includes a plurality of assay chambers, where each assay chamber is configured to conduct a multiplexed series of assays and each assay chamber is individually addressable; a main port in fluidic communication with each assay chamber, where the main port is configured to deliver a test sample portion to each assay chamber; a plurality of ports, where each assay chamber is in fluidic communication with at least one port; a flow cytometry channel in fluidic communication with each assay chamber, where the flow cytometry channel is configured to hydrodynamically focus the test sample portion; and one or more sheath ports in fluidic communication with the flow cytometry channel, where the sheath port is configured to deliver a sheath fluid to the flow cytometry channel.

In some embodiments, the manifold includes a first reservoir configured to contain the test sample portion, where the first reservoir is in fluidic communication with the main port; a second reservoir configured to contain a first protein label, where the second reservoir is in fluidic communication with at least one port or the main port and where the first protein label is configured to detect a first target protein; a third reservoir configured to contain a first fixative reagent, where the third reservoir is in fluidic communication at least one port or the main port; a fourth reservoir configured to contain a first nucleic acid label, where the fourth reservoir is in fluidic communication with at least one port or the main port and where the first nucleic acid label is configured to detect a first target nucleic acid; and a fifth reservoir configured to contain one or more sheath fluids, where the fifth reservoir is in fluidic communication with the sheath port. In further embodiments, the manifold further includes a sixth reservoir configured to contain one or more amplification reagents, where the sixth reservoir is in fluidic communication with at least one port or the main port and where the one or more amplification reagents are configured to amplify a signal of the first nucleic acid label.

In some embodiments, the manifold further includes one or more valves (e.g., a valve disposed between the first reservoir and the main port; and/or a valve disposed between each reservoir and the port in fluidic communication with each reservoir). In other embodiments, the controller is further configured to operate the valve.

In some embodiments, the pumping system is coupled to the first, second, third, fourth, and fifth reservoirs. In other embodiments, the pumping system further includes a pressure source and a pressure controller configured to be controlled by the controller.

In some embodiments, the controller is configured to execute any method herein. In one embodiment, the controller is configured to execute the following: fluidically deliver the test sample portion from the first reservoir to the main port and then to each assay chamber; fluidically deliver the first protein label from the second reservoir to at least one assay chamber, thereby providing a labeled sample portion; fluidically deliver the first fixative reagent from the third reservoir to at least one assay chamber containing the labeled sample portion, thereby providing a fixed sample portion; fluidically deliver the first nucleic acid label from the fourth reservoir to at least one assay chamber containing the fixed sample portion, thereby providing a multi-labeled sample portion; fluidically deliver the multi-labeled sample portion(s) from at least one assay chamber to the flow cytometry channel; and fluidically deliver one or more sheath fluids from the fifth reservoir to the sheath port. In further embodiments, the controller is further configured to fluidically deliver the one or more amplification reagents to the multi-labeled sample portion prior to the multi-labeled sample portion being delivered to the flow cytometry channel.

In some embodiments, the stage is configured to control a temperature within the plurality of assay chambers.

In some embodiments, the excitation source is configured to excite one or more labels (e.g., the first protein label, the first nucleic acid label, or a secondary label configured to directly or indirectly bind to the first protein label or the first nucleic label), thereby providing an excited label for the multi-labeled sample portion.

In any embodiment herein, the first protein label and/or the first nucleic acid label further includes a detectable marker. In some embodiments, the first protein label further includes a first affinity agent. In other embodiments, the first nucleic acid label further includes a first affinity agent.

In any embodiment herein, each of the first and nucleic acid labels includes, independently, a nucleic acid-binding region configured to detect the target nucleic acid and one or more affinity agents.

In any embodiment herein, the first target protein is a cell surface protein, and the second target protein is an intercellular protein.

In any embodiment herein, the fixative reagent includes formaldehyde, paraformaldehyde, glutaraldehyde, 1-ethyl-3-(3-dimethylaminopropyl)carbodiimide (EDC), dicyclohexylcarbodiimide (DCC), N-hydroxysuccinimide (NHS), and/or N-hydroxysulfosuccinimide (sulfo-NHS), as well as any other described herein.

Definitions

As used herein, the term "about" means+/−10% of any recited value. As used herein, this term modifies any recited value, range of values, or endpoints of one or more ranges.

By "binding" is meant having a covalent or a non-covalent bond, such as one or more of electrostatic, ionic, hydrogen, van der Waals, π-effect, π-bonding, or hydrophobic bonds.

By "coupled" is meant indirect or direct contact between two or more components or structures, thereby allowing at least two components to interact. In particular embodiment, two or more components are coupled in a reversible manner.

By "chamber" is meant a two-dimensional or three-dimensional region of the microfluidic device configured to confine a fluid (e.g., a gas, a liquid, a colloid, a solution, etc.). This region may be enclosed within a substrate and include one or more ports or channels in fluidic communication with that region. Alternatively, the region can have an open format and may not be enclosed. The chamber can have any useful configuration (e.g., a channel, a well, a tube, a pipe, etc.) and dimension (e.g., a microchamber or nanochamber, including microchannels, nanochannels, microwell, and nanowells) having one or more optional ports.

By "fluidic communication," as used herein, refers to any duct, channel, tube, pipe, chamber, or pathway through which a substance, such as a liquid, gas, or solid may pass substantially unrestricted when the pathway is open. When the pathway is closed, the substance is substantially restricted from passing through. Typically, limited diffusion of a substance through the material of a plate, base, and/or a substrate, which may or may not occur depending on the compositions of the substance and materials, does not constitute fluidic communication.

By "microfluidic" or "micro" is meant having at least one dimension that is less than 1 mm. For instance, a microfluidic structure (e.g., any structure described herein) can have a length, width, height, cross-sectional dimension, circumference, radius (e.g., external or internal radius), or diameter that is less than 1 mm.

By "protein" is meant a polymer of two or more amino acids (natural, unnatural, or modified amino acids) linked together. As used herein, "protein" is used interchangeably with "polypeptide" and "peptide."

By "nucleic acid" is meant a polymer of two or more nucleotides. As used herein, a "nucleic acid" is used interchangeably with "polynucleotide." Exemplary nucleic acids include, but are not limited to, ribonucleic acids (RNAs) (e.g., a messenger RNA (mRNA), a micro RNA (miRNA), a long noncoding RNA (lncRNA or lincRNA), a small nucleolar RNA (sno-RNA), a small interfering RNA (siRNA), or a Piwi-interacting RNA (piRNA), or portions thereof); deoxyribonucleic acids (DNAs); threose nucleic acids (TNAs); glycol nucleic acids (GNAs); peptide nucleic acids (PNAs); locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization); or hybrids thereof. In particular embodiments, the nucleic acid or nucleic acid sequence selectively hybridize to another nucleic acid sequence. Such specific hybridization can include, e.g., binding, duplexing, or hybridizing of a nucleic acid preferentially to a particular nucleic acid sequence under stringent conditions when that sequence is present in a complex mixture (e.g., total cellular) of nucleic acids (e.g., DNA and/or RNA mixtures). In some embodiments, stringent conditions refer to conditions under which a probe will hybridize preferentially to its target sequence, and to a lesser extent to, or not at all to, other sequences. Exemplary, non-limiting stringent conditions include highly stringent hybridization and wash conditions that are selected to be about 5° C. lower than the thermal melting point ($T_m$) for the specific sequence at a defined ionic strength and pH, where $T_m$ is the temperature (under defined ionic strength and pH) at which 50% of the target sequence hybridizes to a perfectly matched probe, such as wash conditions of 0.15 M NaCl at 72° C. for about 15 min.; 0.2×SSC at 65° C. for 15 min.;

1×SSC wash at 45° C. for 15 min.; and/or 4-6×SSC at 40° C. for 15 min., where these washes can be combined in any useful sequence.

As used herein, the terms "top," "bottom," "upper," "lower," "above," and "below" are used to provide a relative relationship between structures. The use of these terms does not indicate or require that a particular structure must be located at a particular location in the apparatus.

Other features and advantages of the invention will be apparent from the following description and the claims.

BRIEF DESCRIPTION OF THE DRAWINGS

FIG. 2A-2D provides photographs of (A) an exemplary microfluidic device; (B) a device coupled to a stage and in fluidic communication with a manifold; (C) a platform including various controllers, pumps, and valves; and (D) the optical detector and excitation source pathway for the platform.

DETAILED DESCRIPTION OF THE INVENTION

The present invention relates to microfluidic devices and platforms configured to perform multiplexed analysis with a single-cell resolution. In particular, distinct levels of various nucleic acids (e.g., mRNA, DNA, miRNA, etc.) and proteins (e.g., cell surface proteins, intracellular proteins, and/or post-translation modified proteins) can be detected in each single, intact cell. This capability is facilitated by a microfluidic device configured to capture and assay individual cells, and then to detect target levels using an on-chip flow cytometry channel.

In addition, the present invention relates to methods for performing multiplexed analysis. In particular, the methods herein employ one or more fixative reagents to affix and retain nucleic acid targets within the cell, thereby allowing multiplexed detection of desired protein and nucleic acid targets within the same cell. Additional details follow.

Microfluidic Device

The present invention includes a microfluidic device configured to perform a multiplexed series of assays on a sample, to deliver one or more reagents to designated chambers on the device in a controlled manner, to hydrodynamically focus sample portions, and to optically detect target nucleic acids and proteins. All of these functionalities can be performed on-chip (i.e., within the device) and in an automated manner.

Figure 1A:
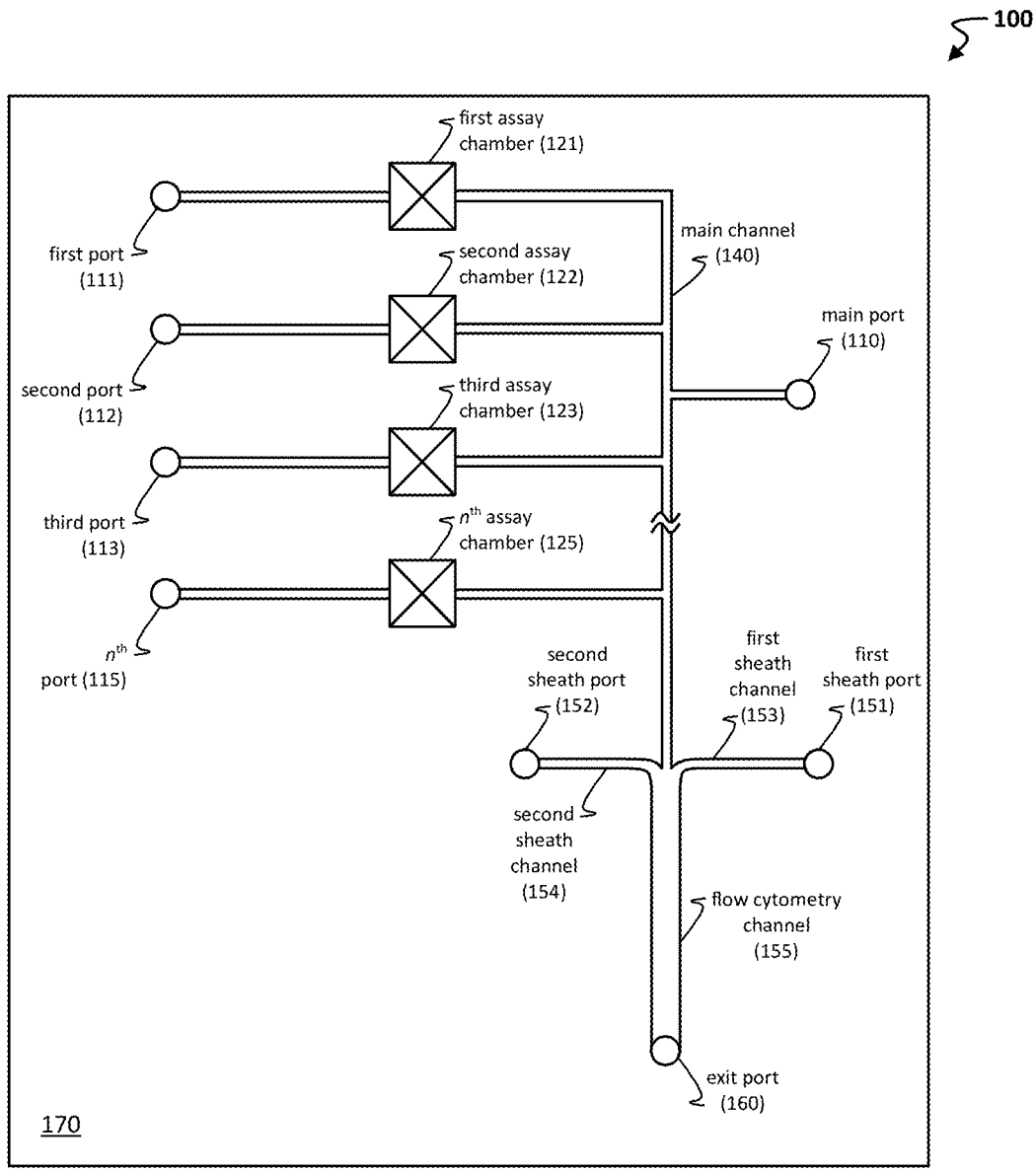
FIG. 1A-1C provides exemplary schematics of a microfluidic device 100 and microfluidic platforms 1000, 1100.

As seen in FIG. 1A, an exemplary microfluidic device 100 includes a plurality of assay chambers 121-123, 125, where each assay chamber is individually addressable. The device 100 can include any useful n number of chambers, where n can be of from 1 to about 5000. The assay chambers 121-123, 125 are provided to contain a volume of a sample fluid having targets of interest (e.g., any target herein). As will be described further below, labels, fixative reagents, amplification reagents, stimulants, stains, buffers, and other reagents, may be introduced to the microfluidic device 100 and interact with the targets in the assay chambers 121-123, 125.

The device can include any useful type of chamber, e.g., an assay chamber configured to conduct a multiplexed series of assays; a sample chamber for receiving and/or storing a test sample; an incubation chamber for incubating a test sample or a portion thereof (i.e., a sample portion); a reagent chamber configured to store or transport one or more reagents; a wash chamber configured to maintain a sample portion for one or more washes; a capture chamber configured to physically capture one or more sample portions on a wall of the chamber (e.g., a wall treated with a capture reagent); a sterilization chamber containing one or more reagents to sterilize or disinfect the test sample; a permeabilization chamber containing one or more reagents to permeabilize a cell in the test sample; a fixation chamber containing one or more fixative reagents to fix a cell in the test sample; and/or a waste chamber for storing one or more by-products of the assay. Each of these chambers can be interconnected by a valve, a port, and/or a channel that can optionally include a valve in its fluidic path. Alternatively, the same chamber (e.g., the assay chamber) can be configured to perform multiple functions (e.g., capture, stimulate, fix, permeabilize, label, release, incubate, etc. a sample portion).

The chambers can have any useful dimension, geometry, and/or configuration. For instance, the chambers can have any useful cross-sectional dimension, such as a length, depth, width, diameter, and/or major axis of from about 1 μm to about 1 cm (e.g., of from 1 μm to 1 mm, 1 μm to 500 μm, 1 μm to 300 μm, 10 μm to 500 μm, 10 μm to 300 μm, 50 μm to 500 μm, 50 μm to 300 μm, 100 μm to 1 mm, or 100 μm to 500 μm). In other embodiments, the length of the chambers (e.g., microchannels) is of from 10 μm to about 10 cm (e.g., from 100 μm to 1 cm). The chambers can have any useful geometry, such as a rectangular, square, circular, trapezoidal, U-shaped, etc. cross-section. Furthermore, the chamber can be configured as a well or a channel connected to one or more other chambers.

In some embodiments, the width and depth of the chamber (e.g., microchannel) are generally selected to obtain the desired flow characteristics in the chamber and provide sufficient volume for the amount of sample or particles to be received by the chamber. Generally, the length of the chamber (e.g., microchannel) is selected to route fluid the appropriate distance between ports and chambers, for example. While example dimensions of channels have been provided herein for reference, other dimensions may be used in other embodiments.

The device can include any useful type and number of structures (e.g., chambers, channels, wells, ports, etc.) to perform the desired multiplexed reactions and/or to establish the desired fluidic pathway. FIG. 1A shows an exemplary fluidic network to effect a multiplexed network. The fluidic network is defined within a substrate 170 and includes one or more assay chambers 121-123, 125 connected to a main channel 140. This main channel 140, in turn, is connected to a main port 110. This fluidic layout is particularly beneficial to distribute the same substance to all chambers. For instance, the test sample can be delivered to the main port 110 and transported through the main channel 140 to equally distribute or aliquot a test sample portion into each assay chamber 121-123, 125. By maintaining an equal pressure difference between the main port 110 and the other ports 111-113, 115, an equal amount of the test sample can be distributed into each assay chamber 121-123, 125.

The device can include one or more ports 111-113, 115 in fluidic communication with one or more assay chambers 121-123, 125. As can be seen, the first port 111 is most directly connected to the first assay chamber 121. In this fluidic network, opening and closing the first port 111 (or the valve or fluidic connector that is connected to the first port 111) can control flow and transport through the first chamber 121. For instance, by closing all ports and then opening the main port 110 and the first port 111, a fluidic pathway is established between the main port 110 and the first port 111 (i.e., through the main channel 140 and the first assay chamber 121) but all other fluidic pathways are closed, thereby facilitating transport of a substance only to the first assay chamber 121. In a similar manner, fluidic pathways and fluid transport can be controlled between any of the chambers 121-123, 125 and ports 110-113, 115, 160. For instance, the second port 112 is most directly connected to the second assay chamber 122, the third port 113 to the third assay chamber 123, and the $n^{th}$ port 115 to the $n^{th}$ chamber 125.

The device can include an on-chip flow cytometry module. In one instance, the on-chip flow cytometry module includes one or more flow cytometry channels facilitated to focus a desired sample portion through a detection area, as well as one or more sheath channels. As can be seen in FIG. 1A, the device can include a flow cytometry channel 155 that is configured to contain flow of a sheath fluid from first and second sheath ports 151, 152. Connecting the sheath port 151, 152 to the flow cytometry channel 155 is the sheath channel 153, 154. Alternatively, only one sheath port can be present but configured to be in fluidic communication with two sheath channels, where one sheath channel is disposed to the right of the flow cytometry channel and the other sheath channel is disposed to the left of the flow cytometry channel. Any useful configuration of sheath port(s), sheath channel(s), and flow cytometry channel(s) can be employed. Additional details on the module, including excitation sources and detectors, are described herein.

The flow cytometry channel 155 is in fluidic communication with the main channel 140 and an exit port 160. In this manner, the main channel 140 provides a fluidic pathway between each assay chamber 121-123, 125 and the flow cytometry channel 155. As each assay chamber is individually addressable, individual fluidic pathways can be established between the assay chamber and the flow cytometry channel, thereby allowing each sample portion to be analyzed on an individual basis by the on-chip flow cytometry module.

The device can include one or more ports to provide fluidic access to the microfluidic device. In particular, such ports can be in fluidic communication with a sample reservoir or a reagent reservoir in a manifold in order to deliver sample portions and reagents to the device (e.g., by way of one or more fluidic connections and/or connectors, as described herein). Any useful number of ports may be present to facilitate fluid access to and from the microfluidic device at desired locations. Each port may be useful as an inlet, an outlet, or a combination of inlets and outlets depending on the fluidic pathway being established on-chip. The ports can have any useful dimension, such as from about 100 µm to about 2 (e.g., a cross-sectional dimension, such as a length, width, major axis, or diameter of about 500 µm).

The device may be fabricated from any useful material and employing any useful methodology. For instance, the substrate can include, e.g., quartz, glass, polycarbonate, fused-silica, poly(dimethyl siloxane), a polymer, a metal, a semiconductor, or a transparent substrate, as well as composites and multi-layered, laminated, or bonded forms thereof. Exemplary methods of fabrication include rapid prototyping, microfabrication (e.g., by casting, injection molding, compression molding, embossing, ablation, thin-film deposition, and/or Computer Numerically Controlled (CNC) micromachining), photolithography, etching techniques (e.g., wet chemical etching, reactive ion etching, inductively coupled plasma deep silicon etching, laser ablation, or air abrasion techniques), methods for integrating these structures into high-throughput analysis equipment (e.g., integration with a microplate reader or a control instrument, such as a computer), methods for fabricating and integrating valves (e.g., one or more pneumatic valves), methods for integrating structures with a transducer array, methods for modifying surfaces (e.g., by including a layer of extracellular matrix components, such as with a protein solution (e.g., Cell-Tak™, as described herein), fibronectin (FN), laminin, Matrigel™, and/or RGD peptide, or by including a layer of a globulin protein, such as albumin or an immunoglobulin), methods for including one or more capture arrays (e.g., a capture array including one or more capture agents provided in a high-density array on a substrate), and methods for providing vias or inlets (e.g., by piercing, drilling, ablating, or laser cutting), such as those described in U.S. Pat. No. 8,257,964; and U.S. Pub. Nos. 2012/0231976, 2012/0214189, 2011/0129850, 2009/0251155, and 2009/0036324, each of which is incorporated herein by reference in its entirety.

On-Chip Flow Cytometry Module

The present invention includes a device having an on-chip flow cytometry module. The module includes one or more structures to hydrodynamically focus a sample portion. In addition, the module can be used with one or more excitation sources and detectors to detect one or more detectable labels.

As seen in FIG. 1A, the device 100 includes a flow cytometry channel 155 located downstream of the assay chambers 121-123, 125. In use, a sample portion containing labeled targets can be transported from the assay chamber towards the flow cytometry channel. A flow cytometry buffer solution (or sheath fluid) is then transported through the sheath channel 153, 154 from the sheath port 151, 152. The sheath solution hydrodynamically focuses the target (e.g., one or more labeled targets located on or within an intact cell from the test sample) as the flow of sheath fluid meets the flow of sample fluid from the assays chambers. Additional ports may present to produce multidirectional and more efficient hydrodynamic focusing of the target. The hydrodynamically focused targets may then be analyzed by flow cytometry excitation energy sources and detectors positioned to analyze particles in the flow cytometry channel 155.

The sheath fluid can be any useful fluid that does not detrimentally affect the sample portion. For instance, when the sample portion includes one or more intact cells, then the sheath fluid can be an isotonic, buffered solution capable of maintaining cell viability or integrity (e.g., any buffer herein, such as a phosphate buffered saline (PBS), a tris(hydroxymethyl) aminomethane (Tris) buffer, a Tris-buffered saline (TBS), a Tris/sucrose/ethylenediamine tetraacetic acid solution (TSE), etc.). In addition, the sheath fluid should be capable of hydrodynamically focusing a sample portion. Throughput of the sample portion through the flow cytometry channel may be related to the degree of hydrodynamic focusing and size of the flow cytometry channel. In one example, a 10:1 focusing ratio can provide a throughput of around 100 cells per minute. Additional methods of configuring appropriate flow rates to establish hydrodynamic are described herein, as well as in Liu P et al., "Microfluidic fluorescence in situ hybridization and flow cytometry (µFlowFISH)," *Lab Chip* 2011 Aug. 21; 11(16):2673-9; and Perroud T D et al., "Microfluidic-based cell sorting of *Francisella tularensis* infected macrophages using optical for Platform The platform of the invention includes a microfluidic device (e.g., any herein), as well as one or more components configured to provide one or more samples or reagents on-chip (e.g., by use of a manifold, a pumping system, and/or a controller) and to detect one or more labeled targets (e.g., by use of an excitation source, a detector, and/or a controller).

Figure 1B:
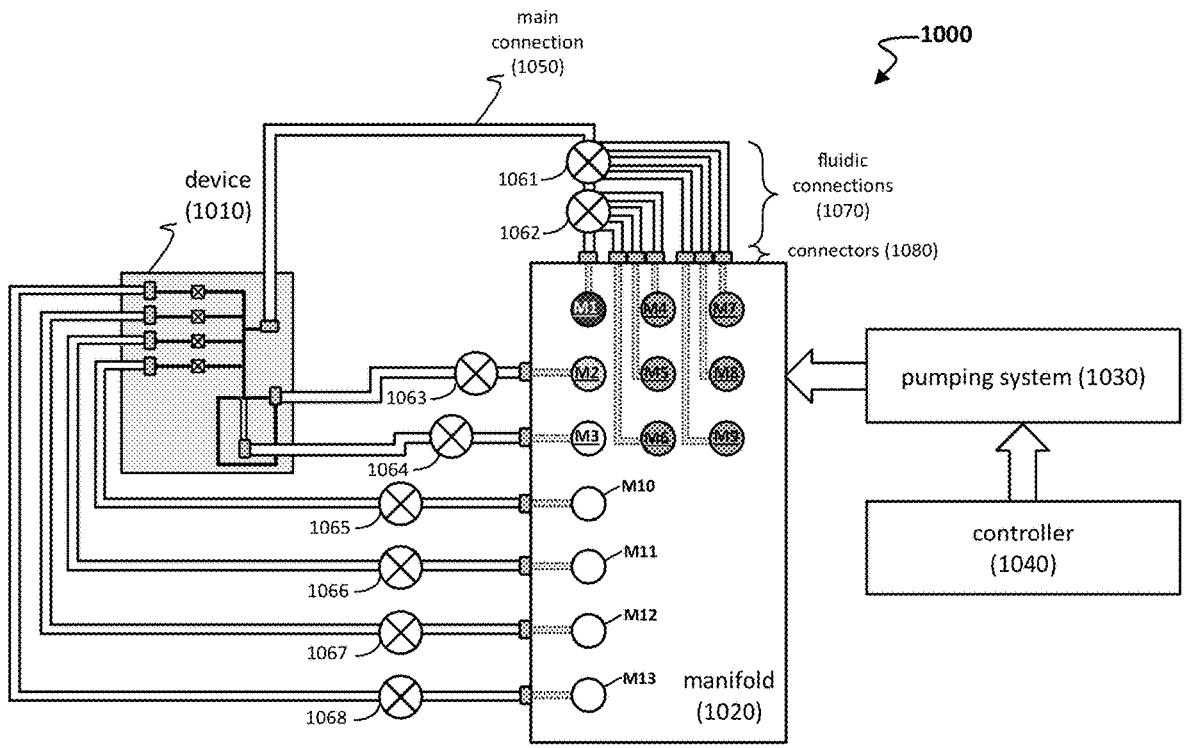

FIG. 1B provides an exemplary platform 1000 including a microfluidic device 1010, a manifold 1020, a pumping system 1030, and a controller 1040. As can be seen, the device 1010 is in fluidic communication with the manifold 1020. The pumping system 1030 is configured to transport a reagent or a sample from the manifold 1020 and into the device 1010. Finally, a controller 1040 controls the manifold 1020, the pumping system 1030, as well as any other component capable of being electronically controlled (e.g., one or more pressure sensors, pressure valves, etc.). Each of these components is detailed below.

The manifold 1020 can include one or more reservoirs M1-M13 configured to store one or more agents or fluids, such as samples, reagents, sheath fluid, waste, etc. Each reservoir includes an outlet configured to interface with a connector 1080 (e.g., a fitting, a luer lock, a ferrule, a nut, an o-ring, a Y-connector, a T-connector, etc., optionally including a gasket and/or a frit) and/or a fluidic connection 1070 (e.g., a tubing, optionally including an in-line filter, column, etc.). The connector provides a tight, leak-proof connection between the reservoir and the tubing, whereas the fluidic connection contains and transports the agent to a port of the microfluidic device. In some embodiments, the diameter of the fluidic connection may be selected to reduce cell loss by axial dispersion in the tubing (e.g., a diameter less than about 500 µm) and to reduce cell adhesion (e.g., a PEEK tubing or a PTFE tubing). Connectors can be present on the device (at one or more ports) and the manifold (at one or more outlets).

Any useful fluidic pathway can be adapted to effectively deliver agents from the manifold to the device. For instance, the manifold 1020 can include a reservoir M1 configured to contain the sample and additional reservoirs M4-M9 configured to contain a reagent (e.g., a protein label, a fixative reagent, a nucleic acid label, wash buffers, etc.). Each of these reservoirs can be connected to a fluidic connection 1070. These fluidic connections 1070 can be combined to form a main connection 1050, where the desired agent can be delivered on-chip by use of one or valves 1061, 1062 (e.g., multi-port valves, an autosampler, etc.). In another instance, the manifold 1020 can include a reservoir M2 configured to contain a sheath fluid, which in turn is connected to the sheath channel of the device 1010 by way of a fluidic connection having a valve 1063. In yet another instance, the manifold 1020 can include a reservoir M3 configured to collect the analyzed sample portions or waste that is transported from the exit port of the device by way of a fluidic connection having a valve 1064.

A reservoir can be optionally connected to each port that is closest to an assay chamber. For example, the manifold can include a plurality of reservoirs M10-M13, and each reservoir can be connected to a separate port of the device 1010 by way of a fluidic connection having a valve 1065-1068. A skilled artisan would understand that any useful configuration of fluidic connections can be employed to direct agents from the manifold to the device, as well as any useful routines to control pressure or flow of these agents through the fluidic connections. For instance, the manifold 1020 can be coupled to a pumping system 1030, which is then coupled to each reservoir and configured to individually control pump rates, flow rates, displacement rates, and/or pressure of the agent through the device. The pumping system can include one or more electronic pressure pumps coupled to an inert gas supply (e.g., a nitrogen gas supply) in order to generate pressure to be applied by the electronic pressure pumps. In some examples, pressures may be applied up to about 5 psi. Higher or lower pressures may also be applied.

One or more controllers can be employed to control the pumping system, the valves, etc. For instance, a controller 1040 can be coupled the pumping system 1030 and configured to control the pumping system 1030 (e.g., by executing any useful pumping routine). For instance, the controller can be configured to fluidically deliver a particular agent into a particular chamber to perform a multiplexed assay. The controller can be configured to fluidically deliver an agent by applying a control signal to the appropriate valve to open or close that valve. By applying such signals in an appropriate sequence, the desired fluidic pathway can be established.

Using the device in FIG. 1A and the platform in FIG. 1B as an example, the controller 1040 can be configured to fluidically deliver a test sample portion from a first reservoir M1 to the main port 110 and then to each assay chamber 121-123, 125, thereby providing a sample portion in each assay chamber. The desired fluidic pathway (i.e., from the first reservoir M1 to each assay chamber 121-123, 125) can be established by first providing a control signal to valves 1061, 1062 to open the connection between the first reservoir M1 and the main connection 1050. As can be seen, this main connection 1050 is connected to the main port 110 of the device 1010, 100. To establish flow to the assay chambers, a pressure gradient should be generated between the main port 110 and the ports 111-113, 115 located near the assay chambers. The pressure gradient can be established by the controller, e.g., by providing a control signal to valves 1065-1068 to open the connection between the ports 111-113, 115 of the device 100 and the reservoirs M10-M13 in the manifold 1020. In this manner, the appropriate fluidic pathway has been established (e.g., from reservoir M1; through the main connection 1050; to the main port 110; continuing through the main channel 140; into each assay chamber 121-123, 125; out through each port 111-113, 115; and then finally into each holding reservoir M10-M13).

Fluid flow can begin by applying pressure to the appropriate reservoir M1 in the manifold, where this pressure will transport the sample in that reservoir along the established fluidic pathway. The controller can be programmed to apply pressure driven flow in this configuration for a predetermined amount of time (a sample loading time). In a similar manner, other agents can be delivered from a reservoir to any desired chamber(s) of the device.

The controller 1040 can be configured to provide one or more labels for the desired target(s), such as by being configured to fluidically deliver a protein label from a second reservoir M4 to at least one assay chamber 121-123, 125, thereby providing a labeled sample portion; fluidically deliver a fixative reagent from a third reservoir M5 to at least one assay chamber (e.g., chamber 121) containing the labeled sample portion, thereby providing a fixed sample portion; and fluidically deliver a nucleic acid label from a fourth reservoir M6 to at least one assay chamber (e.g., chamber 121) containing the fixed sample portion, thereby providing a multi-labeled sample portion. Finally, the controller 1040 can be configured for on-chip flow cytometry analysis, such as by being configured to fluidically deliver the multi-labeled sample portion(s) from at least one assay chamber 121-123, 125 to a flow cytometry channel 155; and fluidically deliver one or more sheath fluids from a fifth reservoir M2 to the sheath port 151. In this manner, the controller can be configured to perform any useful routine for preparing, incubating, and detecting sample portions, where each individual, single cell is tested in a multiplexed manner.

Figure 1C:
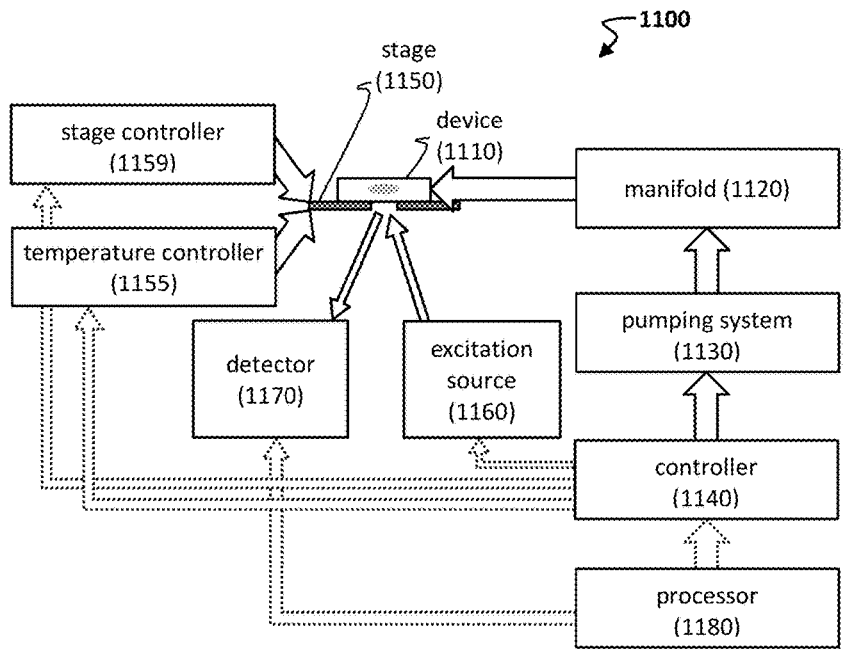

The platform can include any other useful components. As seen in FIG. 1C, the platform 1100 can include a device 1110 positioned on a stage 1150, a manifold 1120 configured to deliver one or more agents, a pumping system 1130 coupled to the manifold 1120, as well as an excitation source 1160 and a detector 1170 aligned with a detection area of the device (gray area in device 1110). The stage 1150 can optionally be coupled to a stage controller 1159 (e.g., to control stage movement) and a temperature controller 1155 (e.g., to control a heater or cooler located on or near the stage). As described herein, the controller 1140 can be configured to control the pumping system 1130 and can optionally serve as an integration hub configured to control other components, such as the excitation source 1160, the detector 1170, the stage controller 1159, and the temperature controller 1155. The controller 1140, in turn, can be coupled to a processor 1180. The processor 1180 can be configured to receive detection signals from the flow cytometry detectors and/or to process the detection signals, e.g., by fitting peaks to the detection signal, identifying peak locations, and/or generating population histograms. In this manner, the methods of the invention can be automated by using such a platform.

FIG. 2A-2D provides photographs of an exemplary platform. Provided are photographs of the device (FIG. 2A-2B), the platform components (FIG. 2C), and the optical laser pathway (FIG. 2D).

Figure 3A:
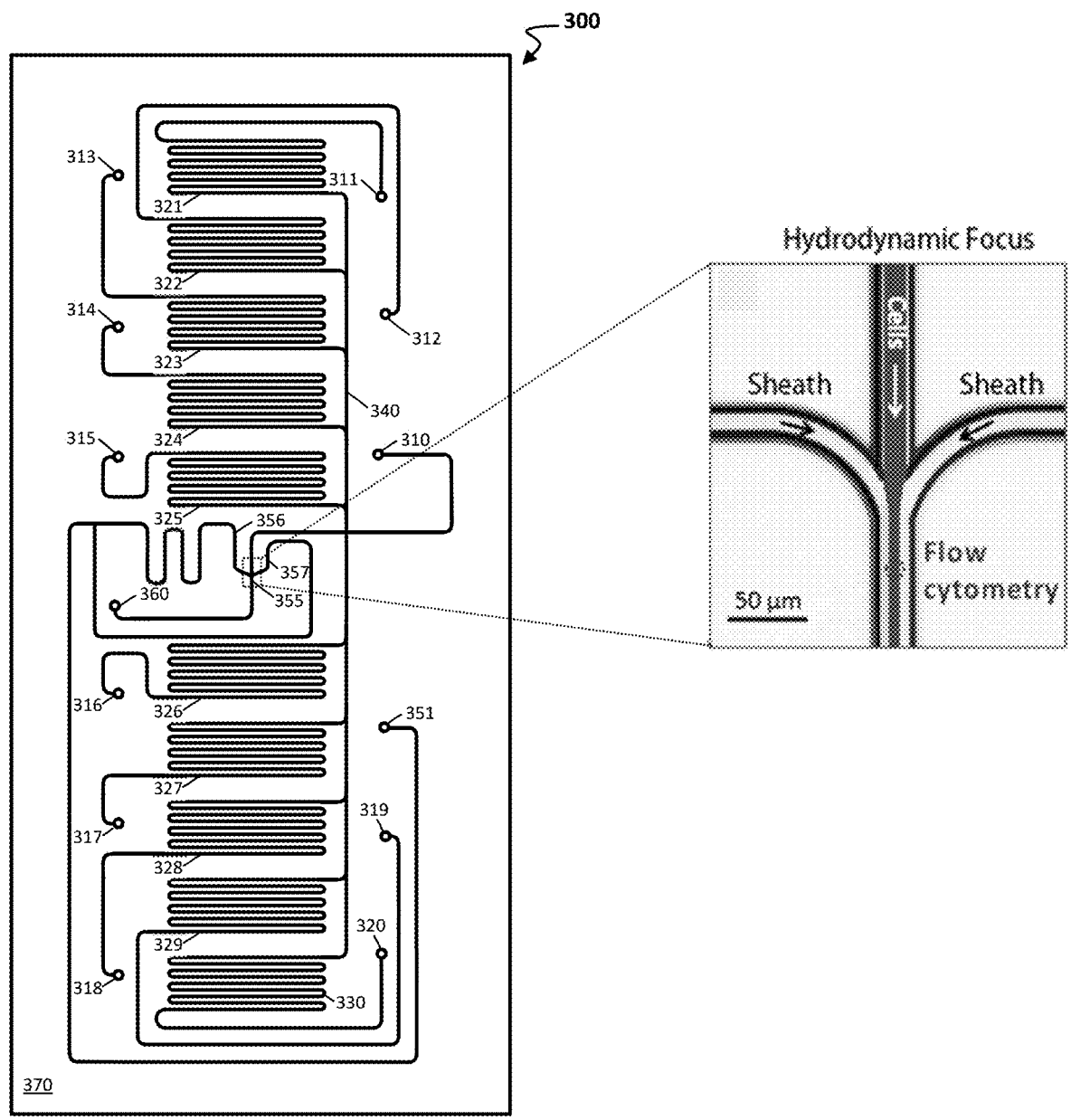
FIG. 3A-3C provides exemplary devices and platforms. Shown are (A) an exemplary schematic of a ten-chamber microfluidic device 300 (left) and a microphotograph of the flow cytometry region (right), in which cells prepared in each of the assay chambers can be detached and driven to the center of the chip for hydrodynamic focus and flow cytometry; (B) an exemplary schematic of a platform 3000; and (C) an exemplary schematic of an optical system for detection 3100.
Figure 3B:
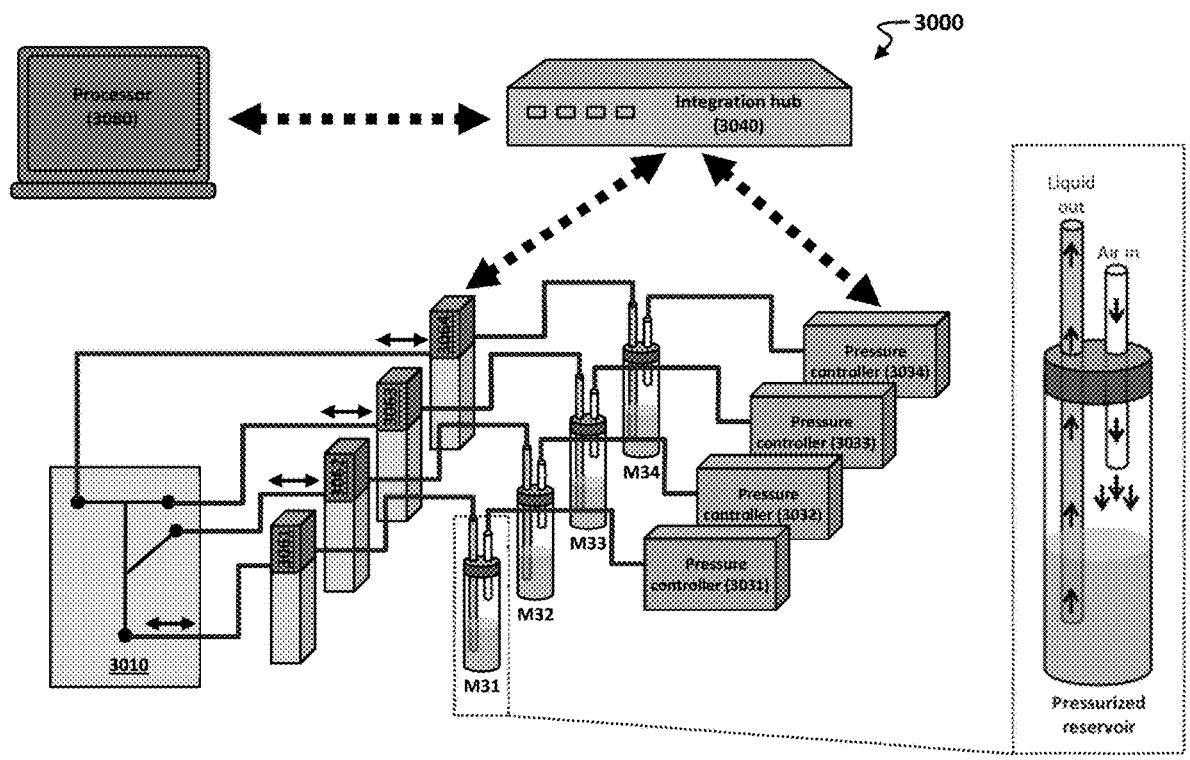
Figure 3C:
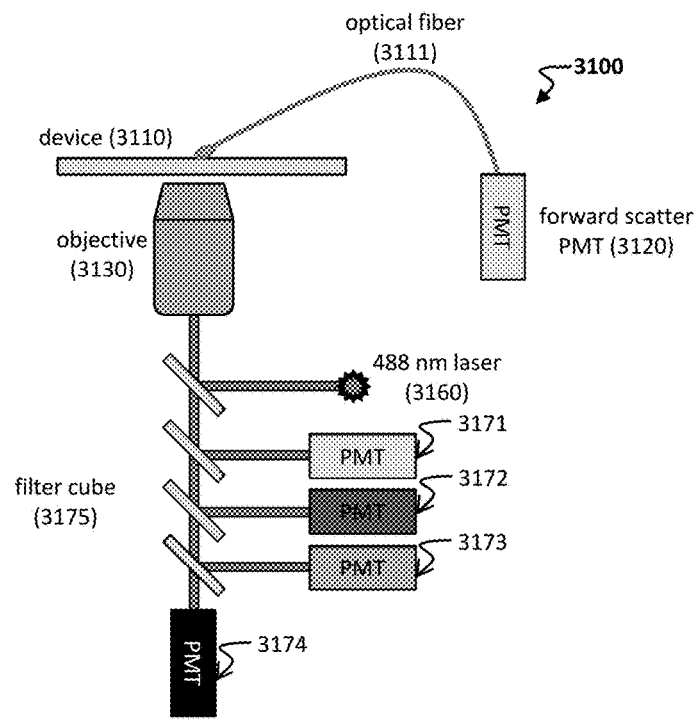

FIG. 3A-3C provides another exemplary platform. Provided is a schematic of a microfluidic device 300 having a main port 310 and an exit port 360 in a substrate 370 (FIG. 3A) The device 300 includes a plurality of chambers 321-330, where each chamber is in fluidic communication with a port 311-320. The flow cytometry channel 355 is in fluidic communication with the main channel 340. Sheath channels 356, 367 are located on each side of the flow cytometry channel 355 and connected by one sheath port 351, where the sheath channels 356, 367 are configured to hydrodynamically focus a sample portion in the flow cytometry channel 355. As shown in the inset of FIG. 3A, the microphotograph shows the junction between the sheath channels 356, 367 and the flow cytometry channel 355 and the detection area (dashed circle) within the flow cytometry channel 355.

FIG. 3B shows the pumping scheme 3000 including a device 3010 that is in fluidic communication with fluidic connections having valves 3061-3064. Each fluidic connection, in turn, is coupled to a pressurized reservoir M31-M34 that is individually controlled by a pressure controller 3031-3034. A processor 3080 and an integration hub 3040 can be configured to control the valves 3061-3064 and pressure controllers 3031-3034.

FIG. 3C shows the detection scheme 3100 including a device 3110 aligned with an optical fiber 3111 coupled to a forward scatter detector 3120 (e.g., a PMT, such as to observe sample portions in the assay chamber). Also provided are components to detect fluorescence signals during flow cytometry analysis. These components include an objective 3130 aligned to the flow cytometry channel of the device 3110, an excitation source 3160 (e.g., a laser source having the desired excitation wavelength, such as 488 nm), a filter cube 3175, and a plurality of detectors 3171-3174 (e.g., PMTs configured to detect a particular wavelength or wavelength range).

The device and platform can include any other useful structures or components, such as one or more pre-concentrator channels (e.g., as described in U.S. Pat. No. 7,828,948, which is incorporated herein by reference in its entirety); optical tweezers (e.g., as described in Perroud T D et al., *Anal. Chem.* 2008 Aug. 15; 80(16):6365-72, which is incorporated herein by reference in its entirety); micropores (e.g., as described in Perroud T D et al., "Isotropically etched radial micropore for cell concentration, immobilization, and picodroplet generation," *Lab Chip* 2009 Feb. 21; 9(4):507-15, which is incorporated herein by reference in its entirety); LNA flow-FISH components (e.g., as described in Wu M et al., "miRNA detection at single-cell resolution using microfluidic LNA flow-FISH," *Methods Mol. Biol.* 2014; 1211: 245-60; Liu P et al., *Lab Chip* 2011 Aug. 21; 11(16):2673-9; and Wu M et al., "Single-cell protein analysis," *Curr. Opin. Biotechnol.* 2012 February; 23(1):83-8, each of which is incorporated herein by reference in its entirety); separation/extraction components (e.g., filters, posts, membranes, weirs (optionally including beads), matrices, or high voltage electrodes for performing on-chip capillary electrophoresis separations); heating components (e.g., electrodes, resistive heaters, heated stages, or filaments); pumps (e.g., active or passive pumps, such as an electric pump or a low flow rate peristaltic pump or application of negative pressure, such as by actuating a valve); a membrane (e.g., placed within a channel and/or a chamber); a multifunctional sensor (e.g., to measure temperature, strain, and electrophysiological signals, such as by using amplified sensor electrodes that incorporate silicon metal oxide semiconductor field effect transistors (MOSFETs), a feedback resistor, and a sensor electrode in any useful design, such as a filamentary serpentine design); a microscale light-emitting diode (LEDs, such as for optical characterization of the test sample); an active/passive circuit element (e.g., such as transistors, diodes, and resistors); an actuator; a wireless power coil; a device for radio frequency (RF) communications (e.g., such as high-frequency inductors, capacitors, oscillators, and antennae); a resistance-based temperature sensor; a photodetector; a photovoltaic cell; a diode; one or more components to operate a transducer, such as a power source to operate an electrode; a data-processing circuit powered by the power source and electrically connected to the transducer (e.g., a counter electrode, a reference electrode, and at least one said working electrode); and/or one or more components for autonomous remote monitoring of a sample, such as an analog-to-digital converter, a radiofrequency module, and/or a telemetry unit (e.g., configured to receive processed data from a data-processing circuit electrically connected to the detection component and to transmit the data wirelessly).

Methods for Performing Multiplexed Analysis

The present invention also includes methods for performing multiplexed analysis. In particular embodiments, the method includes use of a device and/or a platform described herein. In yet other embodiments, the methods herein allow for single-cell analysis of a sample portion while minimizing sample consumption and reducing complicated, manual fluid handling procedures. Rather, the methods herein employ a microfluidic device to contain and control reactions of small volumes (e.g., nanoliter- or picoliter-scale volumes) and an automated platform to execute fluid handling protocols.

Figure 9:
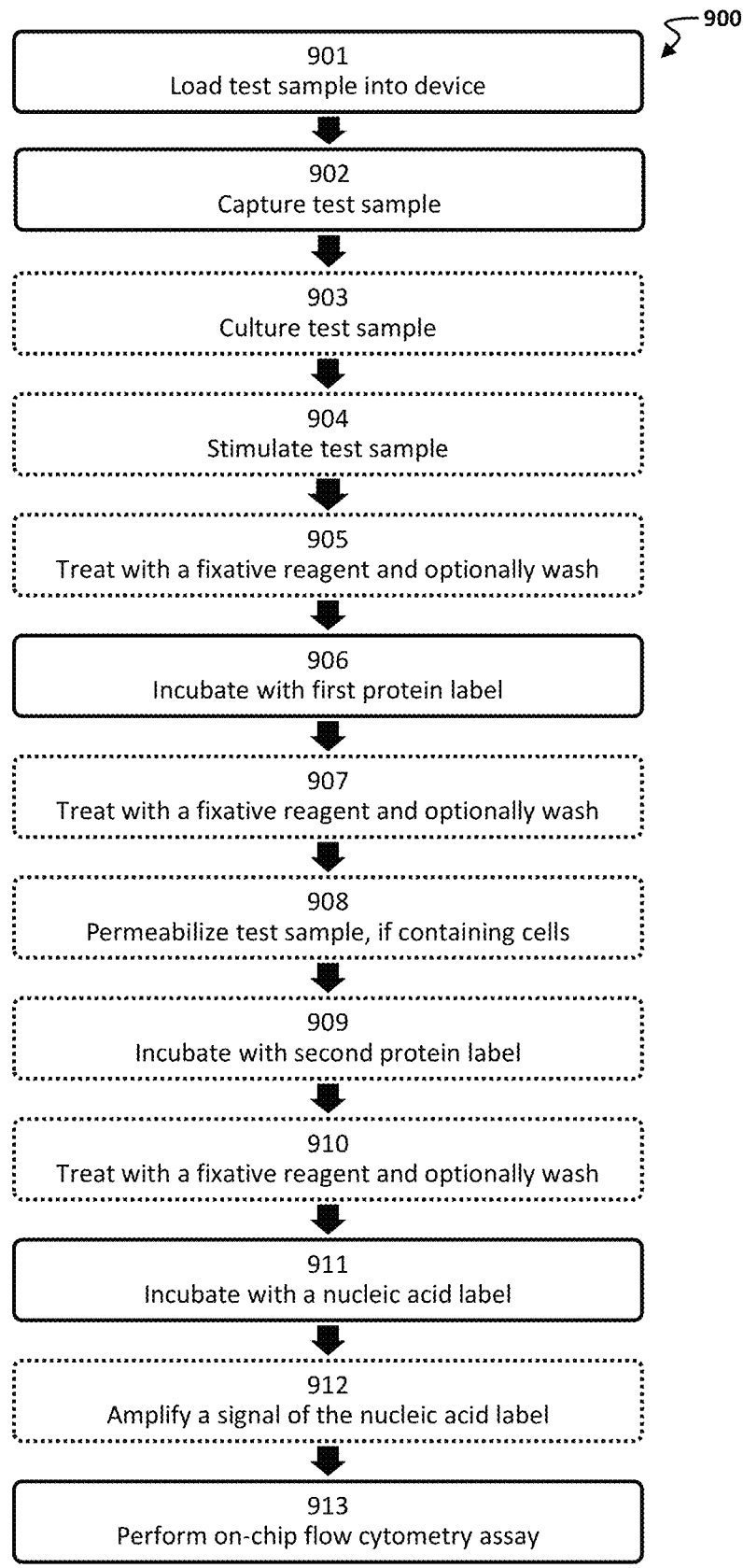
FIG. 9 shows a diagram of an exemplary method 900 for performing multiplexed analysis, as described herein, employing a first protein label and a nucleic acid label.

FIG. 9 provides an exemplary method 900 for performing multiplexed analysis in a microfluidic device. In a first step 901, a test sample portion is loaded into the device. To aliquot test sample into each assay chamber of the device, the test sample portion can be loaded into a main port (e.g., in fluidic communication with a main channel, which in turn is in fluidic communication with each assay chamber).

In a second step 902, the test sample portion is captured within each assay chamber. For instance, flow is employed in the device to deliver agents to the desired chamber. If the test sample was not captured, then flow could displace the test sample outside of the assay chamber. Thus, in the exemplary methods herein, the test sample is captured on a surface of the assay chamber for the duration of the multiplexed assay, and then the multiplexed-labeled sample portion is released for detection and/or analysis. Any useful capture reagent (e.g., such as any herein) can be used to capture the test sample. In one embodiment, a tissue adhesive (e.g., Cell-Tak™, a commercially available adhesive containing polyphenolic proteins extracted from *Mytilus edulis*) can be used to coat a chamber surface, and a protein (e.g., a protease) can be used to cleave proteins within the tissue adhesive in order to release the captured cells.

The next optional steps can be employed for sample preparation purposes. For instance, one optional step 903 can include culturing a sample portion, e.g., in order to increase the cell number to a particular confluence.

Another optional step 904 can include stimulating a sample portion with a stimulant (e.g., an exogenous molecule, peptide, protein, nucleic acid, etc., such as any herein). For instance, complicated reaction networks within cells can generally be perturbed by a stimulant, and the biomolecular components of these networks can be identified by exposing a cell with that stimulant and performing multiplexed analyses for numerous possible targets. For instance, ionomycin is a potent calcium ionophore, and calcium signaling is a general signaling pathway for various cellular processes. In T cells, ionomycin mediates T cell activation and, thus, serves as a useful stimulant for studying T cell activation. Other exemplary stimulants include one or more signaling molecules, modulators, activators, inhibitors (e.g., kinase inhibitors, such as wortmannin or LY294002; mitotic inhibitors, such as vincristine; and phosphatase inhibitors, such as okadaic acid), ionophores (e.g., calcium ionophores, such as ionomycin), endotoxins (e.g., lipopolysaccharide (LPS)), lipids (e.g., glycolipids), tumor promoters (e.g., phorbols and phorbol esters, such as 12-O-tetradecanoylphorbol-13-acetate (TPA) or phorbol-12-myristate-13-acetate (PMA)), antineoplastic agents (e.g., nocodazole), antitumor agents (e.g., paclitaxel), antibiotics (e.g., brefeldin A (BFA)), antibodies, drugs, hormones, toxins (e.g., phalloidin), etc.

Yet another optional step 905 includes treating the sample portion with a fixative reagent and, optionally, washing the fixed sample. In particular for whole cell-based analysis, preservation of cellular structures, morphology, surface characteristics, and internal biomolecules can be important. Thus, one or more fixative reagents can be employed to prevent autolysis. In addition, different fixative reagents can be employed to stabilize different structures within the cell sample. Any useful fixative reagent (e.g., any herein) can be employed.

In a next step 906, the method includes incubating the sample portion in an assay chamber with a protein label. As described herein, in certain steps, the incubating step 906 is performed on captured samples. Furthermore, if the multiplexed assay includes more than one protein label, then step 906 includes incubating with a first protein label (including a mixture of the first protein label with another label, e.g., a second protein label configured to detect a second target protein). Each protein label is configured to detect particular target protein(s) (e.g., any herein), thereby providing a labeled sample portion.

Various optional steps may be conducted with a labeled sample portion (e.g., from step 906 or any following steps). In one optional step 907, the labeled sample portion is treated with a fixative reagent and, optionally, washed. In another optional step 908, the sample portion is permeabilized, e.g., with a permeabilization reagent (e.g., any described herein). When the sample portion includes cells, then permeabilization may be needed for a label to penetrate cellular membranes.

If more than one protein labels are employed for the assay, then the method can optionally include a step 909 of incubating the sample portion in an assay chamber with a second protein label, where the second protein label is configured to detect a second target protein (e.g., any herein), thereby providing a doubly-labeled sample portion. Again, after this incubating step 909, the method can optionally include a step 910 of treatment with a fixative reagent and with an optional wash reagent (e.g., any buffer, such as any herein).

In yet another step 911, the method includes incubating the sample portion in an assay chamber with a nucleic acid label. Furthermore, if the multiplexed assay includes more than one nucleic acid label, then step 911 includes incubating with a first nucleic acid label (including a mixture of the first nucleic acid label with another label, e.g., a second nucleic acid label configured to detect a second target nucleic acid). Each nucleic acid label is configured to detect particular target nucleic acid(s) (e.g., any herein), thereby providing a multiplexed-labeled sample portion. Optionally, the nucleic acid label can include a signal that can be amplified. For instance, if the nucleic acid label includes an amplifiable region (e.g., an amplifiable nucleic acid portion), then one or more amplification reagents can be used to form numerous amplicons based on the amplifiable region, thereby providing an amplified signal. When the amplifiable region is present on a circular template, then the amplification reagents can be used to form a concatemer having numerous amplicon portions. If those amplicons can then be bound to a detectable marker, then the amplified signal provides an amplified detectable signal.

Figure 4A:
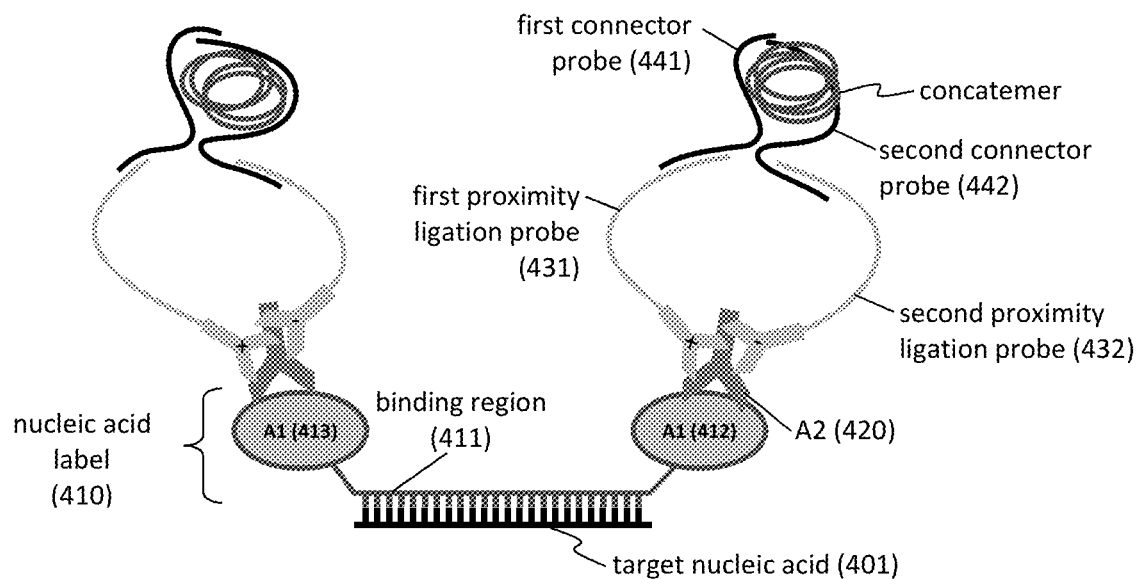
FIG. 4A-4B provides schematics of (A) an exemplary nucleic acid label 410 configured to detect the target nucleic acid 401 and (B) an exemplary reaction between a target miRNA, a cross-linker (e.g., EDC), and a nearby amino group (e.g., provided by a nearby protein).

FIG. 4A provides one exemplary method of amplifying a nucleic acid signal. As can be seen, the method includes the use of various labels to detect the target, such as a nucleic acid label 410 that binds to the target 401; a secondary label 420 that binds to the nucleic acid label 410; a tertiary label 431, 432 that binds to the secondary label 420; and a quaternary label 441, 442 that binds to the tertiary label 431, 432. Each of these labels is discussed below.

In general, the nucleic acid label 410 includes a nucleic acid-binding region 411 configured to detect the target nucleic acid 401. The nucleic acid label 410 can include one or more other chemical components, such as a detectable marker (e.g., any herein, such as a fluorophore, a quantum dot, etc.). Alternatively, the nucleic acid label can include one or more affinity agents to allow binding of the nucleic acid label to other secondary, tertiary, quaternary, etc. labels that facilitate detection, amplification, in a specific and/or selective manner. For instance, the nucleic acid label 410 can include one or more affinity agents 412, 413 having an optional linking region that covalently binds an affinity agent 412, 413 to the binding region 411.

The affinity agent can be one partner of a conjugating pair. As an example only, the conjugating pair can include a first affinity agent being a protein (e.g., digoxigenin or DIG) and a second affinity agent being an antibody that specifically binds that protein (e.g., an anti-digoxigenin antibody or anti-DIG antibody). Another exemplary conjugating pair includes biotin (first affinity agent) and streptavidin (second affinity agent). Other conjugating pairs and affinity agents forming that pair are described herein. As seen in FIG. 4A, the nucleic acid label 410 includes two affinity agents 412, 413 flanking the binding region 411. The number of affinity agents for each nucleic acid label can be selected to improve selectivity and/or sensitivity. In addition, the same or different affinity agents can be present for each nucleic acid label.

When the construct of the nucleic acid label includes a first affinity agent of a conjugating pair, then the secondary label can include a second affinity agent of the conjugating pair. In this manner, the secondary label specifically binds to the nucleic acid label (or the primary label). As seen in FIG. 4A, the secondary label 420 includes a second affinity agent (A2) that binds to the first affinity agent (A1) of the primary nucleic acid label 410. For instance, A1 can be DIG, and A2 can be an anti-DIG antibody. The secondary label can include a detectable marker (e.g., any herein). Alternatively, the secondary label can be configured to bind to a tertiary label.

As seen in FIG. 4A, two tertiary labels 431, 432 are employed for each secondary label 420, where each tertiary label binds to the secondary label. Thus, a tertiary label can include a third binding partner that binds to the second partner (e.g., as seen in FIG. 4A, the tertiary label 431 includes a third binding partner (labeled with +) that binds to the second partner A2 420). In one example, the first tertiary label is a first proximity ligation probe 431 having a third binding partner (e.g., an antibody, such as an anti-mouse antibody) configured to bind to the second binding partner A2 420 (e.g., a mouse anti-DIG antibody configured to bind to DIG in the primary nucleic acid label). The first proximity ligation probe 431 also includes a first nucleic acid sequence, and the second proximity ligation probe 432 includes a second nucleic acid sequence and a fourth binding partner (e.g., labeled with a detectable marker, where the third and fourth binding partners can be the same or different).

The proximity ligation probes provide an extended nucleotide, which in turn serves as a binding site for a quaternary label capable of being ligated and amplified. For instance, the quaternary label can be a padlock probe (e.g., a single-stranded nucleic acid sequence configured to bind to both the first and second nucleic acid sequences of the first and second proximity ligation probes) or two connector probes (e.g., two single-stranded nucleic acid sequences, where a first connector probe sequence is configured to bind to a portion of the first proximity ligation probe and the second connector probe sequence is configured to bind to a portion of the second proximity ligation probe). As seen in FIG. 4A, the first connector probe 441 includes a nucleic acid sequence having a portion that binds to a terminus of the first proximity ligation probe 431 and another portion that forms the circular template (i.e., once the first and second connector probes are ligated with a ligase). The second connector probe 442 includes a nucleic acid sequence having a portion that binds to the second proximity ligation probe 432 and another portion that forms the circular template. Once the first and second connector probes 441, 442 are ligated (e.g., using a DNA or RNA ligase), then a circular template is formed. Then, by including one or more enzymes (e.g., polymerases, such as a DNA or RNA polymerase), optional primers, nucleotides, etc., a concatemer is generated based on the circular template. Finally, if needed, one or more detectable markers capable of binding a sequence in the concatemer can be included. Additional modifications and methods for amplification and for probe design are provided in U.S. Pat. Nos. 5,665,539, 6,511,809, 6,558,928, 6,878,515, 7,074,564, and 8,268,554, as well as U.S. Pub. No. 2014/0194311, each of which is incorporated herein by reference in its entirety.

Figure 10:
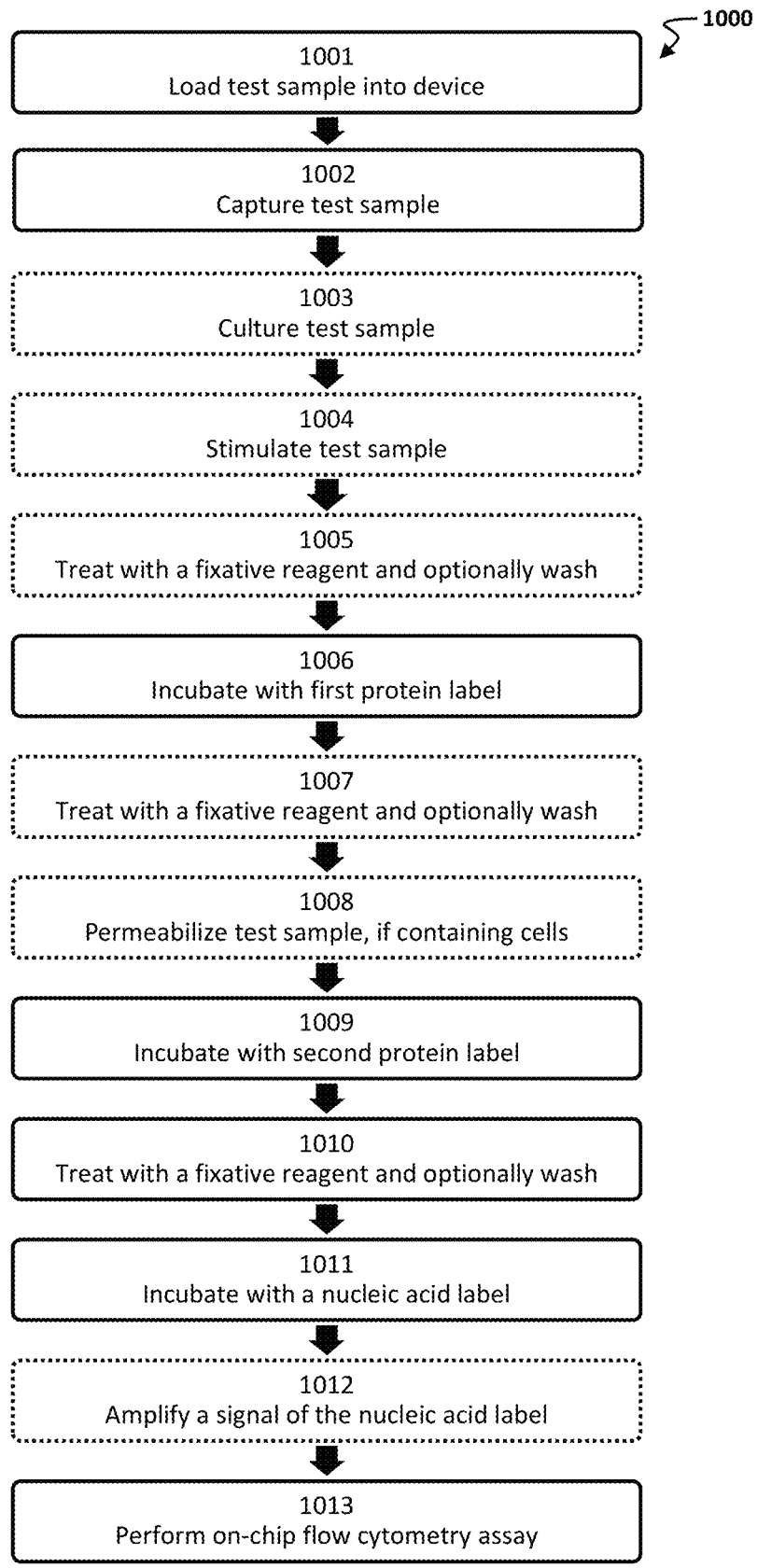
FIG. 10 shows a diagram of an exemplary method 1000 for performing multiplexed analysis, as described herein, employing a first protein label, a second protein label, and a nucleic acid label.

Finally, returning to FIG. 9, the method 900 includes the step 913 of performing an on-chip flow cytometry assay within the device. To facilitate hydrodynamic focusing of captured sample portion, the method can include detaching the sample portion (e.g., the multiplexed-labeled sample portion), thereby providing a detached sample portion; and delivering the detached sample portion to the flow cytometry channel. The step 913 can include establishing flow within the flow cytometry channel in order to provide a hydrodynamically focused sample portion (e.g., including the multiplexed-labeled sample portion from at least one assay chamber), activating an excitation source (e.g., thereby exciting the target or target particles with a flow cytometry excitation source), and receiving energy emitted from the labeled targets with a flow cytometry detector FIG. 10 provides an alternative exemplary method 1000 including a fixing step after use of a protein label but prior to treatment with a nucleic acid label. Such a method can be useful, e.g., for using a fixative reagent that cross-links a target nucleic acid to retains its location within the cell. In particular, when the fixative reagent detrimentally interacts with a protein label, then the protein label can include one or more inert detectable markers (e.g., quantum dots, instead of a protein-based fluorophore, which can be destroyed by one or more fixative reagents, e.g., EDC).

Figure 4B:
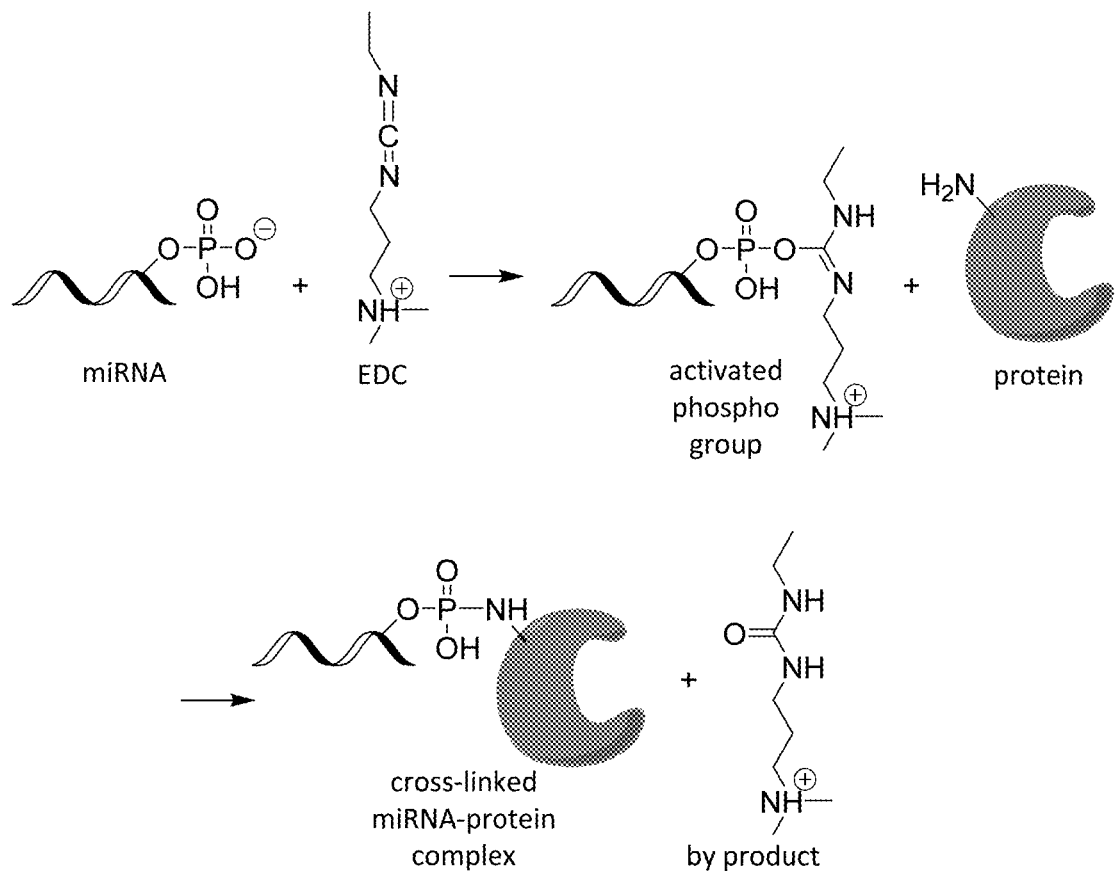

Accordingly, in FIG. 10, the method 1000 is one for performing multiplexed analysis with at least two protein labels and at least one nucleic acid label. The method 1000 requires a first step 1001 of loading a test sample into the device; a second step 1002 of capturing the test sample (e.g., within each assay chamber); a third step 1006 of incubating the sample portion with a first protein label; a fourth step 1109 of incubating the sample portion with a second protein label; a fifth step 1010 of treating the sample portion with a fixative reagent (e.g., a cross-linking agent, such as EDC or DCC) and an optional wash reagent (e.g., a buffer or any wash described herein); a sixth step 1011 of incubating the sample portion with a first nucleic acid label; and a final step 1013 of performing an on-chip flow cytometry assay. Regarding the fifth step 1010, FIG. 4B shows an exemplary schematic of a fixative reagent (e.g., EDC) that cross-links the miRNA target with a protein to form a cross-linked miRNA-protein complex.

The method 1000 includes various optional steps, such as step 1003 of culturing a sample portion; step 1004 of stimulating a sample portion with a stimulant; step 1005 of treating the sample portion with a fixative reagent and, optionally, washing the fixed sample; step 1007 of treating the sample portion with a fixative reagent and, optionally, washing the fixed sample, where the fixative reagent of steps 1005, 1007, 1010 can be the same or different; step 1008 of permeabilizing the sample portion with a permeabilization reagent (e.g., any described herein); and/or step 1012 of amplifying a signal of the nucleic acid label.

Figure 11:
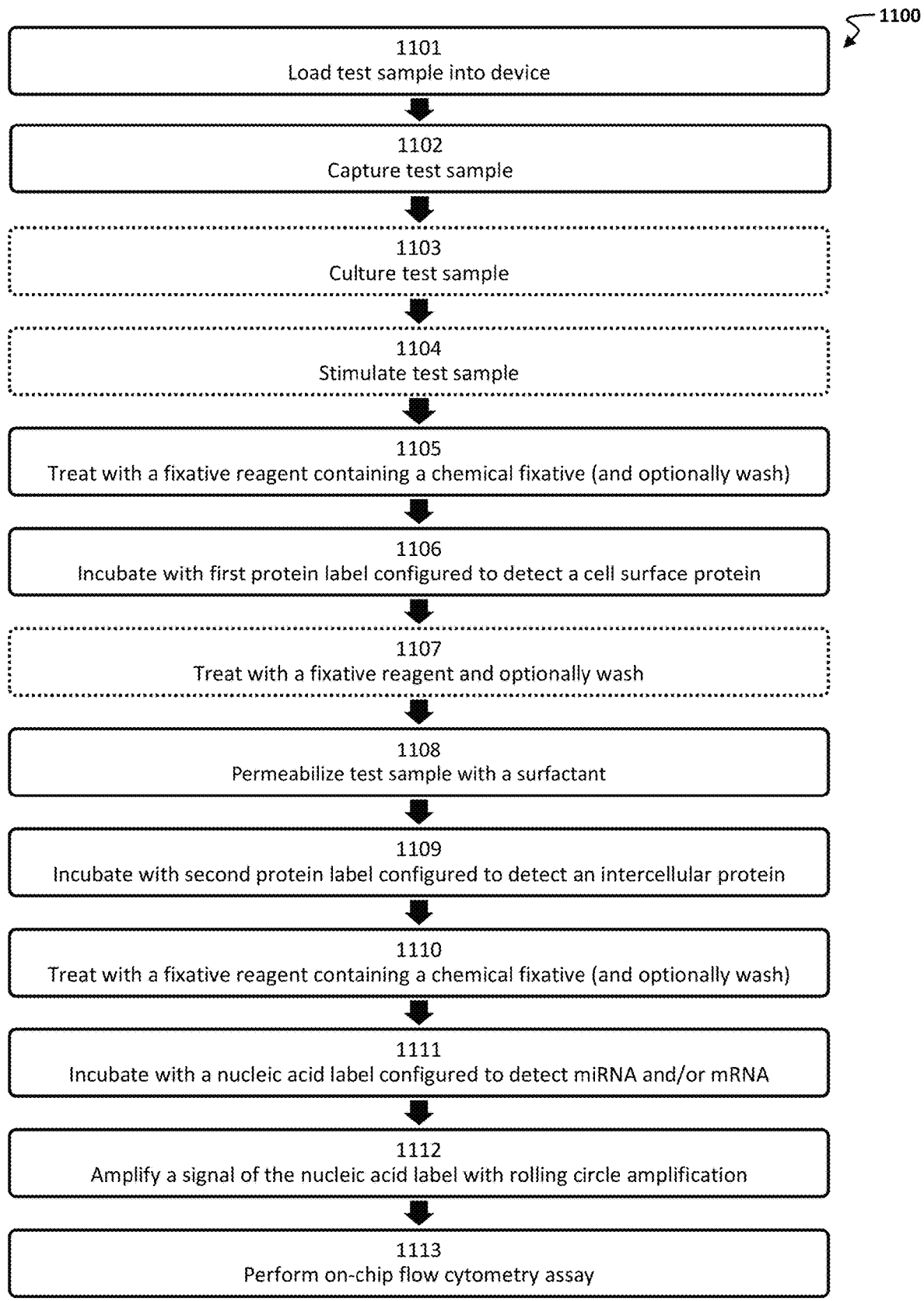
FIG. 11 shows a diagram of an exemplary method 1100 for performing multiplexed analysis, as described herein, employing various fixative reagents, permeabilization reagents, and labels.

FIG. 11 provides an alternative exemplary method 1100 including two fixing steps and a permeabilizing step. This method can be useful, e.g., for labeling cell surface proteins and then later using a permeabilizing reagent for labeling intercellular protein and/or nucleic acid targets.

Accordingly, in FIG. 11, the method 1100 is one for performing multiplexed analysis with at least one cell surface protein label, at least one intracellular protein label, and at least one nucleic acid label. The method 1100 requires a first step 1101 of loading a test sample into the device; a second step 1102 of capturing the test sample (e.g., within each assay chamber); a third step 1105 of treating the sample portion with a fixative reagent (e.g., paraformaldehyde, or another chemical fixative described herein); a fourth step 1106 of incubating the sample portion with a first protein label configured to detect a cell surface protein; a fifth step 1108 of permeabilizing the sample portion with a permeabilization reagent (e.g., Triton™ X-100 or any described herein); a sixth step 1109 of incubating the sample portion with a second protein label configured to detect an intracellular protein; a seventh step 1110 of treating the sample portion with a fixative reagent (e.g., a cross-linking agent, such as EDC or DCC); an eighth step 1111 of incubating the sample portion with a first nucleic acid label configured to detect miRNA and/or mRNA; a ninth step 1112 of amplifying a signal of the nucleic acid label(s); and a final step 1113 of performing an on-chip flow cytometry assay.

The method 1100 includes various optional steps, such as step 1103 of culturing a sample portion; step 1104 of stimulating a sample portion with a stimulant; and step 1107 of treating the sample portion with a fixative reagent and, optionally, washing the fixed sample, where the fixative reagent of steps 1105, 1107, 1110 can be the same or different.

Multiplexed Analysis of Targets

The devices, platforms, and methods of the inventions can be employed to perform multiplexed analysis of any target nucleic acid, target protein, target post-translational modification (PTM), and/or other target biomolecules, as well as any combinations of these.

Exemplary target nucleic acids include mRNA, miRNA, RNA (e.g., any herein), DNA (e.g., any herein), including single-stranded forms thereof, double-stranded forms thereof, sense and antisense forms thereof, as well as any having natural or non-natural nucleobases or nucleic acids. Exemplary target proteins include one or more cell surface proteins, transmembrane or membrane proteins, intercellular proteins, cytosolic proteins, nuclear pore complexes, enzymes, structural proteins (e.g., fibrous proteins), globular proteins, hormones, etc. Exemplary target post-translational modification: phosphorylation, adenylylation, dephosphorylation, glycosylation, ubiquitination, acylation, alkylation (e.g., methylation or ethylation), amidation, deamidation, carbamylation, carboxylation, hydroxylation, nitrosylation, succinylation, sulfation, glycation, myristoylation, palmitoylation, prenylation, glypiation, addition of one or more cofactors (e.g., a lipoate, flavin, heme, or phosphopantetheinyl moiety), etc. Exemplary target biomolecules include one or more carbohydrates, lipids, glycosaminoglycans, steroids, etc.

For instance, the devices, platforms, and methods of the inventions can be employed to analyze miRNA (see, e.g., FIGS. 5A-5D), miRNA with a cell surface protein (e.g., CD69, such as in FIGS. 6A-6C), and a portfolio of targets, such as any combination of mRNAs, miRNAs, cell surface proteins, phosphorylation, cytosolic proteins, and glycosylation (see, e.g., FIG. 8A-8F). Any useful cellular process, such as those in FIG. 7, can be studied using the multiplexed process described herein.

Labels for Target Detection

For multiplexed detection, the present invention employs labels that are selective for the desired target. For instance, a protein label is an agent that is configured to detect a target protein, and a nucleic acid label is an agent that is configured to detect a target nucleic acid, and a PTM label is an agent that is configured to detect a target post-translational modification. Exemplary labels are described herein.

In one example, the protein label includes a protein-binding region and optionally, a detectable marker (e.g., any herein). The protein-binding region can include any useful protein-binding region (e.g., an antibody, as well as fragments thereof). In addition, the protein label can be used in combination with a secondary protein label, in which the secondary label binds to the protein label. For instance, the protein label can include a protein-binding region that binds to the target and a first affinity agent (e.g., biotin of a conjugating pair including biotin and avidin); and the secondary label can include a second affinity agent (e.g., avidin) and an optional detectable marker. In this manner, a plurality of labels can be employed to facilitate selective detection of the target and sensitive observation of any detectable signals. In some embodiments, a secondary label is configured to directly or indirectly bind to the protein label (e.g., thereby providing an excited label for the multi-labeled sample portion).

In another example, the nucleic acid label includes a nucleic acid-binding region (e.g., with sufficiently complementary to specifically bind a target nucleic acid) and an affinity agent (e.g., such as a first partner of a conjugating pair). Additional secondary, tertiary, quaternary, etc. labels (e.g., as described herein) can be employed with the primary nucleic acid label (see, e.g., FIG. 4A and associated text). In some embodiments, a secondary label is configured to directly or indirectly bind to the nucleic acid label (e.g., thereby providing an excited label for the multi-labeled sample portion).

In yet another example, the PTM label includes a region configured to selectively bind to a post-translational modification or a post-translation, modified protein. For instance, the label can differentially bind to a protein having a post-translational modification, as compared to a non-modified protein (e.g., an antibody selective for a phosphorylated protein, as compared to its non-modified type; a lectin affinity agent that selectively binds sugar moieties; or a cationic carbocyanine dye that preferentially stains highly acidic proteins (e.g., phosphoproteins and calcium-binding proteins, such as 1-ethyl-2-[3-(3-ethylnaphtho[1,2d] thiazolin-2-ylidene)-2-methylpropenyl]-naphtho[1,2d]thiazolium bromide)).

In another instance, the PTM can include a moiety capable of being reactive or being activated, where the reactive/active moiety can then be reacted with a detectable marker (e.g., a glycol moiety on a glycosylated protein, where this moiety can be oxidized to an aldehyde, which in turn can be reacted with a detectable marker to form a labeled, detectable conjugate). Any useful detectable marker can be employed, such as a fluorescent hydrazide (e.g., a Pro-Q® Emerald 300 dye) to form a fluorescently detectable conjugate, a digoxigenin hydrazide to form a conjugate that can be bound by an antidigoxigenin antibody having a detectable marker (e.g., a fluorophore, quantum dot, or detectable enzyme), and/or a biotin hydrazide to form a conjugated that can be bound by a streptavidin-containing moiety (e.g., horseradish peroxidase or alkaline phosphatase conjugates of streptavidin). Additional PTM labels and methods for PTM detection are described in Steinberg T H et al., "Rapid and simple single nanogram detection of glycoproteins in polyacrylamide gels and on electroblots," Proteomics 2001 July; 1(7):841-55; and Steinberg T H et al., "Global quantitative phosphoprotein analysis using Multiplexed Proteomics technology," Proteomics 2003 July; 3(7): 1128-44, each of which is incorporated herein by reference in its entirety. In addition, commercially available labels include, e.g., Pro-Q® Diamond Phosphoprotein Gel Stain (P-33300, Molecular Probes®, available from Life Technologies, Grand Island, N.Y., Thermo Fisher Scientific Inc.); and Pro-Q® Emerald 300 or 488 Glycoprotein Gel Stain Kit (P-21855 or P-21875, Molecular Probes®, available from Life Technologies).

For the labels, any useful affinity agent can be employed. In certain embodiments, the first and second affinity agent bind together with a high binding affinity (e.g., at least about $10^{-4}$ M, usually at least about $10^{-6}$ M or higher, e.g., $10^{-9}$ M or higher) that is sufficient to ensure specificity and/or sensitivity.

Exemplary affinity agents include an antibody, such as polyclonal, monoclonal, and single chain forms thereof, fragments thereof, polyepitopic specific forms thereof, multispecific forms thereof, chimeric forms thereof, and humanized forms thereof; a receptor; a lectin; an aptamer (e.g., a nucleic acid aptamer); a chemical moiety; a small molecule (e.g., a cyclical organic compound); a soluble cell-surface receptor or derivative thereof; an antibody mimetic (e.g., an affibody); a cofactor (e.g., biotin); a coenzyme; an enzyme; a sugar moiety; a polysaccharide; a lipid; a toxin; a click-chemistry moiety (e.g., an azido group, an alkynyl group, a dienophile group, or a diene group); a steroid (e.g., digoxigenin); and/or a protein (e.g., avidin, streptavidin, or neutravidin).

The affinity agent can be one partner of a conjugating pair. Exemplary conjugating pairs include an antibody and an antigen for that antibody; an aptamer and an affinity agent selected to specifically bind that aptamer, such as an anti-thrombin aptamer and thrombin; a lectin and a sugar moiety, such as concanavalin A and a glycoprotein; digoxigenin (DIG) and an anti-DIG antibody; a mouse antibody and an anti-mouse antibody; a hapten and an anti-hapten antibody; biotin and streptavidin; fluorescein and an anti-fluorescein antibody optionally labeled with a detectable marker (e.g., an enzyme); an optionally substituted alkynyl group and an optionally substituted azido group; an optionally substituted diene having a 4 π-electron system and an optionally substituted dienophile or an optionally substituted heterodienophile having a 2 π-electron system; a nucleophile and a strained heterocyclyl electrophile; an optionally substituted amino group and an aldehyde or a ketone group; an optionally substituted amino group and a carboxylic acid group; an optionally substituted hydrazine and an aldehyde or a ketone group; an optionally substituted hydroxylamine and an aldehyde or a ketone group; and/or a nucleophile and an optionally substituted alkyl halide. Any other useful conjugating pair may be employed. In addition, each affinity agent can be optionally labeled with a detectable marker (e.g., an enzyme, a fluorophore, a quantum dot, etc., or any herein) by way of an optional linking agent (e.g., an poly(ethylene glycol), an alkylene group, etc.). Additional affinity agents and labels are described in Wu M et al., Curr. Opin. Biotechnol. 2012 February; 23(1):83-8; and Boyce M et al., "Bringing chemistry to life," Nat. Methods 2011 August; 8(8):638-42, each of which is incorporated herein by reference in its entirety.

Furthermore, affinity agents can be selected based on overlapping selectivity between conjugating pairs. For instance, a primary label can include a DIG as an affinity agent, and the secondary label can include a mouse anti-DIG antibody, which binds to DIG. The tertiary label, in turn, can include an anti-mouse antibody, which binds to the mouse anti-DIG antibody. In this manner, sets of affinity agents, not just pairs, can be designed and implemented in primary, secondary, tertiary, quaternary, etc. labels.

Detectable Marker

The probes and labels herein can include any useful detectable marker. Exemplary detectable markers include a dye, such as an electroactive detection agent, a fluorescent dye, a luminescent dye, a chemiluminescent dye, a colorimetric dye, a radioactive agent, etc.; a particle, such as a microparticle, a nanoparticle, a latex bead, a colloidal particle, a magnetic particle, a fluorescent particle, etc.; a tag (e.g., an electroactive tag, an electrocatalytic tag, a fluorescent tag, a colorimetric tag, a quantum dot, a nanoparticle, a microparticle, a barcode, a radio tag (e.g., an RF tag or barcode); an affinity agent (e.g., any herein, such as avidin or biotin); an enzyme that can optionally include one or more linking agents and/or one or more dyes; an enzyme that can be detected by way of an enzymatically cleavable substrate (e.g., horseradish peroxidase by way of a cleavable substrate having an oxidizable group, thereby providing an optically detectable signal; or alkaline phosphatase by way of a cleavable substrate having a phosphate group); an amplifying agent (e.g., a PCR agent, such as a polymerase, one or more deoxyribonucleotide triphosphates, a divalent metal (e.g., $MgCl_2$), a template DNA, and/or a primer (e.g., for binding to a selective region of the target nucleic acid); a globulin protein (e.g., bovine serum albumin); a sandwich assay reagent; and/or a catalyst (e.g., that reacts with one or more substrates to provide a detectable signal). Additional detectable markers are described in Wu M et al., Curr. Opin. Biotechnol. 2012 February; 23(1):83-8; and Boyce M et al., Nat. Methods 2011 August; 8(8):638-42, each of which is incorporated herein by reference in its entirety.

Capture Reagents

As described herein, the devices and methods of the invention can include capturing a sample portion on a surface of the device (e.g., within an assay chamber, such as on at least one chamber wall). In one embodiment, a solution is employed to deposit one or more adhesion layers within a chamber or channel of the device. The adhesion layer can be formed from any useful substance, such as a protein (e.g., an extracellular matrix protein, a globulin protein, a structural protein, or a fibrous protein, including albumin, an immunoglobulin, fibrin, collagen, fibronectin, laminin, entactin, or tenascin C), a polypeptide, a protein fraction, a proteinaceous mixture (e.g., Cell-Tal™, a commercially available tissue adhesive containing polyphenolic proteins extracted from *Mytilus edulis* and formulated in 5% acetic acid; or Matrigel™, a gelatinous protein mixture from Engelbreth-Holm-Swarm mouse sarcoma cells), a polymer (e.g., a charged polymer, such as cationic poly-L-lysine (PLL) or polyethyleneimine (PEI)), and/or a peptide recognition motif (e.g., a Arg-Gly-Asp motif).

When a protein component is employed, then any useful enzyme or chemical agent can be used to release the captured sample portion. Exemplary enzymes and chemical agents include Arg-C proteinase, Asp-N endopeptidase, BNPS-Skatole, a caspase (e.g., caspase 1, 2, 3, 4, 5, 6, 7, 8, 9 or 10), chymotrypsin, clostripain (clostridiopeptidase B), cyanogen bromide (CNBr), enterokinase, Factor Xa, formic acid, glutamyl endopeptidase, granzyme B, hydroxylamine (e.g., $NH_2OH$), iodosobenzoic acid, LysC lysyl endopeptidase (*Achromobacter* proteinase I), LysN peptidyl-Lys metalloendopeptidase, neutrophil elastase, 2-nitro-5-thiocyanobenzoic acid (NTCB optionally with nickel), pepsin, proline-endopeptidase, proteinase K, staphylococcal peptidase I, tobacco etch virus protease, thermolysin, thrombin, and/or trypsin.

Amplification

In some embodiments, the method includes use of one or more labels including a nucleic acid sequence (e.g., a template, including a padlock or a circular template) capable of being amplified to provide an amplicon (e.g., short or long nucleic acid sequences, which includes concatemers). In particular embodiments, the amplicon is produced by an amplification reaction, e.g., an isothermal amplification or a rolling circle amplification. The amplifying step can include use of a polymerase (e.g., a DNA polymerase).

In yet other embodiments, the amplifying step includes performing an amplification reaction by providing one or more antibodies configured to bind to the primary nucleic acid label, one or more proximity ligation probes configured to bind to the one or more antibodies, connector probes configured to form a circular template (e.g., where circularization is mediated by the use of one or more ligases) and to bind the proximity ligation probes, one or more enzymes (e.g., polymerases) configured to generate a concatemer based on the circular template, one or more nucleotides (e.g., dNTPs), and/or one or more splint oligonucleotides (e.g., to bind the circular template and/or to bind to a terminus on each of the two connector probes)

Fixative Reagents

The fixative reagent can include any useful agent or compound configured to form a bond (e.g., a covalent bond) between two reactive groups (e.g., a carboxyl group and an amino group or a phospho group and an amino group). Exemplary fixative reagents include a chemical fixative (e.g., formaldehyde, paraformaldehyde, glutaraldehyde, formalin, acetone, isopropanol, ethanol, and/or methanol) or a cross-linker, as well as combinations thereof. Exemplary cross-linkers include those for forming a covalent bond between a carboxyl group (e.g., —$CO_2$H) and an amino group (e.g., —$NH_2$) or between a phospho group (e.g., —P(O)(OH)$_2$) and an amino group (e.g., —$NH_2$), such as 1-ethyl-3-(3-dimethylaminopropyl)carbodiimide (EDC) and dicyclohexylcarbodiimide (DCC), optionally used with N-hydroxysuccinimide (NHS) and/or N-hydroxysulfosuccinimide (sulfo-NHS). Other cross-linkers include those for forming a covalent bond between an amino group (e.g., —$NH_2$) and a thymine moiety, such as succinimidyl-[4-(psoralen-8-yloxy)]-butyrate (SPB); a hydroxyl group (e.g., —OH) and a sulfhydryl group (e.g., for a cysteine moiety), such as p-maleimidophenyl isocyanate (PMPI); between an amino group (e.g., —$NH_2$) and a sulfhydryl group (e.g., for a cysteine moiety), such as succinimidyl 4-(p-maleimidophenyl)butyrate (SMPB) and/or succinimidyl 4-(N-maleimidomethyl)cyclohexane-1-carboxylate (SMCC); and between a sulfhydryl group (e.g., for a cysteine moiety) and a carbonyl group (e.g., an aldehyde group, such as for an oxidized glycoprotein carbohydrate), such as N-beta-maleimidopropionic acid hydrazide-trifluoroacetic acid salt (BMPH) and/or 3-(2-pyridyldithio)propionyl hydrazide (PDPH).

Permeabilization Reagents

The permeabilization reagents can include any useful agent or compound configured to permeabilize cell membranes, or portions thereof. Exemplary permeabilization reagents include a surfactant, such as Triton™ X-100 (e.g., polyethylene glycol p-(1,1,3,3-tetramethylbutyl)-phenyl ether), sodium dodecyl sulfate (SDS), Tergitol-type NP-40 (nonyl phenoxypolyethoxylethanol), and polysorbate 20 (Tween 20); an alcohol, such as methanol; a solvent (e.g., acetone or acetic acid); a glycoside, such as saponin or digitonin; a protease, such as proteinase K; or an exotoxin, such as streptolysin O.

Samples

Any useful test sample can be analyzed. Exemplary test samples can include one or more cells, including rare cells (e.g., primary cells, stem cells, cancer cells, etc.); a biopsy sample; a cell; a tissue; a fluid; a swab; a biological sample (e.g., blood, serum, plasma, saliva, etc.); an environmental sample; a microorganism; a microbe; a virus; a bacterium; a fungus; a parasite; a helminth; a protozoon; a nucleic acid (e.g., oligonucleotides, polynucleotides, nucleotides, nucleosides, molecules of DNA, or molecules of RNA, including a chromosome, a plasmid, a viral genome, a primer, or a gene); a protein (e.g., a glycoprotein, a metalloprotein, an enzyme, a prion, a kinase, a membrane protein, a receptor, or an immunoglobulin); a metabolite; a cytokine; a cofactor; a factor (e.g., a transcription factor); a sugar or saccharide (e.g., including polysaccharides and monosaccharides); a lipid; a lipopolysaccharide; a salt; an ion; and/or a particle (e.g., cells, including macrophage cells, and beads, including beads having cells or other biological materials attached to the beads). Such samples can be tested for any use, such as point-of-care cell-based assays, diagnoses of complex disorders, medical treatment (e.g., by tracking patient responses to drug therapies), and/or multiplexed cellular analysis of signaling events on a single-cell level.

EXAMPLES

Example 1: Microfluidic Platform for the Multiplexed Detection of miRNA, mRNA, and Proteins at Single-Cell Resolution MicroRNAs (miRNAs) are non-coding, small single-stranded RNAs that modulate and regulate gene expression in numerous biological systems ranging from cell development and differentiation, in immune response and inflammation, and in pathological states, such as cancer and autoimmune diseases (see, e.g., Alvarez-Garcia I et al., "MicroRNA functions in animal development and human disease," *Development* 2005; 132:4653-62; Baltimore D et al., "MicroRNAs: new regulators of immune cell development and function," *Nat. Immunol.* 2008; 9:839-45; Lodish H F et al., "Micromanagement of the immune system by microRNAs," *Nat. Rev. Immunol.* 2008; 8:120-30; Kasinski A L et al., "Epigenetics and genetics. MicroRNAs en route to the clinic: progress in validating and targeting microRNAs for cancer therapy," *Nat. Rev. Cancer* 2011; 11:849-64; and Alevizos I et al., "MicroRNAs in Sjogren's syndrome as a prototypic autoimmune disease," *Autoimmun. Rev.* 2010; 9:618-21). As a result, miRNAs have become the subject of intense research as potential diagnostic disease biomarkers as well as therapeutic targets for drug development.

While traditional bulk assay methods (e.g., microarray, RT-qPCR, and sequencing technologies) have yielded high volume of information regarding the expression profiles of miRNAs, the progress towards developing miRNA clinical diagnostics and therapies have been slow, due large in part to the complex nature of miRNA biology. The expression and function of miRNAs are tissue-specific—the same miRNA can exert opposite modulatory effects on signaling pathways, modulate entirely different signaling pathways, or have no effect, all depending on the tissue type and cellular context.

Without the ability to monitor mRNAs, proteins, and transient signaling events along with miRNAs in the same cell, it is very difficult to ascertain what relationship, if any, miRNA expression has to health or disease of that cell. Bulk profiling methods generate averaged miRNA measurement from heterogeneous cell populations, and the information regarding how miRNA expression levels relate to mRNA and protein indicators of the cellular physiological state is lost in the sample preparation process. In addition, averaged cellular signal from a population can mask the cell-to-cell variability of response within that population, and therefore single-cell resolution analysis of miRNA levels will yield information otherwise unattainable using bulk methods.

To address the need for a new technology that provides single-cell resolution analysis of miRNAs in relation to mRNA and protein biomarkers, we have developed an automated, microfluidic platform with accompanying molecular assays that enable rapid processing of intact cells (~8 hours) to simultaneously detect small non-coding RNA (e.g., miRNAs), mRNAs, proteins, and post-translational modifications at single-cell resolution, with >95% reduction in sample and reagent requirement (see, e.g., Wu M et al., "Single cell microRNA analysis using microfluidic flow cytometry," *PLoS One* 2013; 8(1):e55044 (6 pages); Wu M et al., "Microfluidic molecular assay platform for the detection of miRNAs, mRNAs, proteins, and posttranslational modifications at single-cell resolution," *J. Lab. Autom.* 2014 December; 19(6):587-92; Wu M et al., "Microfluidically-unified cell culture, sample preparation, imaging and flow cytometry for measurement of cell signaling pathways with single cell resolution," *Lab Chip* 2012 Aug. 21; 12(16): 2823-31; and Srivastava N et al., "Fully integrated microfluidic platform enabling automated phosphoprofiling of macrophage response," *Anal. Chem.* 2009 May 1; 81(9): 3261-9). The device provides fluorescent images, as well as flow cytometry measurements of each target or biomarker, and provides an unprecedented, comprehensive look into the molecular physiological state of single cells.

At the heart of the platform is a glass microfluidic chip with ten individually addressable cell holding chambers or assay chambers (FIG. 2A), thereby allowing ten different conditions per experiment. Each device is fluidically connected to fourteen programmable valves, reagent reservoirs, and pumps (FIG. 2C) that use positive pressure to drive the movement of cells and reagents on and off the chip. A series of custom add-on features including the pumps and valves, pressure controllers, and temperature control are controlled by the user using a graphic user interface (GUI) with programmable features for automated sample preparation. For instance, the in-house designed software allows the experimenter to control the pressure, temperature, and valves by programming each step of the experiment to run automatically. The chip's configuration allows for automated interrogation of ten different cell types or experimental conditions, using only 270 nL of reagent per chamber, thereby reducing the reagent cost more than 95%.

The microfluidic chip sits in a manifold retrofitted to an inverted fluorescent microscope with an attached camera (FIG. 2B), and the user can visually track fluid and cell movement during the experiment, as well as perform bright field and fluorescent microscopy analysis after automated sample preparation (FIG. 2B). After sample preparation and image capture, the chip and manifold are moved to a custom-built micro-flow cytometer (FIG. 2D). Cells are detached by proteolytic cleavage (e.g., employing a protease) and hydrodynamically focused at the center of the chip for on-chip flow cytometry. The optical fiber is positioned on top of the chip, and aligned to the hydrodynamically focused path of the cells. The laser is applied from the bottom of the chip, and the signal from the passing cells is recorded by one or more detectors (e.g., photomultiplier tubes, charge-coupled devices, etc.) situated underneath the chip.

In order to detect miRNAs at single-cell resolution, a novel flow cytometry compatible fluorescent in situ hybridization (flow-FISH) assay to detect miRNAs using locked nucleic acid (LNA) containing probes has been developed. The LNA flow-FISH assay combines the advantage of LNA's high melting temperature with the specificity of proximal ligation and rolling circle amplification to provide highly specific amplification of otherwise undetectable miRNA signals in an intact cell (FIG. 4A), which then can be visualized via microscopy and quantified using flow cytometry (see, e.g., FIG. 6A-6C).

The miRNA can be detected in any useful manner. Similar to the nucleic acid label in FIG. 4A, a double digoxigenin (DIG) labeled LNA-containing probe can be hybridized to the target, a mature miR155. The nucleic acid portion of the probe allows for specific hybridization to the target, whereas the affinity agents (e.g., DIG) allows the probe to be captured by one or more other affinity agents, such an antibody (e.g., an anti-DIG antibody).

The subsequent steps allow for further probes to be bound to the DIG-LNA probe and to form a circular template. For instance, a monoclonal anti-DIG antibody can be bound to the DIG affinity agent. Then, a pair of proximity ligation probes is bound to the monoclonal anti-DIG antibody, where the proximity ligation probe includes a secondary antibody configured to bind to the anti-DIG antibody and an oligonucleotide region. Next, connector probes were provided, in which the connector probe includes a nucleic sequence portion that is complementary to a terminal portion of the proximity ligation probes. In use, the connector probes are hybridized to a terminal portion of the proximity ligation probe, and then ligated to form a circular template containing a short recognition sequence.

Finally, rolling circle amplification of the circular template is performed to yield single-stranded concatemers. For fluorescence detection, the concatemer can be hybridized to a labeled detection probe that is complementary to a recognition sequence encoded by the circular template. The labeled detection probe can include a detectable label (e.g., any herein) and a nucleic acid sequence that is complementary to a recognition sequence, or a portion thereof.

The detection of miRNA species by LNA-flow FISH can be multiplexed with mRNA detection, and the isothermal nature of rolling circle amplification makes multiplexing with protein immunostaining possible. The multiplexing of miRNA and protein detection using LNA flow-FISH was demonstrated using miR155 and T-cell activation marker CD69 protein in activated T cells, and the flow-FISH results show comparable sensitivity to qPCR (see Example 2 herein).

Other molecular assays that profile cell surface protein markers, transient cell surface receptor activation, intracellular proteins, post-translational modifications (e.g., phosphorylation and/or dynamic glycosylation of proteins), and mRNA have also been developed for the microfluidic platform (see, e.g., FIGS. 8A-8F and Example 4 herein). All microfluidic molecular assays developed on the platform are compatible for multiplexing with each other, thereby providing a systems-level analysis of miRNAs in the native cellular context at a single-cell resolution. The platform and accompanying assays will advance the knowledge of miRNA function and their correlation with disease states, and holds great potential for both basic miRNA research and the development of multiplexed miRNA/mRNA/protein biomarker panels for disease diagnostics and companion diagnostics.

Example 2: Single-Cell microRNA Analysis Using Microfluidic Flow Cytometry

MicroRNAs (miRNAs) have cell type and cell context-dependent expression and function. miRNAs function by directly binding the 3' untranslated regions (UTRs) of target mRNAs and recruit the RNA-induced silencing complex to degrade target mRNA (see, e.g., Krutzfeldt J et al., "MicroRNAs: a new class of regulatory genes affecting metabolism," *Cell. Metab.* 2006; 4:9-12). In humans, over 1000 miRNAs have been identified (see, e.g., Griffiths-Jones S, "The microRNA registry," *Nucleic Acids Res.* 2004; 32:D109-11), and each miRNA can potentially repress hundreds of target mRNAs, indicating the importance and complexity of this gene regulation system.

Several methods have been developed for detection of miRNAs: Northern blotting, oligonucleotide microarrays, quantitative PCR (qPCR) assays, next generation sequencing, and in situ hybridization (ISH) (see, e.g., Valoczi A et al., "Sensitive and specific detection of microRNAs by northern blot analysis using LNA-modified oligonucleotide probes," *Nucleic Acids Res.* 2004; 32:e175; Castoldi M et al., "A sensitive array for microRNA expression profiling (miChip) based on locked nucleic acids (LNA)," *RNA* 2006; 12:913-20; Thomson J M et al., "A custom microarray platform for analysis of microRNA gene expression," *Nat. Methods* 2004; 1:47-53; Duncan D D et al., "Absolute quantitation of microRNAs with a PCR-based assay," *Anal. Biochem.* 2006; 359:268-70; Raymond C K et al., "Simple, quantitative primer-extension PCR assay for direct monitoring of microRNAs and short-interfering RNAs," *RNA* 2005; 11:1737-44; Xu G et al., "Transcriptome and targetome analysis in MIR155 expressing cells using RNA-seq," *RNA* 2010; 16:1610-22; and Nielsen B S, "MicroRNA in situ hybridization," *Methods Mol. Biol.* 2012; 822:67-84).

With the exception of qPCR and ISH, all of these methods require lysis and homogenization of cells in order to provide measurement of miRNA averaged over a large number of cells. Cells are heterogeneous in nature and hence, in many applications, it is desirable to measure miRNA in single cells. The advent of locked nucleic acid (LNA) containing probes has enabled RT-qPCR and in situ hybridization (ISH) analysis of miRNA at single-cell resolution (see, e.g., Tang F et al., "MicroRNA expression profiling of single whole embryonic stem cells," *Nucleic Acids Res.* 2006; 34:e9; Tang F et al., "220-plex microRNA expression profile of a single cell," *Nat. Protoc.* 2006; 1:1154-9; Pena J T et al., "miRNA in situ hybridization in formaldehyde and EDC-fixed tissues," *Nat. Methods* 2009; 6:139-41; and de Planell-Saguer M et al., "Rapid in situ codetection of noncoding RNAs and proteins in cells and formalin-fixed paraffin-embedded tissue sections without protease treatment," *Nat. Protoc.* 2010; 5:1061-73).

Single-cell miRNA RT-qPCR, however, requires many steps including isolation of single cells followed by lysis, RNA extraction, and amplification. In addition, this technology has limited throughput. LNA-ISH allows detection of endogenous miRNA in single cells without lysis and RNA extraction, but it is labor-intensive, at times poorly reproducible, and provides only a qualitative assessment. Thus, LNA-ISH is used most frequently for fixed tissue sections.

Microfluidic devices have attracted significant attention in single-cell analysis (see, e.g., Wu M et al., "Single-cell protein analysis," *Curr. Opin. Biotechnol.* 2012; 23:83-8; Yilmaz S et al., "Single cell genome sequencing," *Curr. Opin. Biotechnol.* 2012; 23:437-43; and Powell A A et al., "Single cell profiling of circulating tumor cells: transcriptional heterogeneity and diversity from breast cancer cell lines," *PLoS One* 2012; 7:e33788). We have developed microfluidic single-cell analysis systems including microfluidic bacterial rRNA flow-FISH and cell signaling pathway profiling (Liu P et al., "Microfluidic fluorescence in situ hybridization and flow cytometry (muFlowFISH)," *Lab Chip* 2011; 11:2673-9; and Wu M et al., "Microfluidically-unified cell culture, sample preparation, imaging and flow cytometry for measurement of cell signaling pathways with single cell resolution," *Lab Chip* 2012; 12:2823-31). Here, we discuss a novel ten-chamber microfluidic chip platform for multiplexed detection of miRNA and proteins in single cells under ten different experimental conditions simultaneously.

To study miRNAs at single-cell resolution, we have developed a novel microfluidic approach, where flow fluorescent in situ hybridization (flow-FISH) using locked-nucleic acid (LNA) probes is combined with rolling circle amplification to detect the presence and localization of miRNA. Instead of using tyramide signal amplification to visualize the miRNA-LNA probe duplex, we used rolling circle amplification (RCA) of the target miRNA signal to achieve robust and reliable signal amplification. The RCA amplification reagent has been previously used to detect proteins both in lysates and in cells (Gullberg M et al., "Cytokine detection by antibody-based proximity ligation," *Proc. Nat'l Acad. Sci. USA* 2004; 101:8420-4; and Leuchowius K J et al., "In situ proximity ligation assay for microscopy and flow cytometry," *Curr. Protoc. Cyton.* 2011; Chapter 9:Unit 9.36). In addition, RCA has a limit of detection between $10^{-14}$ to $10^{-13}$ molar (Gustafsdottir S M et al., "Proximity ligation assays for sensitive and specific protein analyses," *Anal. Biochem.* 2005; 345:2-9), providing the necessary sensitivity for detection of miRNA in single cells.

Furthermore, our flow cytometry approach allows analysis of gene-products potentially targeted by miRNA together with the miRNA in the same cells. Thus, an added benefit of LNA-Flow FISH is the possibility of multiplexing with protein immunostaining in the same cell. As described herein, we multiplexed miRNA detection with immunostaining of a protein to show the multiplexing capability.

We demonstrate our method in Jurkat cells, a model cell line for the study of T cell activation (Weiss A et al., "The role of T3 surface molecules in the activation of human T cells: a two-stimulus requirement for IL 2 production reflects events occurring at a pre-translational level," *J. Immunol.* 1984; 133:123-8). 12-O-tetradecanoylphorbol 13-acetate (PMA) and ionomycin were employed to trigger T cell activation, which leads to production of transmembrane glycoprotein CD69 and up-regulation of miR155 (Marzio R et al., "CD69 and regulation of the immune function," *Immunopharmacol. Immunotoxicol.* 1999; 21:565-82; and Lu L F et al., "Foxp3-dependent microRNA155 confers competitive fitness to regulatory T cells by targeting SOCS1 protein," *Immunity* 2009; 30:80-91).

We visualized and quantified PMA- and ionomycin-induced CD69 and miR155 in Jurkat cells using both microscopy and flow cytometry, demonstrating simultaneous detection of miRNA and a target protein in the same cell. CD69 is a lectin C-type protein that is involved in T cell differentiation through the Jak3/Stat5 pathway, and is the earliest inducible surface protein indicative of T cell activation (Martin P et al., "CD69 association with Jak3/Stat5 proteins regulates Th17 cell differentiation," *Mol. Cell. Biol.* 2010; 30:4877-89). miR155 up-regulation in T cells is implicated in the negative regulation of SOCS1 protein, which leads to increased levels of interleukin-2, a cytokine necessary for T cell proliferation (Lu L F et al., *Immunity* 2009; 30:80-91). The flow-FISH method herein was completed in ~ten hours, utilizes only 170 nL of reagent per experimental condition, and is the first to directly detect miRNA in single cells using flow cytometry.

Materials and Methods

Microfluidic chip design and platform setup: The ten-chamber microfluidic chip was designed in-house using AutoCAD 2010 (Autodesk Inc., San Rafael, Calif.), photomasks were generated at Photo Sciences (Torrance, Calif.), and quartz microfluidic devices were fabricated by Caliper Life Sciences (Hopkinton, Mass.). An array of fourteen holes (500 μm in diameter, seven on each side) provided for fluid inlets and outlets. Each serpentine chamber was individually addressable to allow ten different conditions per experiment. The ten-chamber chip was situated in a manifold with 14 pumps and valves (FIG. 2B-2C) that used positive pressure to drive the movement of cells and reagents on and off the chip. The chip and manifold were placed in a custom micro-flow cytometer for flow cytometric analysis (FIG. 2D).

The device in this study contained ten horizontal fluidically isolatable microchannels with the following dimensions: width of 200 μm, depth of 30 μm, and length of 72 mm, with each holding from 500 to 2000 cells and 170 nL to 220 nL of fluid volume. Additional steps in chip packaging and details of the chip platform are described in, e.g., Wu M et al., *Lab Chip* 2012 Aug. 21; 12(16):2823-31.

Cell culture and stimulation: Jurkat cells were purchased from ATCC (TIB-152) and cultured in RPMI media (11875-093; Invitrogen, Carlsbad, Calif.) containing 10% FBS (100-500; Gemini, and 0.5 mg/ml penicillin and streptomycin (Ser. No. 15/240,062; Invitrogen). For stimulation of Jurkat cells, cells were seeded at $1 \times 10^6$/ml for 0, 8, 16, 20, or 24 hours with 10 ng/ml phorbol 12-myristate 13-acetate (PMA) (P8139; Sigma) and 1 μM ionomycin (13909; Sigma). After stimulation, the Jurkat cells were fixed with 8% paraformaldehyde (PFA, Electron Microscopy Sciences, Hatfield, Pa.) in phosphate-buffered saline (PBS) for 10 min. Fixed cells were pelleted at 300 g for 5 min. and washed twice with PBS. If needed, after stimulation, $5 \times 10^5$ cells from each condition can be set aside for RNA extraction and RT-qPCR.

RT-qPCR: $5 \times 10^5$ cells from each condition were set aside prior to fixation and pelleted at 300 g for 5 min. and washed twice with PBS. Total RNA was extracted using the RNeasy kit from Qiagen according to manufacturer's instructions. The extracted RNA was quantified using a Nanodrop 2000, and 100 ng of RNA was used to generate cDNA using the miScript II RT kit (Qiagen). All steps were performed according to manufacturer's instructions. 100 ng of cDNA from each condition was subsequently used in miScript hsa-mir-155 primer assay (Sanger accession: MI0000681, Qiagen), normalized to positive control SNORD61 (Qiagen). Expression level of miRNA155 was analyzed using the 2-ΔΔCt method. SNORD61 served as a positive control for normalization. miR155 level at 0 h. served as basal level, and miR155 in PMA and ionomycin treated samples are expressed as fold changes compared with 0 hours.

Microchip surface treatment with Cell-Tak™ to reversibly capture nonadherent cells: The planar microfluidic cell preparation chip in this study contained ten fluidically-isolatable chambers. The ten-channel microchip was cleaned with 10% bleach in filtered, deionized (DI) water for 15 min., followed by flushing with DI water to wash off all residual bleach. The working Cell-Tak™ solution (354240; BD Biosciences, San Jose, Calif.) was prepared by combining 15 μL of Cell-Tak™ with 575 μL of 0.1 M sodium bicarbonate (pH 8.0), followed by adding 10 μL of 1 N NaOH immediately prior to adsorption onto the chip. Freshly made working Cell-Tak™ solution was continuously driven into all ten-cell holding chambers of the device for at least 15 min. to thinly coat the microchannels with Cell-Tak™, followed by PBS wash for 5 min. to remove excess Cell-Tak™ from the microchannels. The coated devices were used within one day. Fixed Jurkat cells were introduced into the Cell-Tak™ coated chip and captured on the microchannel surface for ISH.

On-chip LNA in situ Hybridization: The miR155 probe had the following sequence: /5DigN/ACCCCTATCAC-GATTAGCATTAA/3Dig_N/ (SEQ ID NO:1), and the scrambled probe had the following sequence: /5DigN/GT-GTAACACGTCTATACGCCCA/3Dig_N/ (SEQ ID NO:2). These LNA double DIG-labeled probes were purchased from Exiqon A/S, Vedbaek, Denmark. Fixed Jurkat cells were loaded into the chip, and allowed to settle and adhere to the microchannel surface for 30 min. During the settling time, the following solutions were freshly prepared: Solution 1 (0.13 M 1-methylimidazole, 300 mM NaCl, pH 8.0, adjusted with HCl), Solution 2 (0.16 M EDC in solution 1, adjusted to pH 8.0); and hybridization buffer (50% formamide, 2×SSC, 50 μg/ml yeast tRNA, 50 μg/ml salmon sperm DNA, 50 mM NaPi). To permeabilize the Jurkat cells, 0.25% Triton™ X-100 in TBS was flown into all chambers for 10 min., followed by a 5 min. wash with solution 1. After incubation with Solution 1, Solution 2 was flown into all chambers and cells were incubated for 20 min. at room temperature (RT), followed by a 5 min. wash with TBS. The cells were then pre-hybridized for 30 min. at 62° C. in hybridization buffer (pre-warmed to 65° C.). All LNA probes were used at 10 pmol/25 μl hybridization buffer. Hybridization of LNA probes was performed at 80° C. for 90 seconds (s.), followed by 90 min. at 62° C. Following LNA probe hybridization, all chambers were washed with 2×SSC with 50% formamide at 65° C. for 10 min. (flow 5 min., stop 5 min.), then washed with 1×SSC for 20 min. (flow 5 min., stop 15 min.) at RT, and finally washed with 0.1×SSC for 20 min. (flow 5 min., stop 15 min.) at RT.

Signal amplification using rolling circle amplification: The FITC Duolink® anti-mouse PLUS probe (92001-0030), Duolink® anti-mouse MINUS (92004-0030) probe, and Duolink® detection kit (92014-0030) from Olink Biosciences AB (Uppsala, Sweden) were used to perform rolling circle amplification of miRNA signals as previously described (Wu M et al., *PLoS One* 2013; 8(1):e55044).

After in situ hybridization (ISH) with DIG-labeled LNA probes, the cells were blocked with 2% bovine serum albumin (BSA) for 30 min. at 37° C. and incubated with anti-DIG antibody (11333062910; Roche, Indianapolis, Ind.) at 1:50 for 1 h. at 37° C. Cells were then washed with TBS with 0.05% Tween 20 (TBST) for 5 min. The detection of the miRNA/LNA probe duplex was accomplished by amplifying the anti-DIG antibody bound to the DIG labels on the LNA probes. The Duolink® anti-mouse PLUS and MINUS probes were diluted 1:5 (20 μL PLUS, 20 μL MINUS, and 60 μL dilution buffer from kit) and incubated with cells for 1 h. at 37° C. After incubation, all chambers were washed for 5 min. with TBST, and the subsequent ligation and amplification steps were done according to the manufacturer's instructions by using only one reaction volume for all ten chambers. After on-chip sample preparation, cells were detached via proteolytic cleavage using 100 μg/ml elastase (I.U.B.: 3.4.21.36, Worthington) and hydrodynamically focused for on-chip flow cytometry.

CD69 protein immunostaining multiplexed with LNA Flow-FISH: To multiplex protein immunostaining with LNA flow-FISH, Jurkat cells were stained with anti-CD69-biotin antibody at 1:100 (13-0699-80, eBioscience) in PBS for 30 min. at RT prior to permeabilization with 0.25% Triton™ X-100. A solution of CD69 antibody was flown into all chambers, flow was then stopped for 30 min. for incubation. All chambers were washed with TBS with 0.05% Tween for 5 min., followed by 30 min. incubation with a 1 nM solution of Qdot® 705-streptavidin conjugate (Q10161MP, Invitrogen) in PBS. Following Qdot® 70-streptavidin incubation, all chambers were washed with TBST for 5 min. All chambers were then washed with TBST for 5 min. The in situ hybridization procedure continues from this point on at the permeabilization step.

Microscopy and image analysis: Prior to imaging, the cells were incubated with Hoechst stain (33342, Pierce) in PBS for 10 min., followed by a 10 min. wash in PBS. Epi-fluorescent images were captured at 60× magnification on an Olympus IX-71 microscope equipped with GFP, Texas Red, DAPI filters and Hamamatsu ORCA-R2 cooled CCD camera controlled via free micro-manager software. Images were artificially colored and overlaid in ImageJ.

On-chip laser induced fluorescence and flow cytometry: A 20-mW diode pumped solid-state laser at 488 nm (85-BCF-020-112; CVI Melles Griot, Carlsbad, Calif.) in an epifluorescence configuration was used for excitation (see Wu M et al., PLoS One 2013; 8(1):e55044). The laser beam was reflected and focused upon the detection region using a long pass dichroic mirror (LPD01-488S; Semrock, Rochester, N.Y.) and an aspheric lens (5722-H-B; New Focus, Santa Clara, Calif.), respectively. Forward scattering was collected and channeled to the active area of a photomultiplier tube (PMT) based detector (H5784-20; Hamamatsu, Bridgewater, N.J.) using a custom-made sculpted tip silica optical fiber (1000 μm core, 2000 μm sculpted spherical tip (Polymicro Technologies, Phoenix, Ariz.). Laser-induced fluorescence emission was first collected via the same aspheric lens used for focusing and subsequently passed on for detection via the dichroic mirror used in the excitation leg of the apparatus as described above.

For multiplexed detection, an eight channel Hamamatsu linear multi-anode (LMA) PMT coupled with filter optics (H9797TM; Hamamatsu, Bridgewater, N.J.) was used. Only four channels of the LMA PMT were used in this configuration, and the filtering was selected for green, yellow, red, and far-red fluorescence detection. The green fluorescence was detected using longpass dichroic mirror (DMT560: Hamamatsu, Bridgewater, N.J.) and a bandpass filter (BPF534_30). For yellow fluorescence detection in the second channel, longpass dichroic mirror (DMT650) and bandpass filter (BPF585_40). Red fluorescence was detected third channel of the LMA PMT via a longpass dichroic (DMT740) and filtered using a third bandpass filter (BPF692_40). Finally, far-red fluorescence detection was accomplished by cascading the remaining florescence signal onto the fourth LMA PMT channel using a mirror, and filtered onto that channels detection region using a fourth bandpass filter (BPF785_62).

Data acquisition was performed for all five photomultiplier voltages (488 nm scatter, green, yellow, red, and far red) by a data acquisition module (NI USB-6259; National Instruments, Austin, Tex.). In-house software for data acquisition and recording was scripted using LabVIEW, and the data were further analyzed and processed using a custom "Peak Finder" application also scripted using LabVIEW. The Peak Finder application fit the peak of the raw voltage signals from the PMT with a polynomial fit and generated the peak amplitude and width values.

Results and Discussion

Microfluidic platform and assay design: A ten-chamber microfluidic chip was designed for sample preparation and on-chip flow cytometry (FIG. 3A, left). The chip had fluidically-isolatable chambers, each capable of holding up to 2000 cells. The microchannel surfaces were pre-coated with Cell-Tak™ solution to facilitate capture of non-adherent Jurkat cells for the on-chip hybridization and immunostaining. After sample preparation, the cells in the chambers are detached using proteolytic cleavage, and driven by positive pressure to the center of the chip where they are hydrodynamically focused (FIG. 3A, right) and interrogated using micro-flow cytometry using a custom built setup (FIG. 2D).

Our microfluidic platform's ultra-low reagent consumption substantially reduces the cost of LNA flow-FISH (~100-fold reduction from ~$150/sample to <$1.50/sample). The flow-FISH assay uses a novel combination of LNA probes with RCA signal amplification for a robust miRNA signal that can be quantified by flow cytometry as well as visualized by microscopy.

A schematic depicting the miRNA LNA Flow-FISH method is shown in FIG. 4A. Once the cells are loaded into the chambers and captured by Cell-Tak™, miR155 LNA probe with digoxigenin (DIG) conjugated to both 5' and 3' termini was hybridized to mature intracellular miR155. After the LNA probe hybridizes with miR155, monoclonal anti-DIG antibodies (anti-DIG mAb) bound the DIG labels at both ends of the LNA probe. A pair of antibody/oligonucleotide probes (one positive and one negative proximity ligation probes) was used to bind to the anti-DIG antibodies. After binding to the anti-DIG antibody, the two antibody/oligonucleotide probes were ligated with two additional oligonucleotides (connector probes) to form a circular template for the subsequent rolling circle amplification with Phi29 bacterial polymerase. FITC-labeled oligonucleotide detection probes complementary to the ligated circular template were hybridized with the resultant circular concatemers. Each RCA amplified LNA-probe/miRNA duplex became visible as fluorescent dots (FIG. 6A) and can also be detected by flow cytometry. RCA amplification provided improved signal specificity because it occurs only when a circular template is generated, and the detection of the circular product was accomplished using sequence-specific hybridization probes.

Figure 5A:
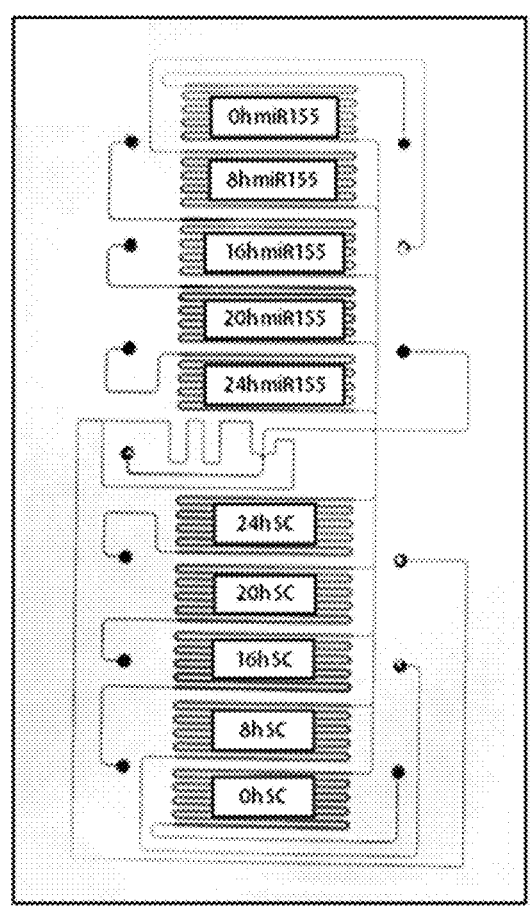
FIG. 5A-5D provides Flow-FISH detection of a target nucleic acid (miR155). Shown are (A) a schematic of the microfluidic device and assay conditions; (B) a graph showing the frequency of miR155-labeled cells, which were detected by fluorescence and flow cytometry, after stimulation with PMA and ionomycin for 0, 8, 16, 20, or 24 h.; (C) a graph showing median miR155 fluorescence after stimulation for 0, 8, 16, 20, or 24 h., where * indicates $p<0.01$ and  indicates $p>0.01$; and (D) a graph showing fold change in RT-qPCR amplicons after stimulation for 0, 8, 16, 20, or 24 h., where  indicates $p>0.01$ and * indicates $p<0.01$.
Figure 6A:
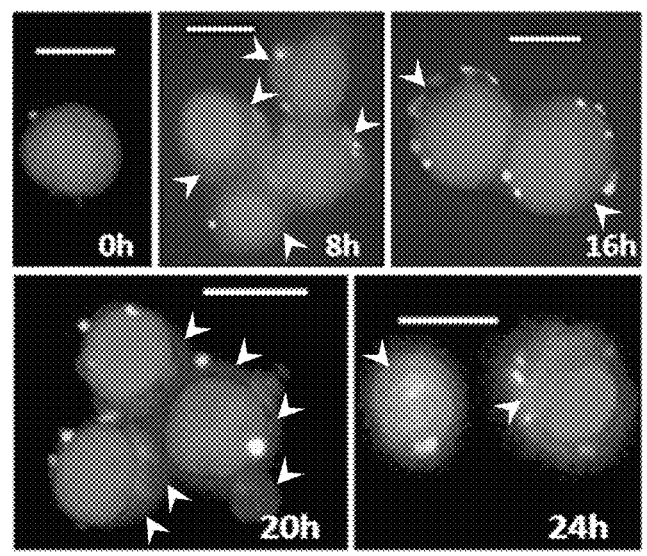
FIG. 6A-6C provides on-chip multiplexed detection of a target nucleic acid (miR155) and a target protein (CD69). Shown are (A) fluorescence microphotographs of Jurkat cells showing RCA-amplified miR155 signals in the cytosol (shown as dots) and CD69 protein stained with quantum dots (peripheral edges indicated by white arrowheads); (B) a graph showing median miR155 fluorescence (diamonds) and median CD69 fluorescence (circles) collected via on-chip flow cytometry; and (C) a scatter plot showing heterogeneity of miR155 and CD69 expression in individual Jurkat cells after 24 hours stimulation with PMA and ionomycin. Each cell is indicated by a data point (diamond).
Figure 6B:
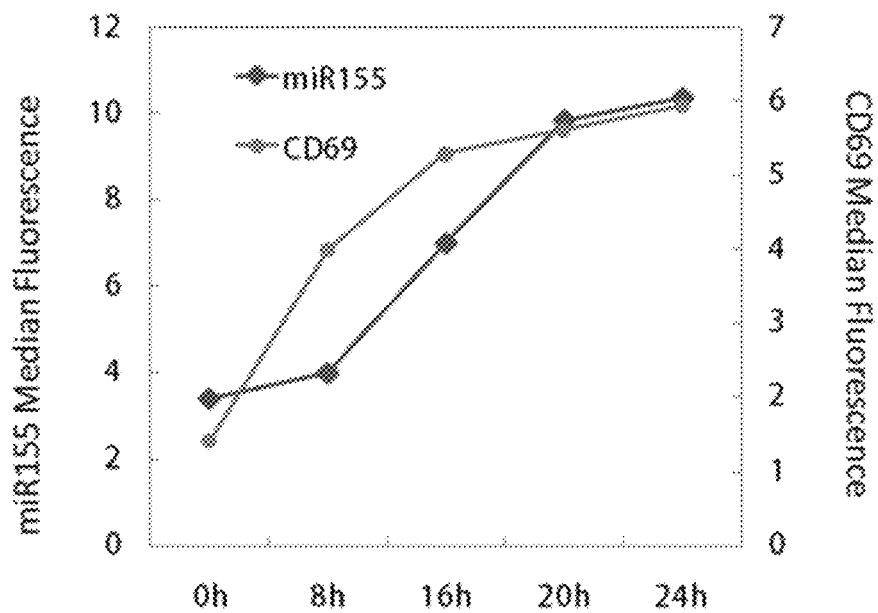

LNA Flow-FISH analysis of PMA and ionomycin induced miR155 upregulation: To track the expression of PMA and ionomycin induced miR155 over time, Jurkat cells were stimulated with PMA and ionomycin (for 0, 8, 16, 20, and 24 h.) and then loaded in duplicate into the ten chamber chip (FIG. 5A). The top five chambers were hybridized with double DIG-labeled miR155 LNA probe, and the bottom five chambers were hybridized with double DIG labeled random scrambled probe as negative control (labeled "SC" in FIG. 5A).

Figure 5B:
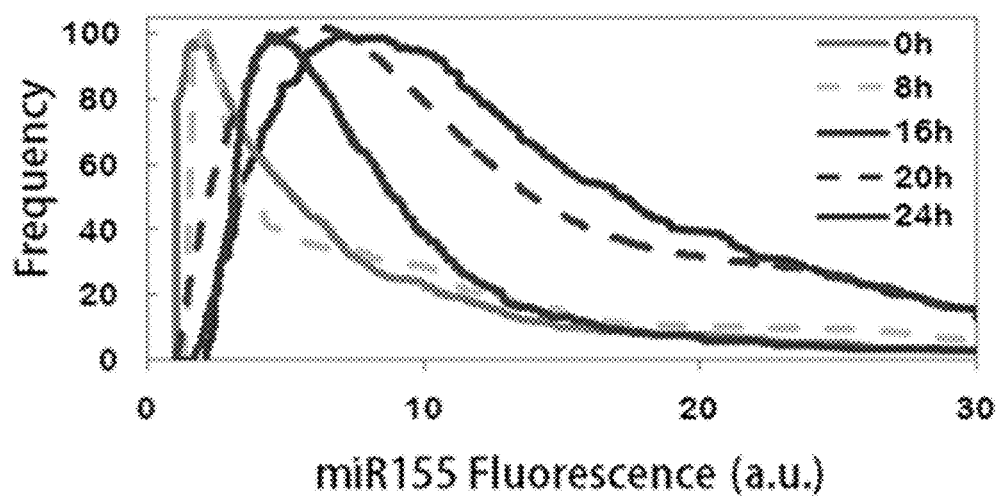

The RCA-amplified miR155 fluorescence was quantified using on-chip flow cytometry, and the fluorescence histograms were overlaid (FIG. 5B). The normalized median fluorescence values from three separate experiments were plotted as percent of maximal fluorescence from each sample (FIG. 5C).

Figure 5C:
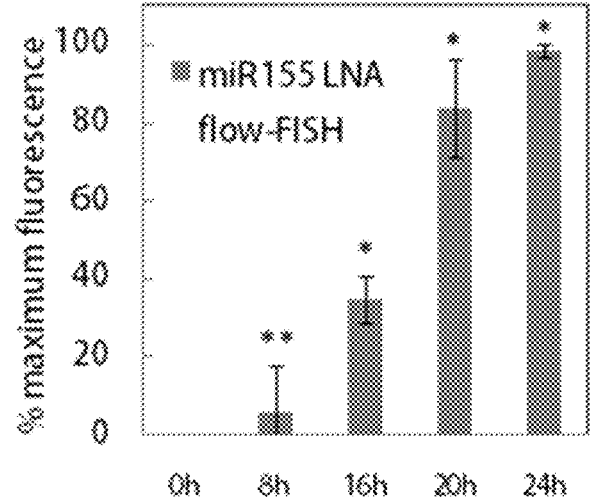
Figure 5D:
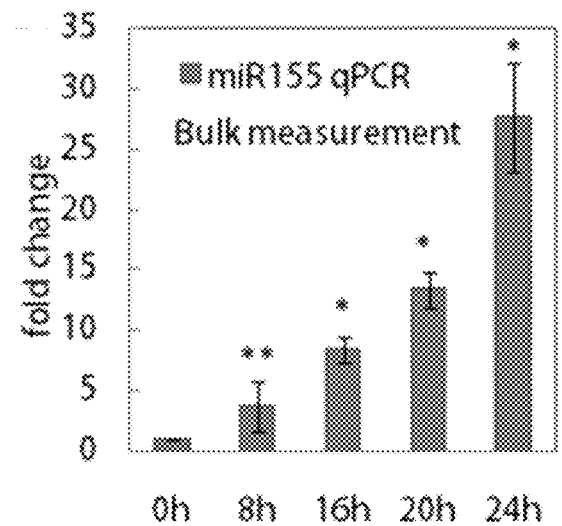

Both the overlay in FIG. 5B and the bar graph of median values in FIG. 5C showed an incremental increase in miR155 for Jurkat cells under stimulation with PMA and ionomycin. Hybridization to the random scrambled probe produced low level of background fluorescence that remained constant throughout the time course, and the background was subtracted from the miR155 measurements. The miRNA flow-FISH results were verified using population RT-qPCR analysis and calculated relative fold change from 0 h. (FIG. 5D).

Both flow-FISH and qPCR showed that miR155 increased significantly from 0 h. at 16 h., 20 h., and 24 h., with p values <0.01; miR155 increased from 0 to 8 h., but the change was not statistically significant (p>0.1). The upregulation of miR155 by PMA and ionomycin detected by our LNA flow-FISH method corroborated the existing findings of miR155 upregulation in activated T cells and not in resting T cells (Thai T H et al., "Regulation of the germinal center response by microRNA-155," Science 2007; 316: 604-8).

Multiplexed analysis of CD69 protein expression and miR155 upregulation: The high melting temperature of LNA probes provides superior specificity and rapid hybridization for detecting small miRNAs, but the high hybridization temperature can reverse formaldehyde fixation, and miRNAs can be washed away. A second fixation step (FIG. 4B) using 1-ethyl-3-(3-dimethyl-aminopropyl) carbodiimide (EDC) was performed subsequent to formaldehyde fixation to irreversibly cross-link the miRNA to the neighboring amino acid residues (see, e.g., Pena J T et al., Nat. Methods 2009; 6:139-41). As seen in FIG. 4B, the 5'-phosphate of miRNA was activated by EDC to form an intermediate, which was cross-linked to neighboring amino groups of proteins. The fixation with EDC allowed irreversible cross-linking that tethered miRNAs inside the cells during the high temperature hybridization conditions with LNA containing probes. The EDC fixation step retained miRNAs inside the cell but destroyed protein epitopes and protein based fluorophores, such as phycoerythrin.

To solve this problem, we used quantum dot labeled secondary antibody for multiplexed protein detection with LNA flow-FISH because quantum dots are inert to EDC fixation. Immunostaining with anti-CD69 antibody and Qdot® 705-labeled secondary antibody was performed prior to fixation by EDC. At time 0, no CD69 and almost no miR155 can be seen. The size and intensity of green miR155 dots increase as duration of stimulation increases. After microscopy, the cells were detached and analyzed using flow cytometry (FIG. 6A), the median fluorescence values from miR155 and CD69 are plotted in the same graph (FIG. 6B), showing increase of both miR155 and CD69 under PMA and ionomycin stimulation. Significant CD69 induction was detected 8 h. post stimulation. miR155 upregulation occurred later than CD69 protein induction, detectable starting at 16 h., indicating that signaling events surrounding CD69 protein induction was activated earlier by PMA and ionomycin than those that lead to miR155 up-regulation.

CONCLUSION

Figure 6C:
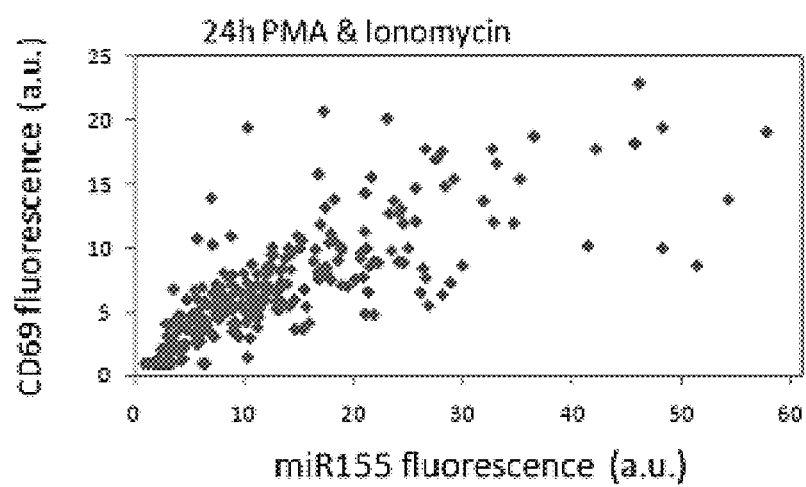

We have developed a novel flow-FISH method for measuring relative miRNA changes at single-cell resolution using a ten-chamber microfluidic chip platform. The biggest advantage of the flow-FISH method is the capability to multiplex the detection of miRNAs with protein immunostaining in the same cell, and preserve the cell-to-cell heterogeneity within the population (FIG. 6C). While we have shown detection of a single protein, it is possible to detect multiple proteins in the same cell using antibodies labeled with different fluorophores or quantum dots. This multiplexing capability opens up many potential applications for miRNA flow-FISH in both clinical and basic biological sciences. One potential clinical application is the profiling of miRNA levels in complex clinical samples such as peripheral blood mononuclear cells (PBMCs) from patients with leukemia or autoimmune disorders. The expression level of up to ten different miRNA in ten immune subsets can be analyzed in one microfluidic chip experiment. miRNA expression levels in many different cell types can be assessed and tracked as biomarkers indicative of disease progression or response to therapy. If miRNA copy number quantitation is required for development of a specific clinical diagnostic assay, custom flow-FISH quantitation beads can be developed by conjugating known numbers of synthetic miRNAs onto polystyrene beads. The calibration beads can be captured on the chip, hybridized to the same LNA FISH probe, and amplified on the chip along with experimental samples under the same conditions to provide a standard curve from which the miRNA copy number per cell can be determined.

For application in basic science, miRNA flow-FISH can be used to develop functional assays for the discovery of miRNA targets in vivo. One miRNA and dozens of its putative mRNA and protein targets can be simultaneously quantified using a combination of LNA flow-FISH for miRNAs, traditional flow-FISH for the mRNAs, and immunostaining for the proteins. Time course experiments tracking the miRNA and target mRNA/protein levels in the presence of miRNA antagonists or mimics can validate mRNA and protein targets in vivo. Finally, since we have already successfully demonstrated the spatiotemporal profiling of protein signaling pathway using a microfluidic platform, combining miRNA flow-FISH with cell signaling pathway profiling will provide a comprehensive look into the relationship between miRNAs and the cell signaling pathways they modulate.

Example 3: Protocol for miRNA Detection at Single-Cell Resolution Using Microfluidic LNA Flow-FISH Flow cytometry in combination with fluorescent in situ hybridization (flow-FISH) is a powerful technique that can be utilized to rapidly detect nucleic acids at single-cell resolution without the need for homogenization or nucleic acid extraction. Here, we include instructions on how to set up a microfluidic device sample preparation station to prepare cells for imaging and analysis on a commercial flow cytometer or a customized built micro-flow cytometer.

Flow-FISH is a method that was first developed by adapting Q-FISH or quantitative fluorescence in situ hybridization for use in suspended cells followed by analysis with flow cytometry to measure the length of telomeres (Rufer N et al., "Telomere length dynamics in human lymphocyte subpopulations measured by flow cytometry," Nat. Biotechnol. 1998; 16(8): 743-7). Flow-FISH is an enormously useful technique because it provides single-cell resolution data from a mixed population of cells, but it is labor intensive and cumbersome, requiring hybridization times of up to several days, which makes reliable detection of vulnerable RNA species very challenging.

To improve the workflow as well as reliability of flow-FISH, a new class of oligonucleotide analogues called locked nucleic acids (LNA) with the ribose ring constrained by a methylene bridge between the 2'-oxygen and the 4'-carbon, has been incorporated into FISH probes to provide drastically improved hybridization characteristics (Silahtaroglu A N et al., "FISHing with locked nucleic acids (LNA): evaluation of different LNA/DNA mixmers," *Mol. Cell. Probes* 2003; 17(4):165-9). The methylene bridge in LNA molecules reduces the conformational flexibility of the ribose ring, resulting in +1 and +2° C. of thermal stability per LNA monomer in LNA/DNA mixed nucleotide probes during Watson-Crick base-pairing (Kumar R et al., "The first analogues of LNA (locked nucleic acids): phosphorothioate-LNA and 2'-thio-LNA," *Bioorg. Med. Chem. Lett.* 1998; 8(16):2219-22). The LNA containing probe's high affinity enables the experimenter to decrease hybridization time from days to <2 hours, and significantly increase hybridization temperature to reduce signal to noise ratio.

Since the advent of LNA probes, LNA flow-FISH has been adapted to detect messenger RNA (mRNA), viral RNA, and bacterial RNA (see, e.g., Robertson K L et al., "LNA flow-FISH: a flow cytometry-fluorescence in situ hybridization method to detect messenger RNA using locked nucleic acid probes," *Anal. Biochem.* 2009; 390(2):109-14; Robertson K L et al., "Monitoring viral RNA in infected cells with LNA flow-FISH," *RNA* 2010; 16(8): 1679-85; and Robertson K L et al., "Locked nucleic acid and flow cytometry-fluorescence in situ hybridization for the detection of bacterial small noncoding RNAs," *Appl. Environ. Microbiol.* 2012; 78(1):14-20).

While LNA probes provide undeniable improvement to the flow-FISH method, there are other improvements to be made. The necessity of centrifugation to wash suspended cells greatly contributes to sample loss, thus making the detection of mammalian small non-coding RNA or other very rare RNAs difficult, due to the need to incorporate a signal amplification step with many reagent changes and washes, and thus many more centrifugation steps.

Another weakness of the existing LNA flow-FISH method is that it is not optimized for multiplexed detection of nucleic acids along with proteins, which limits the scope of information that can be gathered using the technique. Until recently, only conventional FISH using tyramid signal amplification (TSA) to amplify the small RNA signal in adherent cells or tissue sections can multiplex the detection of small non-coding RNAs and proteins in single cells (de Planell-Saguer M et al., *Nat. Protoc.* 2010; 5:1061-73).

Conventional FISH is labor intensive and time consuming, both in terms of sample preparation and analysis via microscopy. In addition, TSA amplification of miRNA signals can be difficult to reproduce due to non-specific enzymatic amplification of signal. Here, we present a method to significantly advance LNA flow-FISH by combining FISH with rolling circle amplification in a microfluidic sample preparation chip to integrate novel biochemistries to monitor miRNAs and proteins at single-cell resolution. Microfluidic sample preparation allows the elimination of centrifugation steps that contributes to sample loss, and the minute reagent and cell requirement makes optimization of molecular assay chemistries possible, while keeping the costs to ~5% of bench scale reactions. By using isothermal rolling circle amplification of miRNA signals, the microfluidic LNA flow-FISH method is fully compatible for multiplexing nucleic acid detection with protein immunostaining in the same cell.

Microfluidic sample preparation have been used to study proteins, genomes, bacteria, and rare cancer cells at single-cell resolution (see, e.g., Wu M et al., *Curr. Opin. Biotechnol.* 2012 February; 23(1):83-8; Wu M et al., *Lab Chip* 2012 Aug. 21; 12(16):2823-31; Liu Y et al., "Single-cell measurements of IgE-mediated FcεRI signaling using an integrated microfluidic platform," *PLoS One* 2013; 8(3):e60159; Yilmaz S et al., "*Curr. Opin. Biotechnol.* 2012; 23:437-43; Liu P et al., *Lab Chip* 2011; 11:2673-9; and Powell A A et al., "*PLoS One* 2012; 7:e33788). The challenge to incorporate microfluidics into traditional molecular biology lab can now be overcome with the use of commercially available microfluidic chips and fluid control components.

This example provides a schematic for building and using simple microfluidic systems for cell analysis, with minimal need for previous expertise in microfluidic engineering. To demonstrate the microfluidic technique, we demonstrate the detection of miR155 and CD69 in activated Jurkat cells as illustration of the microfluidic miRNA flow-FISH method.

Reagents for On-Chip LNA FISH Sample Preparation

Unless otherwise stated, prepare all reagents in nuclease-free tubes; and use nuclease-free ultrapure water that is not DEPC treated. If it is not possible to work in an RNase-free area, diligently wipe down all surfaces and pipets intended for the experiment with RNase Away (Molecular Bioproducts, San Diego, Calif.) before starting the experiment. Always wear fresh gloves and change gloves frequently to prevent RNase contamination. The volumes presented here are intended for microfluidic chip based sample preparation.

Reagents included as follows:

0.1×SSC: 250 µl of 20×SSC with 49.75 ml of $H_2O$ in a 50 ml conical tube, mixed well by inverting, and stored at room temperature (RT);

3 M NaCl: 8.766 g of NaCl with 25 ml of $H_2O$, vortexed well to dissolve NaCl completely, brought to a total volume of 50 ml with $H_2O$, and stored at RT;

50% formamide in 2×SSC: 1 ml of 20×SSC with 4 ml of $H_2O$ and 5 ml of formamide in a 15 ml conical tube, and stored at 4° C. in a tube wrapped in foil;

1 M NaPi (pH 7.0): 2.68 g of $Na_2HPO_4.7H_2O$ [=sodium phosphate, dibasic, heptahydrate] with 200 µl of $H_3PO_4$ [=o-phosphoric acid, 85%], brought to a 50 ml total volume with $H_2O$, sterile filtered, and stored at RT;

hybridization solution (makes 10 ml): 5 ml of formamide with 3.5 ml of $H_2O$, 1 ml of 20×SSC, 50 µl of 10 µg/µl salmon sperm, 10 µl of 500 µm/ml yeast tRNA, and 50 mM NaPi (500 µl of 1 M stock), which was divided into 500 µl aliquots, and stored at −20° C.;

10% bleach: 5 ml of bleach with 45 ml of $H_2O$, sterile filtered using a 0.22 µm Steriflip filter (Millipore, Billerica, Mass.), and stored at RT;

50 ml of deionized $H_2O$, sterile filtered using Steriflip filter, and stored at RT;

1 mg/ml phorbol 12-myristate 13-acetate (PMA) (Sigma, St. Louis, Mo.): 1 ml of DMSO with 1 mg size vial of PMA, mixed well by vortexing after replacing cap, and stored as 50 µl aliquots at −20° C.;

8% paraformaldehyde (PFA): dilute 5 ml of 16% PFA (Electron Microscopy Science, Hatfield, Pa.) with 5 ml of PBS immediately before use, where, once opened, the 16% PFA solution should be stored at 4° C. in a 15 ml conical tube wrapped in foil and be used for up to 1 week after opening;

0.1 M $NaHCO_3$ solution (pH 8.0): 4.1 g of $NaHCO_3$ with 50 ml of $H_2O$, sterile filtered, and stored at RT;

1 N NaOH: 4 g of NaOH with 1 L of $H_2O$ ($H_2O$ need not be nuclease free), stored at RT;

Solution 1 (makes 3.2 ml): 32 µl of 1-methylimidazole (stored in a desiccator) with 2.839 ml of H$_2$O, 320 µl of 3 M NaCl, and 9 µl of 12 M HCl, which was mixed well by vortexing and made fresh for each experiment;

Solution 2 (makes 1 ml): 30 mg of EDC (~30 mg weighed out into 1.7 ml eppendorf tubes and stored in a desiccator at −20° C., which was used within 3 months after storage) with 1 ml of Solution 1, which was made fresh for each experiment;

Working Cell-Tak™ solution (BD Biosciences, Bedford, Mass.): 20 µl of Cell Tak™ with 570 µl NaHCO$_3$ (pH 8.0), which was made fresh for each experiment; and 500×PMA and ionomycin (Sigma-Aldrich, St. Louis, Mo.) working solution: diluted 1 mg/ml PMA in DMSO at 1:100 into PBS to make 10 µg/ml PMA, combined 50 µl of 10 µg/ml PMA with 50 µl of 1 mM ionomycin to make 500× working solution, which was made fresh each experiment.

Reagents for LNA FISH Probe

Pre-designed LNA containing ISH probes for miRNA targets can be purchased from Exiqon A/S. When selecting probes for miRNA LNA flow-FISH, purchased LNA probes were labeled with DIG on both N and C termini for the strongest signal amplification. When analyzing more abundant RNA species such as mRNAs of structural genes, only one hapten label per probe is sufficient. Exiqon supplied LNA probes as 25 µM stock in water. To these initial stock solutions, nuclease free water was added to the tube to make 10 µM LNA probe stock, divided into 5 µl aliquots, and stored at −20° C. The LNA probes for miR155 and its scrambled control included the double DIG-labeled miR155 sequence of 5/DigN/ACCCTATCACGATTAGCATTAA/3Dig_N (SEQ ID NO:1); and the double DIG-labeled scrambled control sequence of 5/DigN/GTGTAACACGTCTATACGCCCA/3Dig_N (SEQ ID NO:2).

Antibodies Suitable for Multiplexing with LNA Flow-FISH

Quantum dot pre-labeled secondary antibodies can be purchased from Invitrogen™ of Life Technologies, Corp. Custom labeling of primary antibodies can be done by using one of several Q-dot antibody labeling kits, also available through Invitrogen™. Antibodies included biotin-labeled anti-CD69 antibody (eBiosciences, San Diego, Calif.) and Qdot® 705-conjugated streptavidin (Invitrogen, Carlsbad, Calif.).

Reagents for Rolling Circle Amplification (RCA)

The RCA reaction was conducted using an antibody to bind the LNA probe, as well as additional nucleic acid sequences to form the circular template and fluorophore labels for detection. In particular, reagents for RCA included anti-DIG antibody (Roche Diagnostics, Indianapolis, Ind.); FITC-labeled Duolink® mouse PLUS and MINUS probes (Olink Bioscience AB, Uppsala, Sweden), such as Duolink® In Situ PLA® Probe Anti-Mouse PLUS and Duolink® In Situ PLA® Probe Anti-Mouse MINUS (Sigma-Aldrich); Green detection kit (Olink Biosciences, Uppsala, Sweden), such as Duolink® In Situ Detection Reagents Green (Sigma-Aldrich), and TBST buffer, which included 1.21 g of Tris base, 4.38 g of NaCl, 0.25 ml of Tween 20, with 40 ml of H$_2$O. For the TBST buffer, the pH was adjusted to 7.6, and then the total volume was brought to 50 ml with H$_2$O.

Reagents for Cell Detachment

As described herein, test samples containing cells were captured by using Cell-Tal™, a commercially available tissue adhesive containing polyphenolic proteins extracted from *Mytilus edulis* (a marine mussel), which is then formulated in 5% acetic acid. These proteins can contain large amounts of hydroxyproline (Hyp) and 3,4-dihydroxyphenylalanine (Dopa). Any enzyme or chemical agent can be employed that preferentially cleaves these amino acids, such as Arg-C proteinase, Asp-N endopeptidase, Asp-N endopeptidase, chymotrypsin, clostripain, collagenase, elastase (type I or type II), formic acid, glutamyl endopeptidase, pepsin, proteinase K, staphylococcal peptidase I, thermolysin, and/or trypsin.

Here, reagents included elastase (Worthington Biochemical Corp., Lakewood, N.J.); phosphate buffered solution (PBS) with Ca$^{2+}$ and Mg$^{2+}$ (Hyclone, Logan, Utah); PBS without Ca$^{2+}$ and Mg$^{2+}$; and 100 mM EDTA solution: 1 ml of 0.5 M EDTA with 4 ml of PBS without Ca$^{2+}$ and Mg$^{2+}$.

Components for a Microfluidic Platform

Performing microfluidic sample preparation is now possible in traditional molecular biology laboratories with little prior engineering expertise. Commercially available ready-to-use microfluidic chips, fittings, valves, and pumps can be purchased and configured for microfluidic cell preparation and signal acquisition. The following materials are all commercially available, and customization can be achieved through the vendors.

Microfluidic chip: A custom fused silica microfluidic chip with fourteen ports, of which only thirteen ports are labeled in FIG. 3A. The design was made using AutoCAD (Autodesk Inc. San Rafael, Calif.), photomasks were generated at PhotoSciences (Torrence, Calif.), and fused silica chips were fabricated by Caliper Life Sciences (Hopkinton, Mass.). Other vendors may have become available for custom chip fabrications, but we have not compared quality of chips between different vendors. The vendor will typically aid in the formatting of the design file for custom chip fabrication. We recommend, in some situations, using fused silica or glass microfluidic chips. While other materials such as PDMS can also be used to fabricate chips, our method has been tested on glass chips.

The cell holding chamber had channel dimensions of a width of 200 µm, depth of 30 µm, and total length of about 12 cm. The dimensions of channels connected to sheath ports (sheath channels) included a width of 30 µm and a depth of 30 µm. An array of fourteen holes, each 500 µm in diameter, seven on each side of the device, provided fluid inlets/outlets to the cell holding chambers and the sheath channels. The center of the chip is shown magnified in FIG. 3A (right), where cells can be detached after flow-FISH and hydrodynamically focused for on-chip micro-flow cytometry. The fused silica chips can be reused after proper cleaning protocol between each experiment.

Pumping system, manifold, and controller components: The microfluidic platform also included a custom plastic chip manifold formed from an acetal resin (Delrin®); 1/32 inch o.d., 125 µm i.d. PEEK tubing (Upchurch Scientific, Oak Harbor, Wash.) for fluidic connections; fittings for PEEK tubing (Upchurch Scientific, Oak Harbor, Wash.) for fluidic connectors; fourteen custom built shut-off electronic valves, one for each port on the chip (commercial version available from LabSmith, Livermore, Calif.); an airtight pressurizable reagent reservoir; electronic pressure controllers (Parker Hannifin, Cleveland, Ohio); a house nitrogen source; a thermoelectric hot plate (TE Technology Inc., Traverse City, Mich.); and a proportional integral controller for hot plate.

Micro-flow cytometer components: The micro-flow cytometer included the following optical components to deliver an excitation source and measure resultant signals from the probes. The components includes a 20-mW diode pumped solid state laser at 488-nm (85-BCF-020-112; CVI Melles Griot, Carlsbad, Calif.) in an epifluorescence configuration for excitation; a long pass dichroic mirror (LPD01-4885; Semrock, Rochester, N.Y.); an aspheric lens (5722-H-B; New Focus, Santa Clara, Calif.); a photomultiplier tube (PMT)-based detector (H5784-20; Hamamatsu, Bridgewater, N.J.); a custom-made sculpted tip silica optical fiber (1000 µm core, 2000 µm sculpted spherical tip; Polymicro Technologies, Phoenix, Ariz.); an eight channel Hamamatsu linear multi-anode (LMA) PMT coupled with filter optics (H9797TM; Hamamatsu, Bridgewater, N.J.); three dichroic mirrors (DMT560, DMT650, and DMT740, Hamamatsu, Bridgewater, N.J.); and four bandpass filters (BPF534_30, BPF585_40, and BPF692_40, and BPF785_62, Semrock, Rochester, N.Y.).

Methods for Microfluidic Chip Setup, Cleaning, and Surface Modification for Reversible Cell Capture To prime the chip, sterile filtered deionized water was pre-loaded into each channel by placing a water droplet of ~100 µl onto an inlet port and allowing capillary forces to drive water into the microfluidic channel. Vacuum can be applied to an opposite port to facilitate water transport into the microchannel, thereby filling the microchannels with as much water as possible before assembly of the chip into the manifold.

FIG. 3A shows a device with various ports, and FIG. 3B shows a simplified schematic for microfluidic sample preparation station 3000. We employed custom-fabricated microvalves, reagent reservoirs, chip manifold, and computer control unit. Of course, commercial versions of the microvalves, reservoirs, and chip connectors can be purchased from, e.g., Fluigent SA (Paris, France) or LabSmith, Inc. (Livermore, Calif.). Some initial customization may be required, and the vendors should aid in the design and optimization of that initial customization. We have built a fourteen-valve setup with temperature control to accommodate the ten chamber microfluidic device 300 (shown in FIG. 3A, left). Each chamber 321-330 can hold up to 2000 cells and are fluidically isolatable to enable ten different experimental conditions in one chip experiment. An array of ports 310-320, 351, 360 serves as inlets and outlets for fluid connections to the chip's microchannels. The center of the device (FIG. 3A, right) provides the region in which cells can be hydrodynamically focused into single file for on-chip laser induced fluorescence and flow cytometry. The number of chip ports, valves, reservoirs, and pressure controllers can be customized for individual end user groups.

To set up the device (chip) 3010 (FIG. 3B), the custom manifold was visually aligned to the chip, and each port was connected to one end of the PEEK tubing via Upchurch fittings. The electronic shut-off valves 3061-3064 were used in-line with the tubing to control the movement of fluid into each port. The other end of the PEEK tubing was submerged in preloaded, airtight reservoirs M31-M34 and pressurized using house nitrogen and electronic pressure controllers 3031-3034. The pressure controllers 3031-3034 generate regulated pressure (arrows in inset of FIG. 3B) that is delivered into the reservoirs M31-M34.

By applying air into the sample reservoir M31 (FIG. 3B, inset), the positive pressure generated by the air drives fluid out through the longer tubing that is submerged in the preloaded reagent/sample and to the in-line valve 3061. In this manner, fluid can be moved, in a controllable manner, through tubing and reach programmable valves 3061-3064 that are connected in-line between the reservoirs M31-M34 and the microfluidic device 3010. The velocity at which the fluid flow into the chip is controlled by the pressure controllers 3031-3034. A greater pressure difference generates a faster fluid flow velocity and, therefore, higher shear stress inside the microfluidic channel.

The valves 3061-3064 and pressure controllers 3031-3034 can be controlled by a master controller (an integration hub 3040), which in turn is operated by way of a processor 3080. The user can control which port on the device the fluid can access by controlling the opening and closing of the in-line valves 3061-3064. For instance, an integration hub 3040 can connect the programmable valves and pressure controllers to a central computer 3080, where the user can script operational programs to automate sample preparation sequences, such as washing and staining of cells in the microfluidic device. A heat plate with temperature control can be added to facilitate incubation at higher temperatures.

Once assembled, the device can be prepared by filling with water. First, about 1 ml of water was introduced into the main port 310 (in FIG. 3A), which allows each chamber 321-330, flow cytometry channel 355, and sheath channel 356-357 to be filled with water, thereby reducing air bubbles within the channels. To load samples and/or reagents into the device, positive pressure from house nitrogen was used to transport the fluid from the reservoir and to the port, which in turn was in fluidic communication with the chambers and channels of the device. Pressure can be adjusted using the pressure controllers and, generally, pressures between 0.2 psi to 15 psi were used for the experiments described herein.

To address a specific cell chamber, various ports were opened and closed to provide a fluidic pathway (for the reagent) that led to the desired cell chamber. For instance, the main port 310 can be used to load reagents into the device, and valves can be controlled to provide the desired fluidic pathway. This can be achieved by opening the valve in fluidic communication to port 310, opening the valve to a port in fluidic communication with the targeted chamber, and providing the lowest pressure difference between the main port 310 and the targeted chamber, and then closing all other valves. Then, to introduce the reagent into the device, the pressure controller is used to apply house nitrogen to a pressurized reservoir connected to port 310, and the reagent in the reservoir will move from the reservoir into the target chamber. For example, to the target chamber 321, one can first shut off all valves, apply pressure to the main port 310, and open the valves to the main port 310 and the target port (i.e., the port 311, which when opened will provide the lowest pressure difference between the main port 310 and the target chamber 321), thereby ensuring that the preferential fluidic pathway will require transport of the reagent from the main port 310, through the target chamber 321, and exiting out of the target port 311.

The device can be cleaned for reuse. For instance, the device can be cleaned by flushing all channels with a 10% sterile filtered bleach in deionized water for 10 min. at 10 psi at RT, followed by a 10 min. flush with deionized water for 10 min.

For cell capture, the working Cell-Tak™ solution can be employed. First, 10 µl of 1 N NaOH was added to the working Cell-Tak™ solution within 10 min. of introducing the solution into the device. If the pH of the coating buffer is not between 6.5-8.0, Cell-Tak™ will not perform optimally. An aid to attaining this pH window is to use a volume of 1 N NaOH equal to half the volume Cell-Tak™ solution, used in combination with a neutral buffer. For example, one methodology includes 10 µl of Cell-Tak™, 285 µl of sodium bicarbonate (pH 8.0), and 5 µl of 1 N NaOH (added immediately before coating) to make 300 µl of the working Cell-Tak™ solution. About 1 ml of the working Cell-Tak™ solution is added into the reagent reservoir corresponding to the main port 310. All the valves are then opened to facilitate and flow of the working Cell-Tak™ solution from the main port 310 to all other ports at 15 psi for 5 min., and then pressure is reduced to 1.5 psi to maintain flow for 20 min.

Next, the reservoir tube with Cell-Tak™ solution was replaced with 1 ml of sterile filtered PBS. PBS was transported through all channels for 10 min. at 10 psi to flush out residual Cell-Tak™ solution. Flow was stepped, and the coated device should be used within one day.

Methods for Constructing the Micro-Flow Cytometer

While setting up the device and fluid control station can be done with minimal engineering knowledge, building a custom micro-flow cytometer requires high technical expertise in mechanical and optical engineering. If no such engineering capabilities are available, samples can be detached from the chip and analyzed using a commercial flow cytometer. If using conventional flow cytometer for analysis, this following construction method can be omitted.

A simplified schematic of the micro-flow cytometer 3100 is shown in FIG. 3C. The optical fiber 3111 and PMTs 3171-3174 are aligned vertically to the area on the device 3110 where cells are hydrodynamically focused into a single file line. As the cells pass through the laser beam, the PMTs record scatter and laser induced fluorescence signals coming off of the cells.

To build the micro-flow cytometer, we employed a 20-mW diode pumped solid state laser at 488-nm 3160 in an epi-fluorescence configuration for excitation. The laser 3160 was placed beneath the device 3110, and the laser beam was aligned to reflect and focus upon the detection region at the center of the device 3110 by using a long pass dichroic mirror and an aspheric lens. An optical fiber 3111 with a PMT 3120 was installed and aligned on top of the device 3110, where the alignment position should be slightly behind the path of the laser beam to collect forward scatter from passing cells.

Beneath the device 3110, an optical system was installed to provide an excitation source, as well as to configure the detector. First, an aspheric lens 3130, dichroic mirror, and PMT modules 3171-3174 were installed beneath the device 3110 so that scatter and fluorescence signals from passing cells will first be focused by the lens 3130 and subsequently passed via the dichroic mirror for detection in the PMT module.

For multiplexed fluorescence detection, we employed an eight channel Hamamatsu linear multi-anode (LMA) PMT coupled with filter optics. For a four color detection setup, we used four channels of the LMA PMT and selected the filtering for green, yellow, red, and far-red fluorescence detection. Bandpass filters 3175 were used for selected wavelengths.

For green fluorescence detection, we cascaded a portion of the aggregate florescence signal upon the first LMA PMT channel via a longpass dichroic mirror and filtered through to the detection region of that channel using a bandpass filter (BPF534_30). For yellow fluorescence detection, we cascaded a portion of the remaining florescence signal upon the second LMA PMT channel using another longpass dichroic mirror (DMT650) and filtered through to the respective channel's detection region using a second bandpass filter (BPF585_40). For red fluorescence detection, we used the third channel of the LMA PMT via a third longpass dichroic (DMT740) and filtered using a third bandpass filter (BPF692_40). For far-red fluorescence detection, we cascaded the remaining florescence signal onto the fourth LMA PMT channel using a mirror, and filtered onto that channels detection region using a fourth bandpass filter (BPF785_62).

Methods for miR155 Detection in PMA and Ionomycin Activated Jurkat Cells

Jurkat cells (ATCC, Manassas, Va.) were cultured in RPMI supplemented by 10% FBS (Hyclone, Logan, Utah) in a humidified cell culture incubator, which was maintained at 5% $CO_2$ and 37° C. Then, cells were seeded at $10^6$/ml at 1 ml per well into a 24 well plate. Stimulation experiments were conducted by incubating Jurkat cells for 0, 8, 16, 20, or 24 hours with 10 ng/ml PMA and 1 µM ionomycin. About 2 µl of 500×PMA and ionomycin working solution was added to each well and then swirled to mix. Incubation for designated lengths of time was conducted in the cell culture incubator.

At designated times, Jurkat cells were transferred to Eppendorf tubes, centrifuged at 300 g for 5 min., and resuspended with 1 ml of 8% PFA solution for each tube, and incubated at RT for 10 min. Fixed cells were pelleted at 300 g for 5 min., resuspended with 1 ml of PBS for each tube, and incubated at RT for 5 min. This last step was then repeated. Then, the washed cells were pelleted at 300 g for 5 min. and resuspended in 50 µl of PBS to make $2\times10^7$ cells/ml for loading onto the chip.

Jurkat cells were loaded into reservoirs and transported within a Cell-Tak™ surface modified device at 5 psi for 3 min. The following ports were used to provide the desired fluidic pathway that resulted in capture of cells in the desired cell chamber: for 0 h. cells—from port 311 to exit port 360, port 320 (to fill chambers 321, 330); for 8 h. cells—from port 312 to exit port 360, port 319 (to fill chambers 322, 329); for 16 h. cells—from port 313 to exit port 360, port 318 (to fill chambers 323, 328); for 20 h. cells—from port 314 to exit port 360, port 317 (to fill chambers 324, 327); and for 24 h. cells—from port 315 to exit port 360, port 316 (to fill chambers 325, 326). After targeting the desired cell chambers, flow was stopped, and the cells were incubated for 15 min. at RT to allow capture onto the surface of the microchannels.

Methods of CD69 Cell Surface Protein Immunostaining

On-chip cell surface protein immunostaining was performed as follows. Immediately after cell loading, a 1:50 dilution of anti-CD69-biotin antibody (1 µl antibody with 49 µl of TBS) was prepared. Then, the antibody solution (a protein label) was transported through the main port 310 and into each chamber at 5 psi. After 2 min., flow was stopped. The antibody solution was incubated for 30 min. at RT. Next, a TBST buffer was transported through the channels at 2 psi for 5 min. The probe having a detectable marker (Qdot® 705-labeled streptavidin) was diluted at 1:50 in TBS (1 µl Qdot®-705 streptavidin in 49 µl TBS). This solution was then transported to the channels at 5 psi for 2 min., flow was then stopped, and the device was incubated at RT for 30 min. Finally, the probe was rinsed through the device by flow of TBST through the channels at 2 psi for 5 min.

Methods for In Situ Hybridization with miR155 and Scrambled LNA Probes

On-chip cell miRNA detection was performed as follows. Captured, immunostained cells were permeabilized by flowing 0.25% Triton™ X-100 in TBS to each chamber. Flow was stopped, and the device was incubated for 10 min. at RT. Cells were washed with TBS for 10 min. at 3 psi. and then with Solution 1 (described herein) for 5 min. at 5 psi. Cells were then incubated with Solution 2 (described herein) for 30 min. at RT, and then washed with TBS for 5 min. at 5 psi. Pre-warmed hybridization solution (to 65° C.) was transported into all chambers for 5 min. at 5 psi, followed by incubation for 1 h. at 62° C. for pre-hybridization to decrease non-specific hybridization.

During the 1 h. pre-hybridization phase, 2 µM LNA probe solutions in hybridization buffer (5 µl of 10 µM LNA stock with 20 µl of hybridization buffer) were prepared. After the 1 h. pre-hybridization phase, the prepared LNA probe solutions were transported into chambers for 3 min. at 5 psi.

The following ports were used to provide the desired fluidic pathway that resulted in labeling with the miR155 probe in the desired cell chamber: from port 311 to port 312 (to fill chambers 321, 322), port 313 (to fill chamber 323), port 314 (to fill chamber 324), port 315 (to fill chamber 325), and exit port 360 (to prevent overflow into chambers 326-330). The following ports were used to provide the desired fluidic pathway that resulted in labeling with the scrambled probe in the desired cell chamber: from port 320 to port 319 (to fill chambers 330, 329), port 318 (to fill chamber 328), port 317 (to fill chamber 327), port 316 (to fill chamber 326), and exit port 360 (to prevent overflow into chambers 321-325). After establishing the desired fluidic pathway, flow was stopped to allow for hybridization at 80° C. for 90 s., followed by incubation at 62° C. for 90 min. Then, the chambers were washed with 2×SSC with 50% formamide at 65° C. for 10 min., where flow was established for 5 min. at 5 psi and then stopped to allow for incubation for 5 min.). Successive washes included washing with 1×SSC for 20 min. at RT (flow for 5 min. at 5 psi, stop flow, and incubate for 5 min.) and with 0.1×SSC for 20 min. at RT (flow for 5 min. at 5 psi, stop flow, and incubate for 5 min.).

Methods for miR155 Signal Amplification Using Proximity Ligation and Rolling Circle Amplification All reagents for RCA amplification, with the exception of the anti-DIG antibody, were part of the Duolink® mouse PLUS kit, mouse MINUS kit, and green detection kit from Olink AB (Uppsala, Sweden). The kits included a Duolink® Blocking solution (1×) (including 5-chloro-2-methyl-4-isothiazolin-3-one/2-methyl-4-isothiazolin-3-one (3:1 mixture) and bovine serum albumin); a Duolink® Diluent solution (1×) (including 5-chloro-2-methyl-4-isothiazolin-3-one/2-methyl-4-isothiazolin-3-one (3:1 mixture) and bovine serum albumin); Duolink® PLA probe anti-mouse MINUS/PLUS (including the probe, 5-chloro-2-methyl-4-isothiazolin-3-one/2-methyl-4-isothiazolin-3-one (3:1 mixture), and bovine serum albumin); Duolink® Ligase (1 U/µl) (including dithiothreitol (DTT)); Duolink® Ligation solution (5×) (including tris hydrochloride, tris(hydroxymethyl)aminomethane, and DTT, as well as all components needed for ligation (e.g., oligonucleotides that hybridize to the PLA probes, such as connector probes) except the ligase); Duolink® Polymerase (10 U/µl) (including DTT); Duolink® Amplification solution (5×) (including tris(hydroxymethyl)aminomethane, as well as all components needed for RCA (e.g., oligonucleotide probes labeled with a fluorophore that hybridize to the RCA product) except the polymerase).

Enzymes were transported on ice during the experiment to prevent degradation. When the anti-DIG antibody was first used, the antibody solution was divided into working 5 µl aliquots and stored at −20° C. to avoid repeated freeze/thaw cycles. All unconjugated antibodies should be stored as working aliquots at −20° C.

The RCA assay was performed on-chip as follows. First, the Duolink® Blocking solution was transported to each chamber in the device for 5 min. at 5 psi. Flow was then stopped to allow incubation for 30 min. at 37° C. Then, the anti-DIG antibody solution (diluted at 1:50 with 1 µl of anti-DIG antibody and 49 µl of PBS) was transported into all chambers and incubated for 30 min. at RT. The chambers were then washed with TBST for 5 min. at 5 psi at RT. Next, Duolink® PLA probe anti-mouse MINUS and Duolink® PLA probe anti-mouse PLUS agents (diluted at 1:5 with 10 µl of PLUS, 10 µl of MINUS, and 30 µl of Duolink® Diluent solution), were transported into all chambers for 3 min. at 5 psi. Flow was stopped to allow incubation for 30 min. at 37° C. Again, chambers were then washed with TBST for 5 min. at 5 psi at 37° C.

Ligase and polymerase reactions were then conducted to form the circular template and to form the concatemer based on this template. First, a ligase solution (diluted at 1:40 with 8 µl of Duolink® Ligation solution (5×), 31 µl of water, and 1 µl of Duolink® Ligase (1 U/µl)) was transported to all chambers at 5 psi for 3 min. Flow was stopped to allow incubation for 30 min. at 37° C. Then, chambers were washed with TBST for 5 min. at 5 psi at 37° C. Next, a polymerase solution (diluted to 1:80 with 8 µl of Duolink® Amplification solution (5×), 32 µl water, and 0.5 µl of Duolink® Polymerase (10 U/µl)) was transported to all chambers for 3 min. at 5 psi. Flow was stopped to allow incubation for 2 h. at 37° C. Cells were then fixed by transporting 1% PFA in TBS to each chamber for 5 min. at 5 psi at RT. Finally, all chambers were washed with TBS for 5 min. at 5 psi at RT.

At this point, cells were ready for imaging. The amplified miR155 signal appeared as fluorescent green dots in the cytosol, and the Qdot®-labeled CD69 protein was visualized in the same cell. See FIG. 6A as an example of a multiplexed miRNA and protein detection in the same cell. There should be visible incremental increase in miR155 signal, as well as CD69 signal as time of stimulation with PMA and ionomycin increases.

Methods for Cell Detachment

After on-chip sample preparation and image acquisition, cells can be detached from the Cell-Tak™ modified channel surface by a combination of proteolytic cleavage and shear force. First, a 100 µg/ml elastase solution was prepared in PBS containing $Ca^{2+}$ and $Mg^{2+}$. Then, this elastase solution was transported into each chamber and incubated for 5 min. at 42° C., followed by flowing elastase solution for 5 min. at 15 psi into collection tubes containing 100 µl of 100 mM EDTA in $Ca^{2+}/Mg^{2+}$ free PBS (20 µl of 0.5 M EDTA and 80 µl of PBS).

For each cell holding chamber, detached cells were transported towards exit port 360. At the same time, PBS was transported from sheath port 351 to exit port 360 to act as sheath fluid to hydrodynamically focus the detached cells from the holding chambers for on-chip flow cytometry. Samples can be analyzed by using the micro-flow cytometer, as described herein, or a commercial flow cytometer, as also described herein.

Methods for Cell Analysis Using Micro-Flow Cytometer

The micro-flow cytometry was performed at the center of the chip (FIG. 3A, right), where the sheath fluid focuses the sample stream containing the detached cells into the path of the laser beam coming from underneath the chip. To hydrodynamically focus the sample portion, the cells were first detached by transporting the elastase solution from a port corresponding to the desired chamber to the exit port 360 at 15 psi. For instance, to analyze a sample portion from chamber 321, the elastase solution can be transported from port 311 to exit port 360.

Then, sheath fluids were transported to the flow cytometry channel by flowing a sheath fluid (e.g., PBS) from sheath port 351 to exit port 360 at 5 psi to hydrodynamically focus the cells. The pressure at the sheath port 351 can be adjusted between each sample to ensure that focusing is consistent across all chambers. The pressure settings for creating consistent hydrodynamic focusing between chambers can be determined empirically by using 10% glycerol solution in PBS in the sheath channel. For instance, the glycerol solution can be transported into sheath port 351 and then towards exit port 360 at 5 psi. Then, PBS can be transported through each assay chamber one at a time and towards exit port 360 at 15 psi. Flow characteristics can be determined visually to assess much pressure to apply at sheath port 351 so that the pinched PBS stream remains in the center of the channel and at a consistent width.

Detectable signals can be collected using the optical system, as shown in FIGS. 2D and 3C. For instance, laser-induced forward scatter and fluorescence signals can be collected from the passing cells with the optical fiber and PMT located above the device. Multiple spectra can be detected by collecting the scatter and fluorescence signals for all channels (488-nm scatter, green, yellow, red and far-red) by the data acquisition module located beneath the device. Histograms of scatter and fluorescence data were generated with each cell passing through the detection region (dashed circle in FIG. 3A, right), and peaks from each histogram were identified (e.g., using LabVIEW to script a "peak finder" application) from the scatter and fluorescence histograms to generate a numerical value representing each cell. Peak values were then exported (e.g., into either Excel or Kaleidagraph) and plotted in each sample set to generate histograms for each experimental conditions. Generated histograms were overlaid to show changes in the fluorescence between each experimental condition.

Methods for Flow Cytometric Analysis Using Commercial Flow Cytometer

Instead of an on-chip micro-flow cytometer, analysis can be conducted off-chip by using a commercial flow cytometer. This method includes pre-labeling new collection tubes with sample identification information and aliquoting 100 μl of 100 mM EDTA solution into each collection tube. The tubes should be stored on ice for at least 10 min. prior to cell detachment. On-chip cells can be detached (e.g., as described herein) and collected from each chamber in its own collection tube. Detached cells should be immediately stored on ice. Within each collection tube, the total volume can be brought up to 200 μl with an ice cold 100 mM EDTA solution and then immediately analyze in commercial flow cytometer.

Example 4: Microfluidic Molecular Assay Platform for the Detection of miRNAs, mRNAs, Proteins, and Post-Translational Modifications at Single-Cell Resolution Since we know that cells in populations behave heterogeneously (see, e.g., Wu M et al., *Curr. Opin. Biotechnol.* 2012 February; 23(1):83-8), especially in the cases of stem cells, cancer, and hematopoiesis, there is need for a new technology that provides capability to detect and quantify multiple categories of signaling molecules in intact single cells to provide a comprehensive view of the cell's physiological state. In this example, we describe an exemplary, automated microfluidic platform with a portfolio of customized molecular assays that can detect nucleic acids, proteins, and post-translational modifications in single intact cells with >95% reduction in reagent requirement in under 8 hours.

Figure 7:
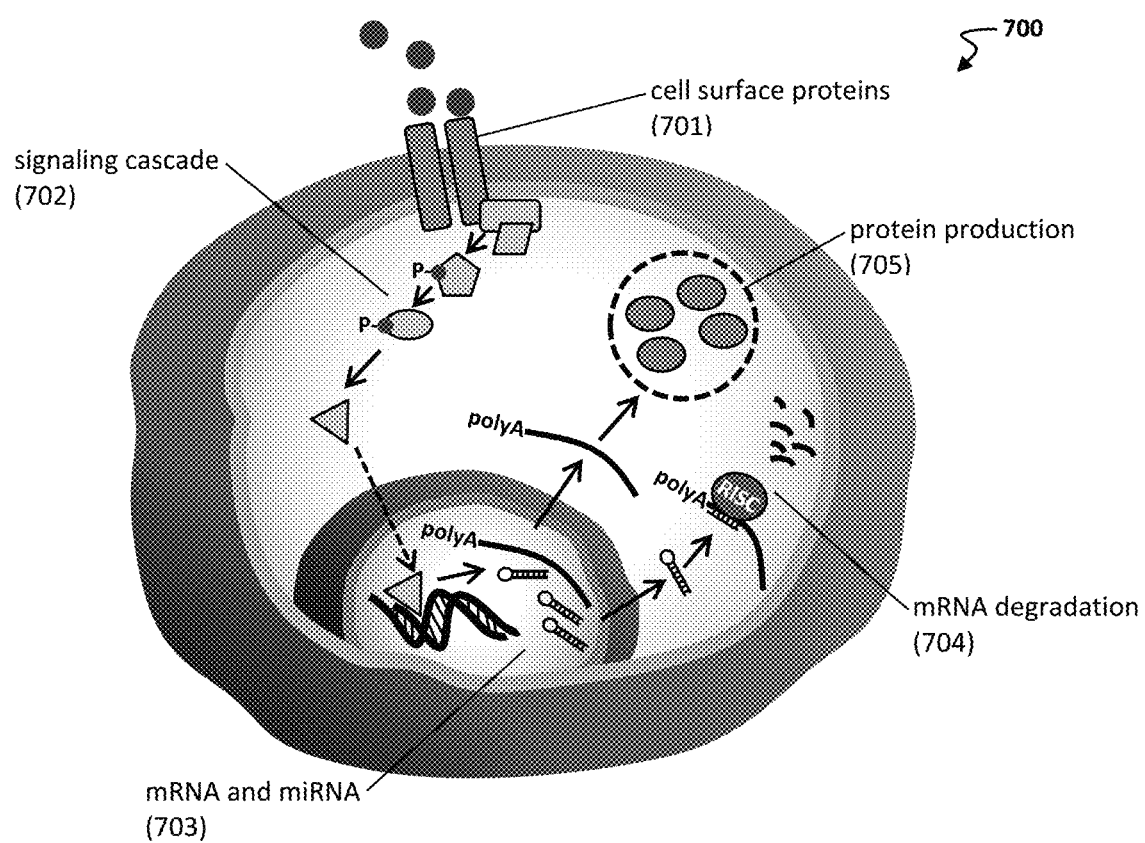
FIG. 7 is a schematic of a cell 700 showing various cellular processes and exemplary targets suitable for multiplexed detection using the methods, devices, and platforms described herein. In one exemplary process, activation of a cell surface receptor 701 leads to a phosphorylation signaling cascade 702, which then induces the transcription of messenger RNAs (mRNAs) and microRNAs (miRNAs) 703. The mRNA and miRNA are exported into the cytosol, and mRNA is translated into proteins 705. The miRNA can inhibit protein translation by binding mRNA and inducing their degradation 704.

Cell signaling is a dynamic and complex, intricate process that involves many players, including proteins, nucleic acids, and transient post-translational modifications (PTMs) (FIG. 7). The traditional view of the cell signaling cascade begins with cell surface receptor activation 701 of the cell 700, where a change in receptor structure conformation begins a cascade of events 702 (e.g., a kinase cascade, where kinases transiently phosphorylate in series), leading to the translocation of transcription factor into the nucleus to induce expression of relevant genes into messenger RNA (mRNA) 703. The induced mRNA is exported into the cytosol and translated into proteins 705 that can then carry out response to the original stimulus that activated the surface receptor.

To make the process even more complex, miRNAs can be induced along with the mRNA 703, and the miRNAs function by binding the 3' untranslated region (UTR) and recruit the RISC complex to degrade the mRNA 704 (Krutzfeldt J et al., *Cell. Metab.* 2006; 4:9-12). In this manner, miRNA can modulate mRNA expression in the cytosol.

Signaling pathways involve proteins, miRNA, and mRNAs, along with various forms of transient post-translational modifications, and detecting each type of signaling molecule requires categorically different sample preparation methods such as Western blotting for proteins, PCR for nucleic acids, and flow cytometry for post-translational modifications. For instance, analysis of each class of biomolecules currently requires categorically different methods for sample preparation and detection. Proteins are primarily detected by Western blotting, nucleic acids by PCR, and PTMs by flow cytometry or mass spectrometry. The multiple sample preparation techniques required to detect different categories of molecular targets involve labor-intensive steps, including stimulation, fixation, permeabilization, immunostaining, and multiple wash steps in between. The manual methods for performing large-scale cell signaling studies not only involve bulky equipment but also many opportunities for user-introduced artifacts that can confound reproducibility.

The analysis of cellular signaling is further complicated by the fact that cells are heterogeneous in nature. To fully understand how individual cells respond to stimuli in cellular and disease processes, one must study the changes in protein, mRNA, miRNA, and PTMs at the single-cell level. For example, to study the CD8 T-cell response to different vaccines requires distinguishing T-cell subtypes based on cell surface markers to study the heterogeneous gene expression patterns in individual T cells that underlie differential induction of vaccine-induced immunity (Flatz L et al., "Single-cell gene-expression profiling reveals qualitatively distinct CD8 T cells elicited by different gene-based vaccines," *Proc. Nat'l Acad. Sci. USA* 2011 Apr. 5; 108(14): 5724-9). Bulk profiling methods only generate averaged signaling measurement from heterogeneous cell populations, and single-cell resolution analysis of miRNA, mRNA, and protein will yield information otherwise unattainable using bulk methods. Existing single-cell analysis methods include amplification-based methods that include PCR-based amplification to profile DNA and RNA, but these methods can introduce bias during the amplification and require days of hands-on manipulation time to accomplish. In addition, amplification-based single-cell analysis methods require lysis and nucleic acid extraction and cannot be used practically to profile proteins and PTMs along with the nucleic acids in the same cell.

Understanding the role of all these key biomolecular players in signaling networks on a single-cell level is critical for deciphering the molecular mechanisms of cellular and disease processes. Such a study requires an integrated, multiplexed platform that enables a systems-level investigation of the complex interactions between these signaling biomolecules. To date, no technology exists that can integrate the detection and analysis of all the signaling molecules, particularly at the single-cell level.

To address the need for a new technology that provides true single-cell resolution multiplexed signaling analysis, we have developed an automated, microfluidic platform (FIG. 2A-2D) with accompanying molecular assays that enable rapid processing of intact cells (~8 h) to simultaneously detect miRNAs, mRNAs, proteins, and PTMs at single-cell resolution, with only ~270 nL reagent and ~1000 cells required per chamber.

The molecular assays that accompany the platform combine in situ hybridization (ISH) and immunostaining to gain access to both nucleic acid and protein targets without the need to lyse and amplify cellular signals. An added benefit is that both ISH and immunostaining are compatible with microscopy for visual inspection of the spatiotemporal correlation between the proteins and nucleic acid species, while the same sample can be analyzed in a flow cytometer to gather quantitative data regarding the magnitude of the cellular signals.

The entire multiplexed single-cell detection platform is designed with graphic user interface-based software (FIG. 2C) that controls all valves and pumps, allowing for hands-free operation of the platform from cell loading and stimulation to sample preparation, followed by detection and automated analysis (FIG. 2D). The elimination of manual cell handling steps greatly reduces time and labor, and the microfluidic format reduces sample and reagent requirement by ~95%, with the added benefit of eliminating user error. The automated platform provides systems-level high-content profiling of mRNA, miRNA, and proteins in an integrated experimental space.

In this example, we highlight the molecular assays developed on the microfluidic platform that allow for the automated detection of miRNA, mRNA, and proteins, as well as the work flow that allows multiplexed detection of different categories of biomolecules in the same cell.

Materials and Methods

Materials and methods were similar to Examples 1-3, unless otherwise indicated.

Cell culture and stimulation: The RAW 264.7 murine macrophage cell line was purchased from ATCC (Manassas, Va.), cultured in growth medium consisting of 450 ml of Dulbecco's modified Eagle's medium (DMEM), 50 ml of fetal bovine serum (FBS) (100-500, Gemini, West Sacramento, Calif.), 10 ml of HEPES, 5 ml of L-glutamine (200 mM), 1:100 penicillin/streptomycin (Gibco, Carlsbad, Calif.), and 200 µg/ml Geneticin (InvivoGen, San Diego, Calif.). RAW cells were captured in the microfluidic device and stimulated with 100 nM *Escherichia coli* smooth lipopolysaccharide (LPS) (L4524; Sigma-Aldrich, St. Louis, Mo.) in growth media for various times.

Microfluidic assays for cell surface protein expression, cytosolic phosphoproteins, and cytokine staining: For protein immunostaining, cells were cultured for up to 4 h. with 1 µL/ml Golgi-Plug reagent containing brafeldin A (555029; BD Biosciences) and fixed with paraformaldehyde (1.5%-8%) for 10 min.; incubated with fluorescent-labeled antibody targeting cell surface receptors, TLR4/MD2 receptor at 1:15 dilution (117605; BioLegend, San Diego, Calif.) or CD69 early T-cell activation marker at 1:100 dilution (13-0699-80; eBioscience, San Diego, Calif.) for 15 min; and washed for 5 min. with PBS. Following cell surface staining, cells were permeabilized with 0.1% Triton™ X-100 and incubated with intracellular phospho-specific ERK1/2 at a 1:15 dilution (4375; Cell Signaling Technology, Danvers, Mass.) and intracellular tumor necrosis factor-α (TNF-α) at a 1:50 dilution (19-732181; eBiosciences) for 30 min.

Microfluidic mRNA and miRNA ISH: Double DIG-labeled locked nucleic acid (LNA) probes for miRNA 155, scrambled miRNA control, and an N-terminal biotin-labeled β-actin mRNA LNA probe were purchased from (Exiqon, Vedbaek, Denmark). The following LNA-containing probes were used for miRNA and mRNA detection:

```
miR155:
                                    (SEQ ID NO: 1)
/5DigN/ACCCCTATCACGATTAGCATTAA/3Dig_N/;

Scrambled:
                                    (SEQ ID NO: 2)
/5DigN/GTGTAACACGTCTATACGCCCA/3Dig_N/;

β-actin (hsa):
                                    (SEQ ID NO: 3)
biotin-5'-CTCATTGTAGAAGGTGTGGTGCCA-3';
and Scrambled:
                                    (SEQ ID NO: 4)
biotin-5'-GTGTAACACGTCTATACGCCCA-3'.
```

After performing protein immunostaining as described in the previous section, the miRNA and mRNA ISH was performed on the same cells. The amplification method was performed as described previously (Wu M et al., *PLoS One* 2013; 8(1):e55044). Briefly, the following ISH reagents were made fresh: Solution 1 (0.13 M 1-methylimidazole, 300 mM NaCl, pH 8.0, adjusted with HCl); 1-ethyl-3-(3-dimethylaminopropyl)carbodiimide (EDC) solution (Solution 2, i.e., 0.16 M EDC in Solution 1, adjusted to pH 8.0); and hybridization buffer (50% formamide, 2× saline-sodium citrate (SSC) buffer, 50 µg/ml yeast transfer RNA (tRNA), 50 µg/ml salmon sperm, and 50 mM NaPi). The immunostained cells were washed with Solution 1 for 5 min, followed by incubation with Solution 2 for 20 min., and then washed for 5 min. with Tris-buffered saline (TBS). The cells were then pre-hybridized for 30 min. at 62° C. in hybridization buffer pre-warmed to 65° C.

All LNA probes were used with the 10-pmol/25-µL hybridization buffer and flown into pre-determined chambers. Hybridization with LNA probes was performed for 90 s. at 80° C., followed by 90 min. at 62° C., which was then followed by the following washes: 2×SSC+50% formamide for 10 min. at 65° C., 1×SSC for 20 min. at RT, and finally 0.1×SSC for 5 min. at RT.

For the β-actin mRNA, the hybridized biotinylated LNA probe can be detected by incubation with PE-conjugated streptavidin at 1:200 (S-866; Life Technologies, Carlsbad, Calif.) for 30 min., followed by a 5 min. TBS wash. For miRNA signal, proceed to rolling circle amplification.

Microscopy: Brightfield, epifluorescence, and phase contrast images were captured at ×60 and ×100 magnification on an Olympus (Tokyo, Japan) IX-71 inverted microscope equipped with a CoolSNAP HQ CCD camera (Photometrics, Tucson, Ariz.) and Image-Pro software (Media Cybernetics, Bethesda, Md.).

Figure 8A:
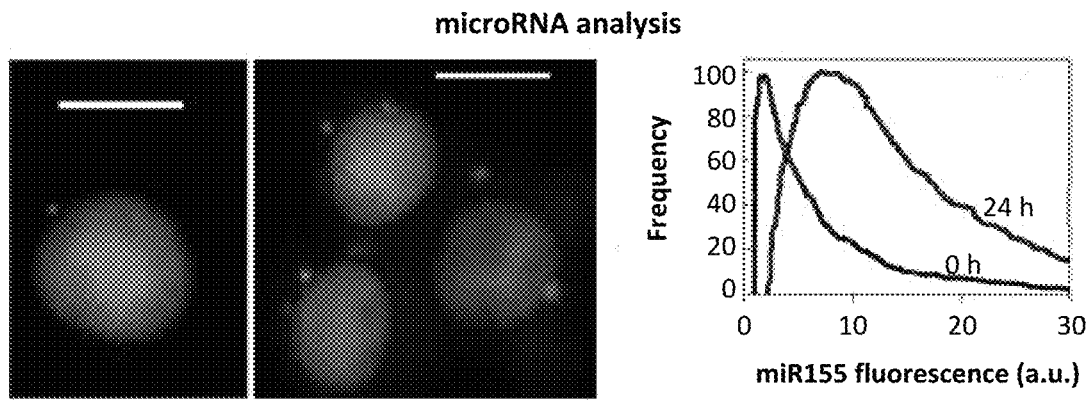
FIG. 8A-8F provides a portfolio of microfluidic assays developed for the platform herein. Shown are (A) microRNA (miRNA) analysis; (B) messenger RNA (mRNA) analysis; (C) cell surface protein analysis; (D) protein phosphorylation profiles; (E) cytosolic protein expression profiles; and (F) dynamic glycosylation profiles that were performed on-chip. Provided are data of (A) miRNA 155 in Jurkat cells after 24 h. stimulation with PMA and ionomycin; (B) β-actin mRNA in Jurkat cells compared with a scrambled control probe; (C) RAW 264.7 cell surface receptor activation as demonstrated by TLR4-MD2 receptor activation by lipopolysaccharide (LPS) at 30 s. and 30 min.; (D) transient P38 protein phosphorylation in RAW 264.7 upon 30 min. stimulation with LPS; (E) cytosolic tumor necrosis factor-α (TNF-α) cytokine production in LPS-stimulated RAW 264.7 cells; and (F) dynamic glycosylation of nucleoporin 62 (Nup62) after stimulation.
Figure 8B:
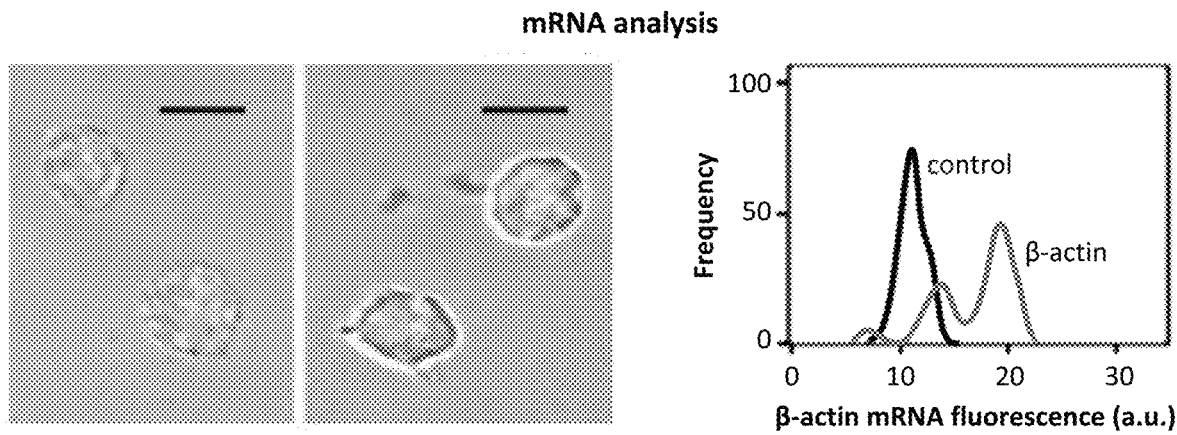

Results and Discussion miRNA detection: The most technically challenging molecular target to detect in an intact single cell is miRNA (FIG. 8A). To detect miR-NAs at single-cell resolution, a novel flow cytometry compatible fluorescent in situ hybridization (flow-FISH) assay to detect miRNAs using LNA-containing probes has been developed in our laboratory (Wu M et al., *PLoS One* 2013; 8(1):e55044). The LNA flow- FISH assay combines the advantage of LNA's high melting temperature (Silahtaroglu A N et al., *Mol. Cell. Probes* 2003; 17(4):165-9) with the specificity of proximal ligation and rolling circle amplification (Söderberg O et al., "Direct observation of individual endogenous protein complexes in situ by proximity ligation," *Nat. Methods* 2006 December; 3(12):995-1000) to provide highly specific amplification of otherwise undetectable miRNA signals in an intact cell, which then can be visualized via microscopy and quantified using flow cytometry. The detection of miRNA species by LNA-flow FISH can be multiplexed with mRNA detection, and the isothermal nature of rolling circle amplification makes multiplexing with protein immunostaining possible.

mRNA detection: The LNA flow-FISH method can easily be used to detect mRNA (FIG. 8B), where β-actin mRNA was detected using biotinylated LNA-containing probes. For abundant mRNA targets, no further enzymatic signal amplification is required. The mRNA-probe complex can be detected by incubating with fluorescent-labeled streptavidin. The binding partner-based (e.g., biotin-streptavidin-based) mRNA detection can be multiplexed with miRNA detection.

Figure 8C:
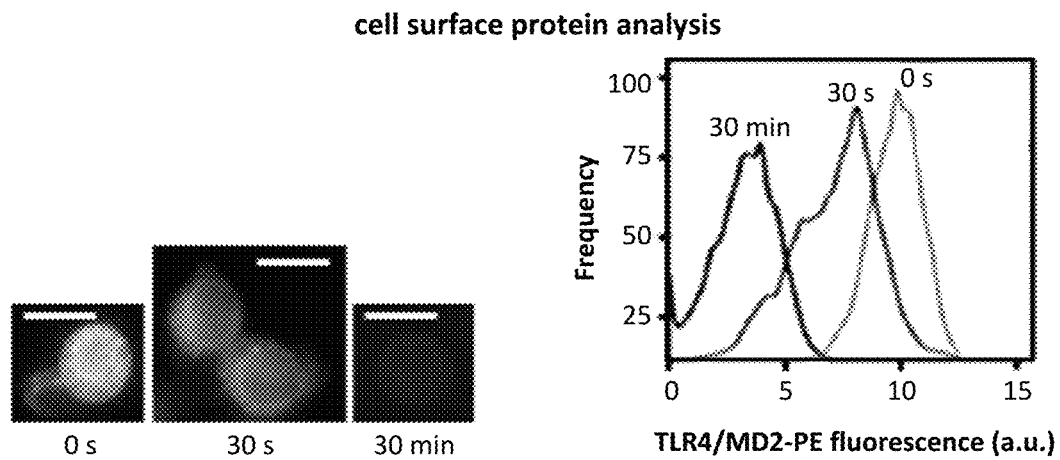

Cell surface protein detection: To demonstrate the detection of cell surface proteins, we used fluorescent dye-labeled antibodies directed against cell surface proteins after initial paraformaldehyde fixation of the cells but prior to permeabilization with Triton™ X-100. In FIG. 8C, the cell surface receptor complex TLR4/MD2 was activated by LPS. As the TLR4/MD2 complex changed conformation as a result of TLR4 activation, the complex lost affinity to the antibody directed against the inactive TLR4/MD2 complex. As a result, the fluorescence associated with the inactive TLR4/MD2 complex decreased as a function of time after addition of LPS.

Figure 8D:
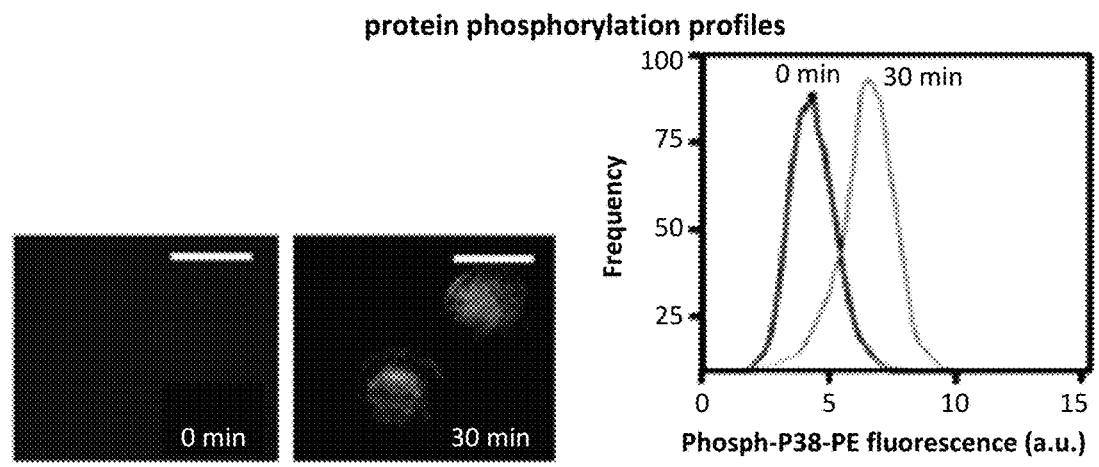

Protein phosphorylation profiles: FIG. 8D illustrates the detection of transient phosphorylation in signaling proteins by demonstrating the detection of phosphorylated p38 protein after LPS stimulation of macrophages. p38 is a known component of the TLR4 innate immune pathway, and the phosphorylation of p38 has been shown to lead to induction of proinflammatory genes (Bode J G et al., "The macrophage response towards LPS and its control through the p38(MAPK)-STAT3 axis," *Cell. Signal.* 2012 June; 24(6): 1185-94). By using phospho-specific antibodies conjugated to fluorescent dyes, any phospho-profiling of kinase cascades can be performed using the platform (see, e.g., Srivastava N et al., *Anal. Chem.* 2009 May 1; 81(9):3261-9).

Figure 8E:
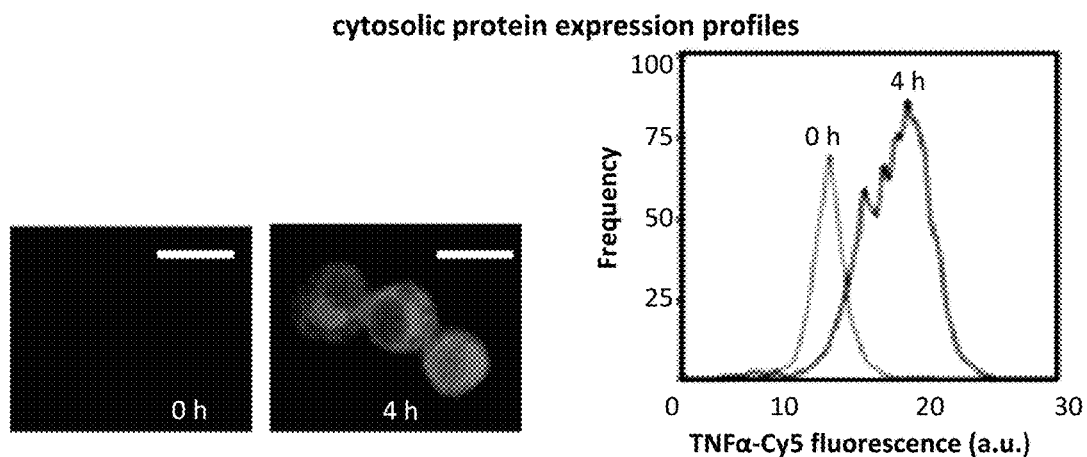

Cytosolic protein expression profiles: Intracellular proteins can be detected using fluorescent conjugated antibodies. To detect proteins that are released from the cell, such as chemokines and cytokines, a Golgi release inhibitor such as brefeldin A can be added to the culture media for up to 8 h. to increase the intracellular concentration of cytokines for detection by immunostaining. In FIG. 8E, LPS-activated macrophages were treated with brefeldin A for 4 h., and the intracellular TNF-α protein was detected using the anti-TNF-α antibody.

Figure 8F:
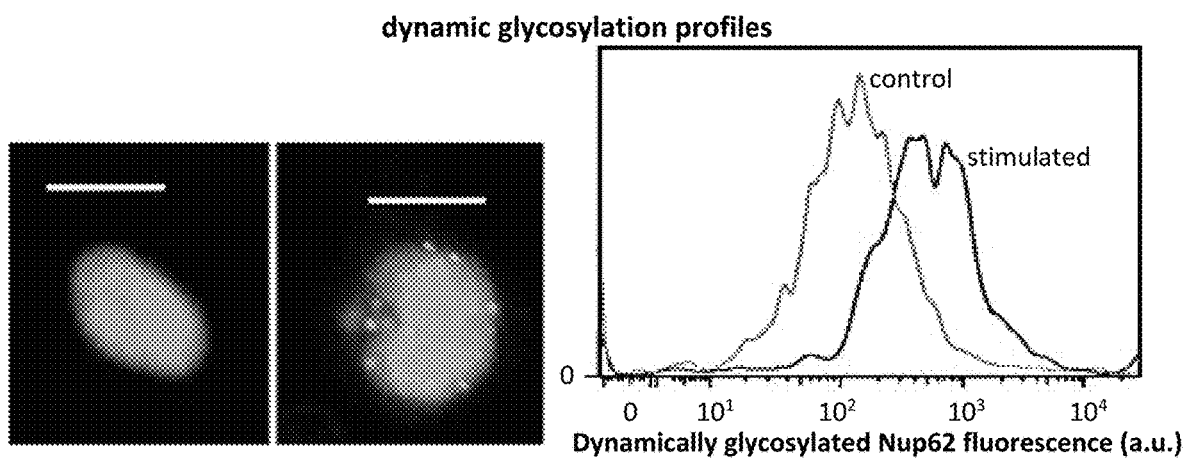

Dynamic glycosylation profiles: Post-translational modifications, such as glycosylation, provide an important biomolecular mechanism to induce various cellular responses. For instance, nucleoporin 62 (Nup62) is a nuclear pore protein complex that mediates RNA and protein transport through the nuclear envelope. Both glycosylation and phosphorylation of Nup62 influences the conformation of this complex and could mediate pore assembly and disassembly. Transient and/or dynamic glycosylation profiles can be detected on-chip, as seen in FIG. 8F.

Figure 12:
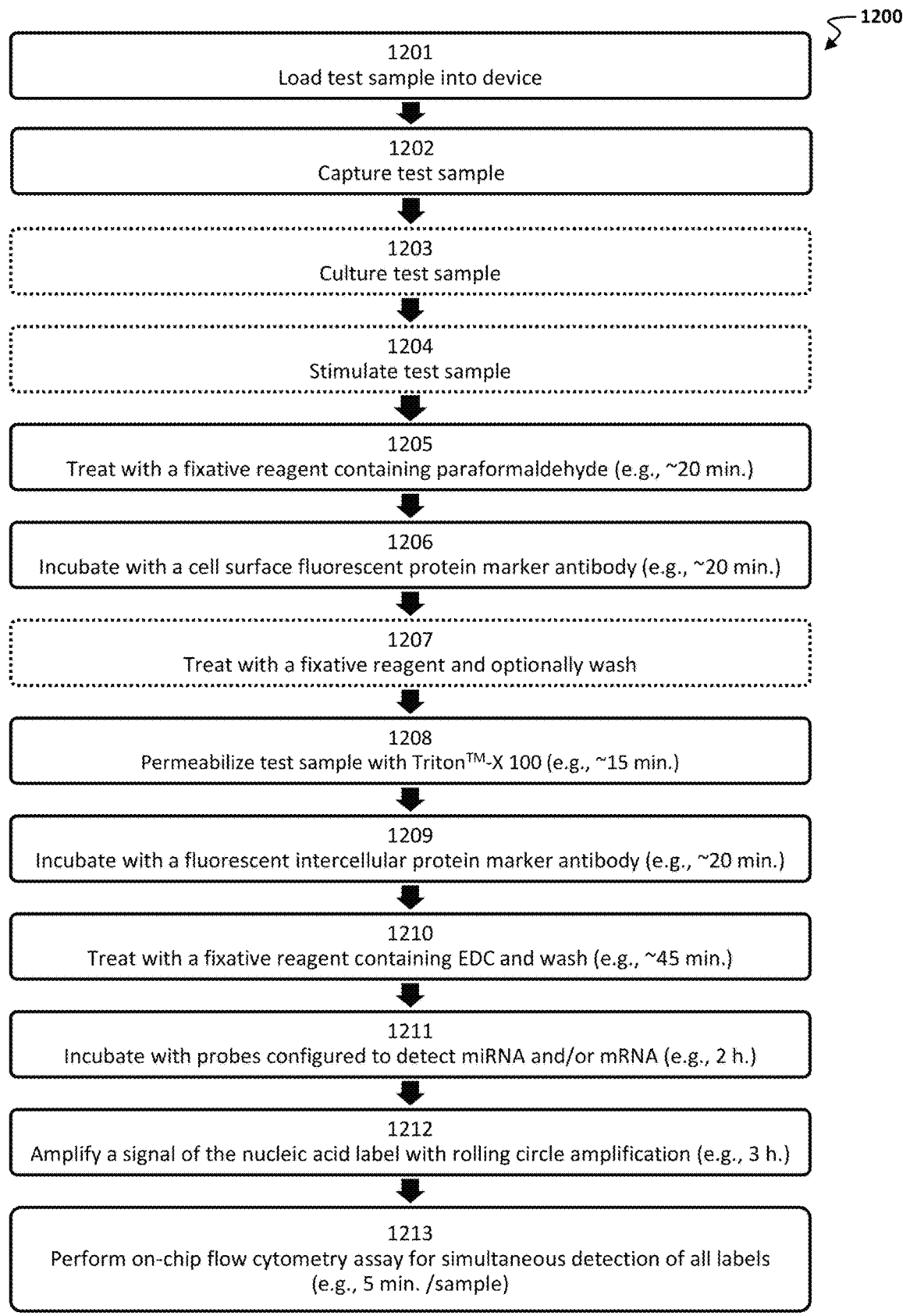
FIG. 12 shows a diagram of an exemplary method 1200 for performing multiplexed analysis of miRNA, mRNA, and proteins under 8 hours, as described herein, while employing minimal sample amounts (e.g., less than 5000 cells, such as of from about 1000 to 3000 cells) and minimal reagent volumes (e.g., less than about 300 nL, such as about 270 nL).

Multiplexed assay scheme for all biomarkers: All microfluidic molecular assays developed on the platform are compatible for multiplexing with each other and will provide systems-level analysis of signaling pathways in the native cellular context at single-cell resolution. Immunostaining the protein biomarkers prior to EDC fixation and ISH of nucleic acid probes allows for the multiplexing of protein and nucleic acid targets in the same samples, and the entire multiplexed assay can be completed in 8 h. (FIG. 12). The use of directly conjugated antibodies allows for the multicolor flow cytometric analysis of all biomarkers at once. The platform and accompanying assays will advance the knowledge of cell signaling pathways and their correlation with disease states, and it holds great potential for both basic cell signaling research and the development of multiplexed miRNA/mRNA/protein biomarker panels for disease diagnostics and companion diagnostics.

OTHER EMBODIMENTS

All publications, patents, and patent applications, including U.S. Provisional Application No. 61/918,402, filed Dec. 19, 2013, mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method for performing multiplexed analysis in a microfluidic device, the method comprising:
 (i) loading a test sample portion into a main port of the device, wherein the device comprises a plurality of assay chambers and the main port is configured to deliver the test sample portion to each assay chamber;
 (ii) capturing the test sample portion within each assay chamber, thereby providing a captured sample portion;
 (iii) treating the captured sample portion with a first fixative reagent in each assay chamber, thereby providing a fixed sample portion;
 (iv) incubating the fixed sample portion with a first protein label in each assay chamber, wherein the first protein label is configured to detect a first target protein, thereby providing a labeled sample portion;
 (v) incubating the labeled sample portion with a second protein label in each assay chamber, wherein the second protein label is configured to detect a second target protein and the second target protein is different than the first target protein, thereby providing a multi-labeled sample portion;
 (vi) incubating the multi-labeled sample portion with a first nucleic acid label, wherein the first nucleic acid label is configured to detect a first target nucleic acid, thereby providing a multiplexed-labeled sample portion;
 (vii) amplifying a signal of the first nucleic acid label, thereby providing an amplified sample portion;
 (viii) detaching the amplified sample portion, thereby providing a detached sample portion; and (ix) performing an on-chip flow cytometry assay of the detached sample portion, thereby performing multiplexed analysis for the target proteins and the target nucleic acid.

2. The method of claim 1, further comprising, after step (v):
treating the multi-labeled sample portion with a second fixative reagent, where the first and second fixative reagents can be the same or different, thereby providing the multi-labeled sample portion for use in step (vi).

3. The method of claim 1, further comprising, before step (v):
permeabilizing the labeled sample portion with a permeabilization reagent.

4. The method of claim 1, wherein step (vii) comprises rolling circle amplification.

5. The method of claim 1, wherein step (ix) comprises transporting the detached sample portion to a flow cytometry channel of the device, hydrodynamically focusing the detached sample portion by employing one or more sheath fluids, and detecting one or more protein label(s) and/or nucleic acid label(s) by applying an excitation source to the hydrodynamically focused sample portion.

6. A microfluidic platform for multiplexed analysis, wherein the platform comprises:
(i) a microfluidic device comprising:
a plurality of assay chambers, wherein each assay chamber is configured to conduct a multiplexed series of assays and each assay chamber is individually addressable;
a main port in fluidic communication with each assay chamber, wherein the main port is configured to deliver a test sample portion to each assay chamber;
a plurality of ports, wherein each assay chamber is in fluidic communication with at least one port;
a flow cytometry channel in fluidic communication with each assay chamber, wherein the flow cytometry channel is configured to hydrodynamically focus the test sample portion; and
a sheath port in fluidic communication with the flow cytometry channel, wherein the sheath port is configured to deliver a sheath fluid to the flow cytometry channel;
(ii) a manifold comprising:
a first reservoir configured to contain the test sample portion, wherein the first reservoir is in fluidic communication with the main port;
a second reservoir configured to contain a first protein label, wherein the second reservoir is in fluidic communication with at least one port or the main port and wherein the first protein label is configured to detect a first target protein;
a third reservoir configured to contain a first fixative reagent, wherein the third reservoir is in fluidic communication at least one port or the main port;
a fourth reservoir configured to contain a first nucleic acid label, wherein the fourth reservoir is in fluidic communication with at least one port or the main port and wherein the first nucleic acid label is configured to detect a first target nucleic acid; and
a fifth reservoir configured to contain one or more sheath fluids, wherein the fifth reservoir is in fluidic communication with the sheath port;

(iii) a pumping system coupled to the first, second, third, fourth, and fifth reservoirs;
(iv) a controller coupled to the pumping system and configured to control the pumping system, wherein the controller is configured to execute the following:
fluidically deliver the test sample portion from the first reservoir to the main port and then to each assay chamber;
fluidically deliver the first protein label from the second reservoir to at least one assay chamber, thereby providing a labeled sample portion;
fluidically deliver the first fixative reagent from the third reservoir to at least one assay chamber containing the labeled sample portion, thereby providing a fixed sample portion;
fluidically deliver the first nucleic acid label from the fourth reservoir to at least one assay chamber containing the fixed sample portion, thereby providing a multi-labeled sample portion;
fluidically deliver the multi-labeled sample portion(s) from at least one assay chamber to the flow cytometry channel; and
fluidically deliver one or more sheath fluids from the fifth reservoir to the sheath port;
(v) a stage coupled to the device and configured to control a temperature within the plurality of assay chambers; and
(vi) an excitation source configured to provide an excitation energy to the flow cytometry channel, wherein the excitation source is configured to excite the first protein label, the first nucleic acid label, or a secondary label configured to directly or indirectly bind to the first protein label or the first nucleic acid label, thereby providing an excited label for the multi-labeled sample portion; and
(vii) a detector configured to receive an emission spectrum from the excited label.

7. The platform of claim 6, wherein (ii) the manifold further comprises a sixth reservoir configured to contain one or more amplification reagents, wherein the sixth reservoir is in fluidic communication with at least one port or the main port and wherein the one or more amplification reagents are configured to amplify a signal of the first nucleic acid label.

8. The platform of claim 7, wherein (iv) the controller is further configured to fluidically deliver the one or more amplification reagents to the multi-labeled sample portion prior to the multi-labeled sample portion being delivered to the flow cytometry channel.

9. The platform of claim 6, wherein (ii) the manifold further comprises a valve disposed between the first reservoir and the main port, and wherein (iv) the controller is further configured to operate the valve.

10. The platform of claim 6, wherein (ii) the manifold further comprises a valve disposed between each reservoir and the port in fluidic communication with each reservoir, and wherein (iv) the controller is further configured to operate each valve.

11. The platform of claim 6, wherein (iii) the pumping system further comprises a pressure source and a pressure controller configured to be controlled by the controller.

* * * * *